US012622925B2

(12) United States Patent
Phillips et al.

(10) Patent No.: US 12,622,925 B2
(45) Date of Patent: May 12, 2026

(54) EDIBLE ENTEROSORBENTS USED TO MITIGATE ACUTE EXPOSURES TO INGESTIBLE ENVIRONMENTAL TOXINS FOLLOWING OUTBREAKS, NATURAL DISASTERS AND EMERGENCIES

(71) Applicants: TEXAS A&M UNIVERSITY, College Stationj, TX (US); Timothy D Phillips, College Station, TX (US); Meichen Wang, College Station, TX (US)

(72) Inventors: Timothy D Phillips, College Station, TX (US); Meichen Wang, College Station, TX (US)

( * ) Notice: Subject to any disclaimer, the term of this patent is extended or adjusted under 35 U.S.C. 154(b) by 977 days.

(21) Appl. No.: 17/262,734

(22) PCT Filed: Aug. 20, 2019

(86) PCT No.: PCT/US2019/047356
§ 371 (c)(1),
(2) Date: Jan. 24, 2021

(87) PCT Pub. No.: WO2020/041379
PCT Pub. Date: Feb. 27, 2020

(65) Prior Publication Data
US 2021/0137971 A1     May 13, 2021

Related U.S. Application Data

(60) Provisional application No. 62/719,924, filed on Aug. 20, 2018.

(51) Int. Cl.
| | |
|---|---|
| A61K 33/06 | (2006.01) |
| A23K 20/158 | (2016.01) |
| A23K 20/28 | (2016.01) |
| A23L 33/00 | (2016.01) |
| A23L 33/115 | (2016.01) |
| A23L 33/16 | (2016.01) |
| A61K 9/14 | (2006.01) |
| A61K 47/24 | (2006.01) |

(52) U.S. Cl.
CPC ........... *A61K 33/06* (2013.01); *A23K 20/158* (2016.05); *A23K 20/28* (2016.05); *A23L 33/115* (2016.08); *A23L 33/16* (2016.08); *A23L 33/40* (2016.08); *A61K 9/14* (2013.01); *A61K 47/24* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 9,597,313 B2 * | 3/2017 | Phillips | .................. | A61P 39/00 |
| 2008/0008763 A1 * | 1/2008 | Phillips | .................. | A61K 35/02 |
| | | | | 424/489 |
| 2016/0287617 A1 * | 10/2016 | Lara Arellano | ...... | B01J 20/3253 |

FOREIGN PATENT DOCUMENTS

WO     WO-2012091598 A1 *     7/2012     ............... A23L 1/09

OTHER PUBLICATIONS

Meichen Wang, Cody R. Maki, Youjun Deng, Yanan Tian, and Timothy D. Phillips; Development of High Capacity Enterosorbents for Aflatoxin B1 and Other Hazardous Chemicals; DOI: 10.1021/acs.chemrestox.7b00154 Published Aug. 2, 2017 (Year: 2017).*
Aflatoxin (AfB1), SciFinder (CAS Registry No. 1162-65-8), https://www.chemspider.com/Chemical-Structure.162470.html.
Pentachlorophen ol (PCP), HSDB (Hazardous Substances Data Bank), https://pubchem.ncbi.nlm.nih.gov/compound/Pentachlorophenol.
Benzo[a]pyrene (BaP), HSDB (Hazardous Substances Data Bank), https://pubchem.ncbi.nlm.nih.gov/compound/Benzo_a_pyrene.
Lindane, HSDB (Hazardous Substances Data Bank), https://pubchem.ncbi.nlm.nih.gov/compound/Lindane.
Diazinon, PPDB (Pesticide Properties DataBase), http://sitem.herts.ac.uk/aeru/ppdb/en/atoz.htm.
Aldicarb, PPDB (Pesticide Properties DataBase), http://sitem.herts.ac.uk/aeru/ppdb/en/atoz.htm.
Linuron, PPDB (Pesticide Properties DataBase), http://sitem.herts.ac.uk/aeru/ppdb/en/atoz.htm.
1,2,3-Trichloropropane (TCP), EPA EPI Suite, https://www.epa.gov/tsca-screening-tools/epi-suitetm-estimation-program-interface.
Phenol, HSDB (Hazardous Substances Data Bank), https://pubchem.ncbi.nlm.nih.gov/compound/Phenol.
Benzene, HSDB (Hazardous Substances Data Bank), https://pubchem.ncbi.nlm.nih.gov/compound/Benzene.
Toluene, HSDB (Hazardous Substances Data Bank), https://pubchem.ncbi.nlm.nih.gov/compound/Toluene.
Glyphosate, PPDB (Pesticide Properties DataBase), http://sitem.herts.ac.uk/aeru/ppdb/en/atoz.htm.
Dichlorodiphenyltrichl oroethane (DDT), HSDB (Hazardous Substances Data Bank), https://pubchem.ncbi.nlm.nih.gov/compound/DDT].

* cited by examiner

*Primary Examiner* — Robert A Wax
*Assistant Examiner* — Andre Mach
(74) *Attorney, Agent, or Firm* — Craig C. Conrad

(57) ABSTRACT
An edible enterosorbent containing a treated enterosorbent, wherein the treated enterosorbent comprises a parent sorbent that has been acid and/or lecithin treated, and wherein the treated sorbent is operable for adsorption of one or more toxins from a gastrointestinal tract of a living being when introduced thereto, such that a bioavailability of and exposure of the living being to the one or more toxins is decreased. Methods of making and utilizing the edible enterosorbent are also provided.

4 Claims, 25 Drawing Sheets

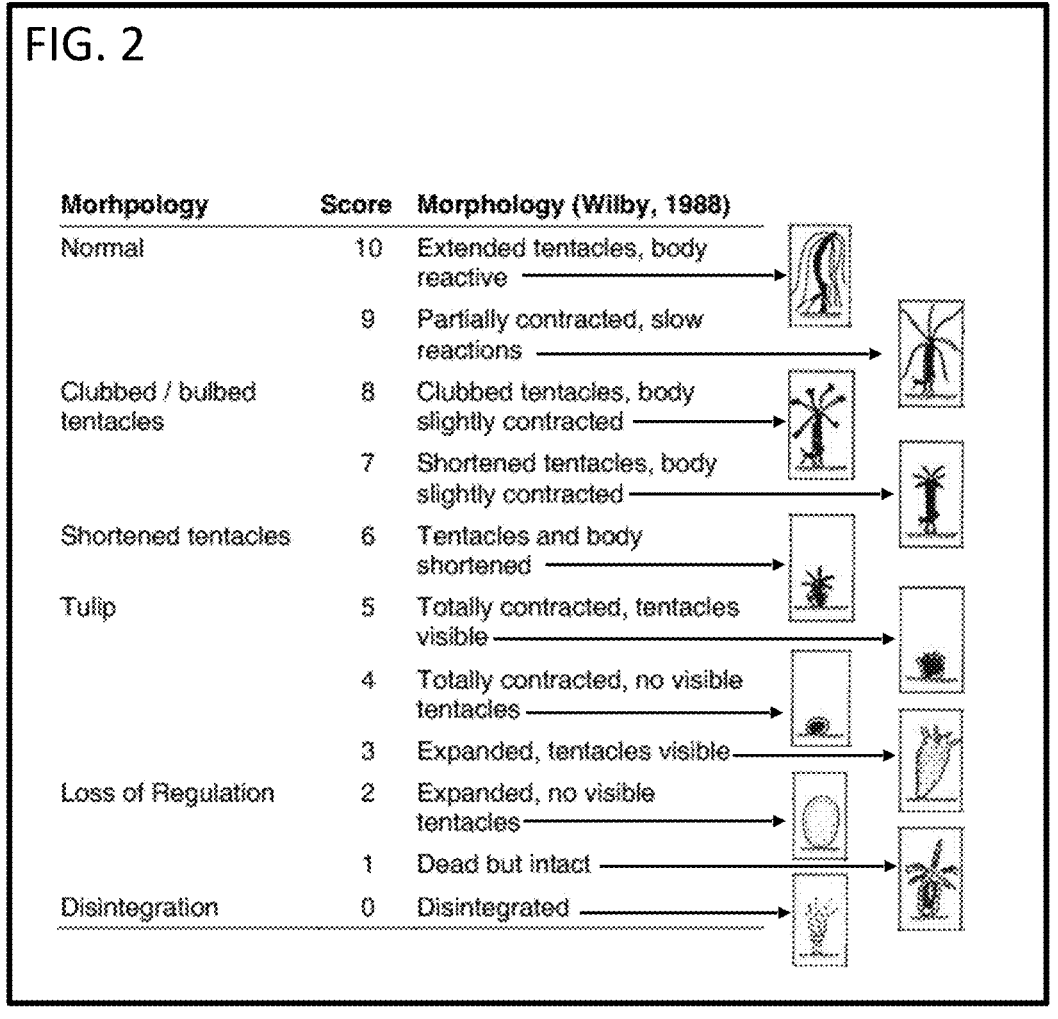

| Morhpology | Score | Morphology (Wilby, 1988) | | |
|---|---|---|---|---|
| Normal | 10 | Extended tentacles, body reactive | | |
|  | 9 | Partially contracted, slow reactions | | |
| Clubbed / bulbed tentacles | 8 | Clubbed tentacles, body slightly contracted | | |
|  | 7 | Shortened tentacles, body slightly contracted | | |
| Shortened tentacles | 6 | Tentacles and body shortened | | |
| Tulip | 5 | Totally contracted, tentacles visible | | |
|  | 4 | Totally contracted, no visible tentacles | | |
|  | 3 | Expanded, tentacles visible | | |
| Loss of Regulation | 2 | Expanded, no visible tentacles | | |
|  | 1 | Dead but intact | | |
| Disintegration | 0 | Disintegrated | | |

FIG 6A
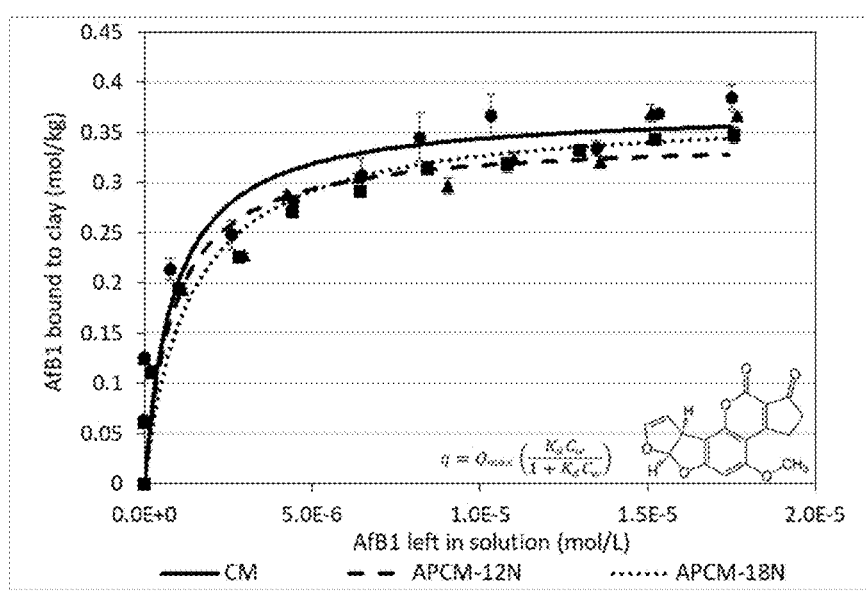
FIG 6B
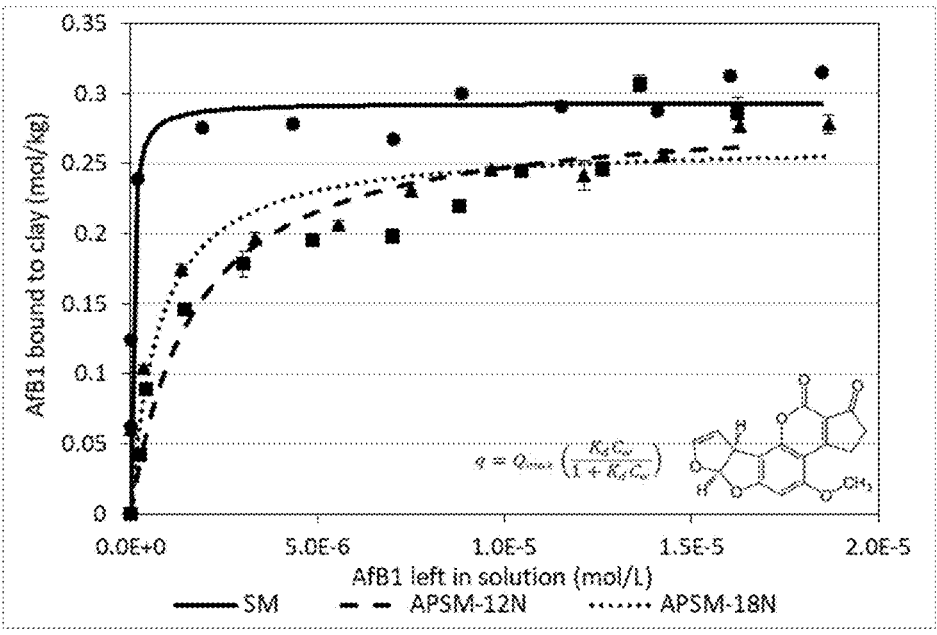
FIG 6C.
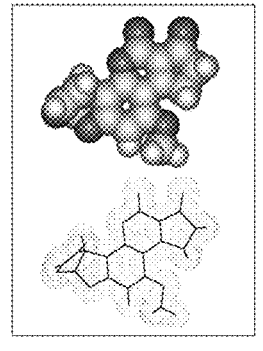 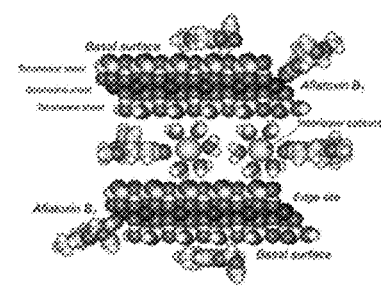

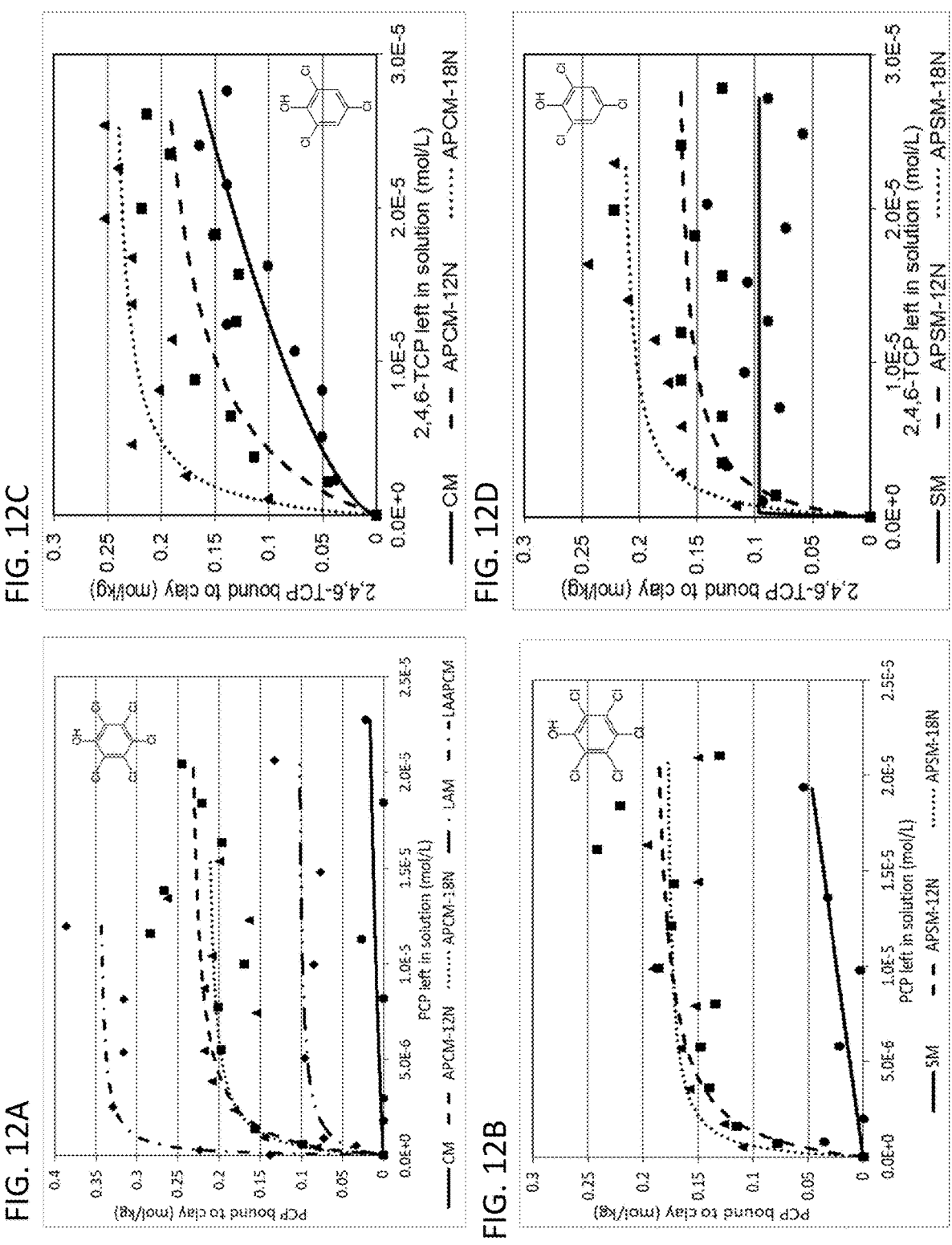

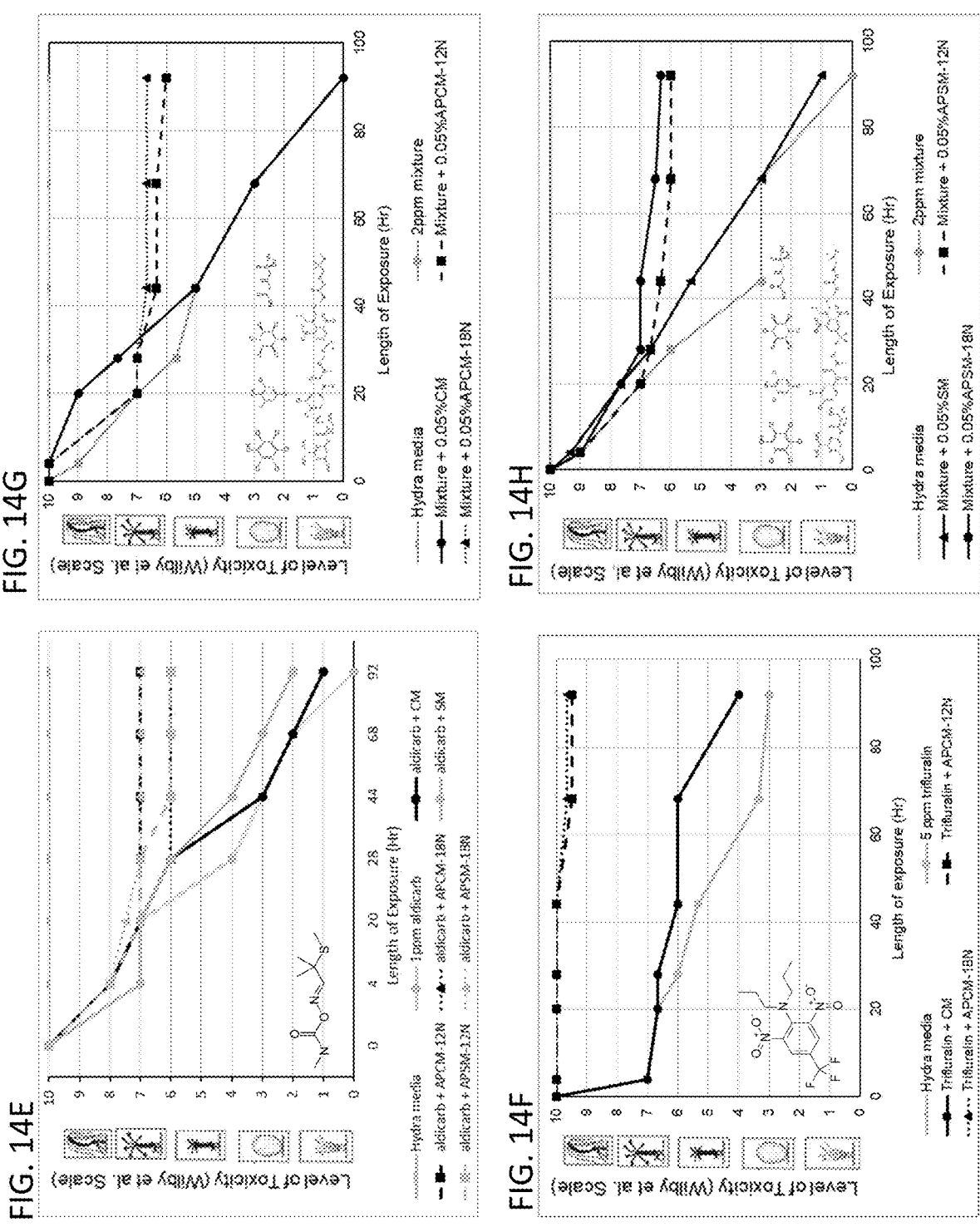

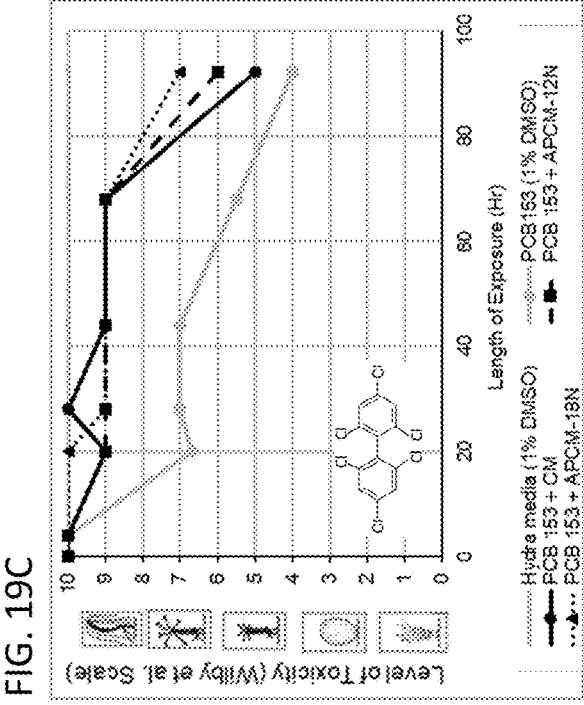
FIG. 19C
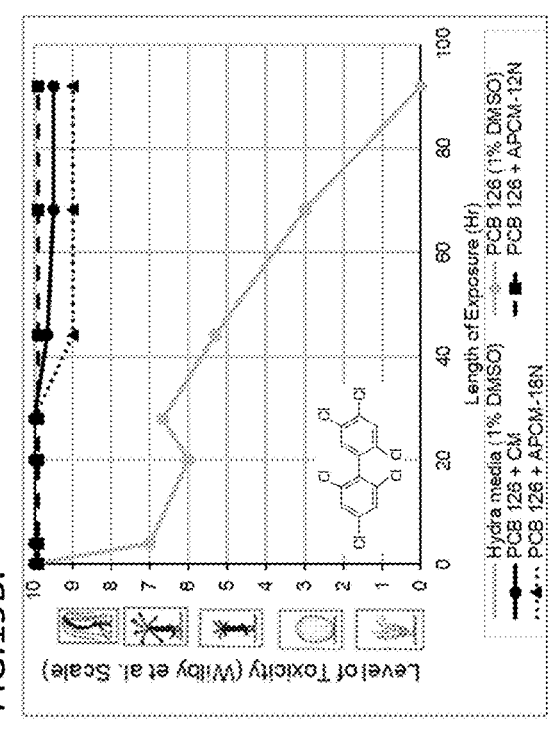
FIG.19A
FIG.19B.

FIG. 22

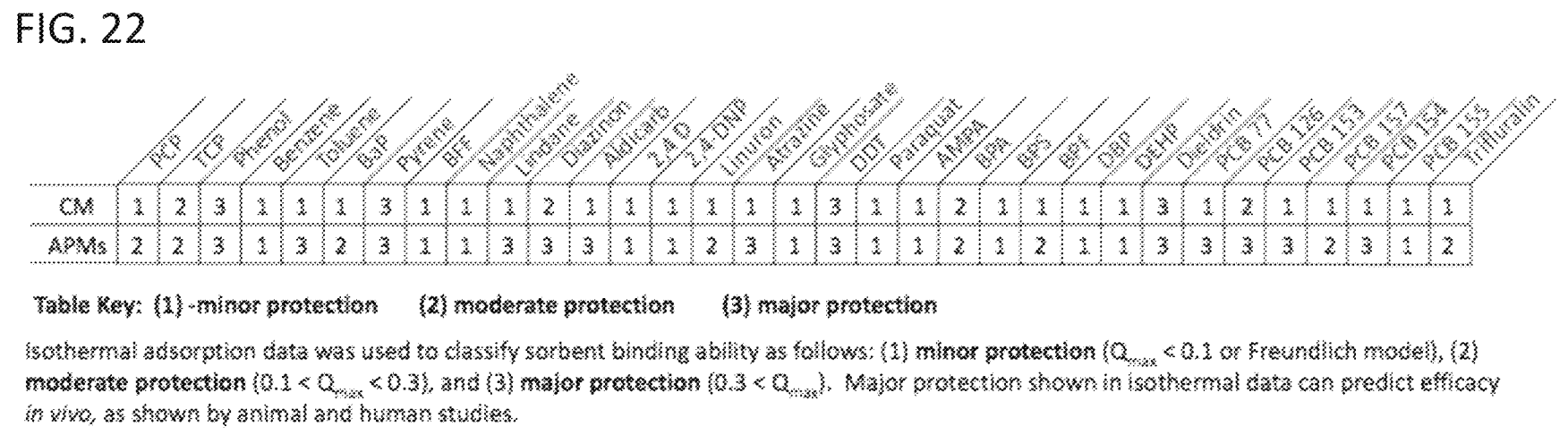

| | TCP | TCP | Toluene | Benzene | BaP | Pyrene | BFT | Naphthalene | Lindane | Diazinon | TCC | 2,4-DNP | Uranium | Atrazine | Glyphosate | 100 | Tethered | MPAA | VX | GB | GD | DBP | DEHP | Dieldrin | PCB 77 | PCB 126 | PCB 153 | PCB 127 | PCB 154 | PCB 155 | Trihalom |
|---|---|---|---|---|---|---|---|---|---|---|---|---|---|---|---|---|---|---|---|---|---|---|---|---|---|---|---|---|---|---|---|
| CM | 1 | 2 | 3 | 1 | 1 | 1 | 1 | 1 | 1 | 1 | 2 | 1 | 1 | 1 | 3 | 3 | 1 | 2 | 1 | 1 | 1 | 1 | 3 | 1 | 2 | 1 | 1 | 1 | 1 | 1 | 1 |
| APMs | 2 | 2 | 3 | 1 | 3 | 1 | 1 | 3 | 3 | 1 | 3 | 2 | 3 | 1 | 3 | 3 | 1 | 2 | 2 | 1 | 3 | 1 | 3 | 3 | 3 | 3 | 2 | 3 | 1 | 1 | 2 |

Table Key: (1) - minor protection     (2) moderate protection    (3) major protection

Isothermal adsorption data was used to classify sorbent binding ability as follows: (1) *minor protection* ($Q_{max}$ < 0.1 or Freundlich model), (2) *moderate protection* (0.1 < $Q_{max}$ < 0.3), and (3) *major protection* (0.3 < $Q_{max}$). Major protection shown in isothermal data can predict efficacy *in vivo*, as shown by animal and human studies.

EDIBLE ENTEROSORBENTS USED TO MITIGATE ACUTE EXPOSURES TO INGESTIBLE ENVIRONMENTAL TOXINS FOLLOWING OUTBREAKS, NATURAL DISASTERS AND EMERGENCIES

FEDERALLY SPONSORED RESEARCH

This invention was made with government support under Grant No. P42 ES0277704 awarded by the National Institute of Environmental Health Sciences Superfund hazardous Substance Research and Training Program (NIEHS SRP). The government may have certain rights in the invention.

RELATED APPLICATIONS

This application is related to a U.S. Provisional Application 62/719,924 filed on Aug. 20, 2018 with the same title.

JOINT RESEARCH AGREEMENTS

Not Applicable.

SEQUENCE LISTING

Not Applicable.

BACKGROUND

People and animals can be unintentionally exposed to mixtures of hazardous mycotoxins, environmental chemicals and microbes by contaminated water, food and feed supplies following natural and man-made disasters. Mycotoxin contamination of food and feed has a major impact on agriculture and health. The mycotoxin problem is a concern worldwide, but especially in semitropical and tropical areas that encompass 4.5 billion people and their animals, where mold growth and production of mycotoxins are high. Importantly, a large portion of the US is within this zone.

Mycotoxins are secondary metabolites produced by various fungi, which are widespread and cause problems, especially during extended periods of heat and drought. Among these mycotoxins, aflatoxin and zearalenone (ZEN) are most commonly found in animal feed and human food, such as cereal crops including corn, barley, oats and wheat, and produce significant adverse effects on agriculture and health (Grant, P. G., & Phillips, T. D., 1998; Lemke, S. L., & Phillips, T. D., 1998). Symptoms caused by aflatoxin and ZEN include growth stunting, weight loss, nausea, vomiting, liver toxicity, reproduction defects and cancer. Global warming favors drought and mold growth, thus enhancing the threat of mycotoxin contamination of the food supply during outbreaks and emergencies.

Thus, natural and man-made disasters (such as hurricanes and floods) can significantly mobilize environmental chemical contaminants, expose humans and animals to contaminated soil/sediment and threaten the safety of municipal drinking water and food sources. A major challenge associated with these disasters and emergencies is the protection of: 1) vulnerable communities and neighborhoods, 2) first responders, and 3) those involved in management and cleanup of contaminated sites. Multiple classes of organic chemicals such as industrial solvents, polycyclic aromatic hydrocarbons (PAHs), pesticides, polychlorinated biphenyls (PCBs) and plasticizers have been prioritized by the Agency for Toxic Substances and Disease Registry (ATSDR) as important hazardous substances.

The enterosorbent composition of this invention is broad-acting and useful for adsorption of one or more toxins from an environment or a gastrointestinal tract of a living organism. Examples used herein show how benzo[a]pyrene (BaP), pentachlorophenol (PCP), 2,4,6-trichlorophenol (2,4,6-TCP), lindane, glyphosate, diazinon, aldicarb, linuron, trifluralin, PCBs, bisphenol A (BPA), were studied as representative chemicals in each class based on their wide distribution and importance. BaP is a well-known environmental pollutant and a human and animal carcinogen, which is commonly found at contaminated sites and largely distributed in Africa because of the local burning methods (Johnson, N. M. et al., 2009). PCP is widespread and persistent and a highly toxic anthropogenic organochlorine pesticide. It is classified as a possible carcinogen to humans by the International Agency for Research on Cancer (IARC) (Zheng, W. et al., 2012). PCP was banned for the purchase and use by general public but is still used in industries. 2,4,6-TCP has been commonly used as a pesticide and wood preservative (Hameed, 2007). It is reported that exposure to 2,4,6-TCP may increase the risk of behavioral impairment in children and is reasonably anticipated to be a human carcinogen. These chlorophenol compounds are persistent in the environment and can be commonly detected in rivers, ponds and soils (Gao, et al., 2008). Lindane is a hexachlorocyclohexane that is widely used to treat scabies and pediculosis. It is persistent and undegradable, and thus tends to bioaccumulate in the food chain Glyphosate is the most used organophosphorus pesticide to control weeds. Glyphosate is used as a broad-spectrum systemic herbicide and crop desiccant, and acts by inhibiting the plant enzyme 5-enolpyruvylshikimate-3-phosphate synthase. Approximately 90% of transgenic crops are glyphosate-resistant and the amount is growing at a steady peace. Diazinon is an organophosphorus insecticide, which has been widely and effectively used throughout the world with applications in agriculture and horticulture for controlling insects. Its toxicity is due to the inhibition of the enzyme acetylcholine esterase. Aldicarb is an acutely toxic insecticide that belongs to the carbamate class. The toxicity of carbamate insecticides, as well as organophosphorus compounds, is due to the inhibition of the enzyme acetylcholine esterase. Linuron is a phenylurea herbicide used widely to selectively control weeds and grasses by inhibiting photosynthesis. It is also considered as an androgen receptor that can produce reproductive malformations. Trifluralin is a selective, pre-emergence dinitroaniline herbicide which controls a wide variety of grasses and broadleaf weeds by interrupting mitosis, and thus can control weeds as they germinate. It is one of the most widely used herbicides. Trifluralin has been banned in the European Union since 2008, primarily due to its high toxicity to aquatic life. Exposure to these pesticides can stimulate lipid peroxidation, paralyze the respiratory system, cause endocrine disruption and affect the nervous and reproductive systems, etc (Bertrand, D. B., 1991; Tiemann, U, 2008; Yarsan, E., Tanyuksel, M., Celik, S., & Aydin, A., 1999). Other representative chemicals include coplanar and non-coplanar PCB congeners and PCB mixtures, and bisphenol A (BPA). The physical and chemical properties of PCBs, such as stability, resistance and low vapor pressures, result in their persistence in the environment and make them valuable and widely used as electrical insulators. An important environmental concern about PCBs is their incorporation into the food chain BPA-based plastics are widely used in water bottles and sports equipment, etc. BPA is a xeno-estrogen that can exhibit estrogen-mimicking and hormonelike properties, therefore, exposure to BPA can affect growth, reproduction and development.

FIG. 1 shows the chemical structures of a few of the toxins that the herein disclosed enterosorbents effectively bind, including (A) AfB1, (B) ZEN, (C) BaP, (D) PCP, (E) 2, 4, 6-TCP, (F) lindane, (G) glyphosate, (H) diazion, (I) anticarb; (J) Linuron; (K) trifluralin; (L) PCB 77; (M) PCB 126; (N) PCB 153; (0) PCB 157; (P) PCB 154; (Q) PCB 155; and (R) Bisphenol A. The molecular models of each chemical can be determined using computational quantum mechanical AM1 methods.

Contamination with bacteria is commonly seen in the environment during man-made and natural disasters, especially in developing countries. *Escherichia coli* (*E. coli*) is a Gram-negative bacterium that is commonly found in the lower intestine of warm-blooded organisms. It commonly threatens water and food supplies at the site of disasters, causing food poisoning and severe food-borne disease. Pathogenic *E. coli* strains are responsible for infections of the enteric, urinary, pulmonary, and nervous systems. During disasters, strategies for the mitigation of bacteria, such as *E. coli* are also warranted. We chose *E. coli* strain K-12 to investigate because it approximates wild-type *E. coli* and has been maintained as a laboratory strain with minimal genetic manipulation (Blattner, F. R. et al., 1997).

Acid-activated clays have been developed and used extensively for bleaching oils, removing plant pigments, and sequestering various organic and inorganic contaminants from water during decontamination and purification procedures. However, there are no reports of acid activated clays being used for enterosorbent therapy to reduce toxin exposures in humans and animals. As noted above, during outbreaks of mycotoxicoses, high levels of mycotoxin mixtures (e.g., aflatoxins and zearalenone) can frequently occur as contaminants of food and feed, and result in disease and death in people and animals at the site of the disaster.

Not wanting to be bound by theory, mechanism of the enterosorbent of this inventions protection involves adsorption of toxins onto porous and active surfaces of sorbents, resulting in reduced concentration of toxin in the gastrointestinal tract and decreased bioavailability and toxicity.

Some enterosorbents have high efficacy for aflatoxin, but had a limited ability to sorb other toxins. The only conventional material that has shown good and broad binding of ZEN and environmental chemicals is activated carbon (and carbon mixtures); however (due to the presence of polycyclic aromatic hydrocarbons as contaminants) the safety of carbon is of concern. Accordingly, a need exists for safe, practical, and broad-acting strategies to mitigate the effects of (and exposures to) environmental chemical mixtures, microbes and mycotoxins during outbreaks and emergencies. The enterosorbents of this invention use a variety of phyllosilicate-type minerals including: synthetic phyllosilicate type mineral; a natural phyllosilicate-type mineral; a montmorillonite clay; a sodium montmorillonite clay; a calcium montmorillonite clay; or combination thereof. Specific embodiments use acid processed montmorillonite clays (APM) and lecithin amended montmorillonites (LAM) that were developed to be broad-acting for toxins. A variety of calcium montmorillonites (CM) and sodium montmorillonites (SM) were utilized as parent base materials. The CM disclosed in this study has been shown to be safe for animal and human consumption, and its inclusion in feedstuffs and food were effective in protecting numerous animal species from aflatoxin and reducing biomarkers of aflatoxin exposure in humans.

SUMMARY

Disclosed herein is an enterosorbent comprising: a treated sorbent, wherein the treated sorbent comprises a parent sorbent that has been acid and/or lecithin treated, and wherein the treated sorbent is operable for adsorption of one or more toxins from a gastrointestinal tract of a living being when introduced thereto, such that a bioavailability of and exposure of the living being to the one or more toxins is decreased.

Also disclosed herein is a method of producing an enterosorbent, the method comprising: processing a parent clay to produce a processed clay, wherein the processing comprises: acid treating to produce an acid treated clay via exposure to reagent grade sulfuric acid solution having a concentration (e.g., an equivalent concentration or normality (N)) of greater than or equal to about 6N, 12N, or 18N, or in a range of from about 6N to about 18N or from about 6N to about 12N; and/or lecithin treating to produce a lecithin treated clay via modification with lecithin at 100% cation exchange capacity. Further disclosed herein is a method of reducing exposure of a living being to one or more toxins, the method comprising: introducing into the living being an enterosorbent as disclosed herein.

BRIEF DESCRIPTION OF THE DRAWINGS

A more complete and through understanding of the present embodiments and advantages thereof may be acquired by referring to the following description taken in conjunction with the accompanying drawings, in which like reference numbers indicate like features and wherein:

FIG. 1 shows the chemical structures of a few of the toxins that the herein disclosed enterosorbents effectively bind, including (A) AfB1, (B) ZEN, (C) BaP, (D) PCP, (E) 2, 4, 6-TCP, (F) lindane, (G) glyphosate, (H) diazion, (I) anticarb; (J) Linuron; (K) trifluralin; (L) PCB 77; (M) PCB 126; (N) PCB 153; (0) PCB 157; (P) PCB 154; (Q) PCB 155; and (R) Bisphenol A.

FIG. 2 shows a depiction of hydra morphology scale. The scale is graded from 0-10, wherein 10 represents a normal living hydra and 0 represents a disintegrated hydra. The physiologic conditions of hydra were assessed with a dissecting microscope.

FIG. 6A and FIG. 6B show Langmuir plots of AfB1 on acid processed calcium montmorillonites (APCM) (FIG. 6A) and acid processed sodium montmorillonites (APSM) (FIG. 6B) versus parent calcium or sodium montmorillonites (CM, or SM). These plots show the observed and predicted Qmax values at pH 6.5; CM: Qmax=0.37; Kd=1E6; APCM-12N: Qmax=0.34; Kd=1E6; APCM-18N: Qmax=0.37; Kd=8E5. (FIG. 6B) SM: Qmax=0.3; Kd=2E7; APSM-12N: Qmax=0.29; Kd=6E6; APSM-18N: Qmax=0.27; Kd=2E6;

FIG. 6C shows the molecular structure of aflatoxin B1 and how this and other molecules are believed to interact with the basal layers and interlayer spaces of the montmorillonite mineral, wherein the aflatoxin B1 may intercalate and interact with cations.

(FIG. 9A) APCM-12N: Qmax=0.34; Kd=1E6; APCM-18N: Qmax=0.37; Kd=8E5; Co APCM-12N: Qmax=0.07; Kd=5E5; Co APCM-18N: Qmax=0.05; Kd=6E5. (FIG. 9B) APCM-12N: Qmax=0.21; Kd=6E6; APCM-18N: Qmax=0.24; Kd=2E6; Co APCM-12N: Qmax=0.11; Kd=9E6; Co APCM-18N: Qmax=0.17; Kd=1E7;

FIG. 12A and FIG. 12B show Langmuir plots of PCP on APCM (FIG. 12A) and lecithin amended montmorillonite (LAM), and APSM (FIG. 12B) with comparison of parent calcium or sodium montmorillonites (CM or SM). APCM-12N: Qmax=0.23; Kd=2E6; APCM-18N: Qmax=0.21; Kd=1E7; LAM: Qmax=0.11; Kd=2E6. APSM-12N: Qmax=0.1; Kd=3E6; APSM-18N: Qmax=0.14; Kd=5E7;

FIG. 12C and FIG. 12 D show Langmuir plots of 2,4,6-TCP on APCM (FIG. 12C) and APSM (FIG. 12D) versus parent montmorillonites at 24° C. APCM-12N: Qmax=0.23; Kd=2E5; APCM-18N: Qmax=0.25; Kd=8E5; APSM-12N: Qmax=0.17; Kd=7E5; APSM-18N: Qmax=0.22; Kd=1E6.

FIG. 12E and FIG. 12F show Langmuir plots of PCP on APCM and LAM with comparison of parent CM (FIG. 12E), wherein APCM-12N: Qmax=0.24; Kd=1.2E6; APCM-18N: Qmax=0.22; Kd=1.9E6; LAM: Qmax=0.11; Kd=2E6; LAAPCM: Qmax=0.35; Kd=6.5E6; and FIG. 12F shows Langmuir plots of lindane on APCM and LAM versus parent CM, wherein APCM-12N: Qmax=0.5; Kd=2E5; APCM-18N: Qmax=0.53; Kd=1E5; LAM: Qmax=0.12; Kd=2E5; LAAPCM: Qmax=0.38; Kd=2E5.

(FIG. 13A) APCM-12N:

Qmax=0.5; Kd=2E5; APCM-18N: Qmax=0.53; Kd=1E5; LAM: Qmax=0.12; Kd=2E5; (FIG. 13B) CM: Qmax=0.19; Kd=4E6; APCM-12N: Qmax=0.47; Kd=2E6; APCM-18N: Qmax=0.5; Kd=4E5; LAM: Qmax=0.22; Kd=1E6; (FIG. 13C) APCM-12N: Qmax=0.4; Kd=4E6; APCM-18N: Qmax=0.48; Kd=3E6; LAM: Qmax=0.47; Kd=2E7; and (FIG. 13D) CM: Qmax=0.09; Kd=5E4; APCM-12N: Qmax=0.15; Kd=5E4; APCM-18N: Qmax=0.22; Kd=4E4;

FIG. 14A, FIG. 14B, FIG. 14C, FIG. 14D, FIG. 14E, FIG. 14F show hydra toxicity and protection by parent montmorillonites and APM at the 0.1% inclusion level against PCP (FIG. 14A), BaP with MAP (FIG. 14B), and aldicarb (FIG. 14C); hydra media and toxin controls are included in each figure for comparison; Hydra toxicity and protection by parent montmorillonites and APCM (FIG. 14D) and APSM (FIG. 14E) at the 0.1% inclusion level against glyphosate. FIG. 14F shows hydra toxicity and protection by parent montmorillonites and APM at the 0.2% inclusion level against trifluralin. Hydra media and toxin controls are included for comparison.

FIG. 14G and FIG. 14H show hydra toxicity and protection by parent montmorillonites and APCM (FIG. 14G) and APSM (FIG. 14H) at the 0.05% inclusion level against a mixture of pesticides (PCP, 2,4,6 PCP, lindane, diazinon, linuron, trifluralin, glyphosate, aldicarb) with equal concentrations of 2 ppm for each pesticide.

(FIG. 16A) CM: Qmax=0.13; Kd=5E5; APCM-12N: Qmax=0.35; Kd=1E6; APCM-18N: Qmax=0.27; Kd=2E5. (FIG. 16B) CM: Qmax=0.19; Kd=8E5; APCM-12N: Qmax=0.36; Kd=2E5; APCM-18N: Qmax=0.34; Kd=5E5. (FIG. 16C) APCM-12N: Qmax=0.17; Kd=1E5; APCM-18N: Qmax=0.22; Kd=1E5.

(FIG. 17A) CM HT: Qmax=0.11; Kd=1E5; APCM-12N HT: Qmax=0.16; Kd=2E5; APCM-18N HT: Qmax=0.19; Kd=5E4. (FIG. 17B) CM HT: Qmax=0.09; Kd=1E5; APCM-12N HT: Qmax=0.18; Kd=7E4; APCM-18N HT: Qmax=0.2; Kd=6E4. (FIG. 17C) APCM-12N HT: Qmax=0.43; Kd=4E4; APCM-18N HT: Qmax=0.39; Kd=5E4.

(FIG. 18A) APCM-12N: Qmax=0.23; Kd=4E4; APCM-18N: Qmax=0.21; Kd=9E4. (FIG. 18B)

APCM-12N: Qmax=0.17; Kd=1E5; APCM-18N: Qmax=0.22; Kd=1E5. (FIG. 18C) APCM-12N: Qmax=0.05; Kd=3E5; APCM-18N: Qmax=0.09; Kd=1E5.

FIG. 19A, FIG. 19B, FIG. 19C show Hydra toxicity and protection by parent montmorillonites and APM at the 0.1% inclusion level against PCB 77 (FIG. 19A), 126 (FIG. 19B) and 153 (FIG. 19C). Hydra media and toxin controls are included for comparison.

(FIG. 21A) and 37° C. (HT). (FIG. 21A) CM: Qmax=0.26; Kd=5E5; APCM-12N: Qmax=0.26; Kd=2E6; APCM-18N: Qmax=0.25; Kd=1E6. (FIG. 21B) CM HT: Qmax=0.34; Kd=1E6; APCM-12N HT: Qmax=0.31; Kd=1E6; APCM-18N HT: Qmax=0.27; Kd=1E6.

FIG. 22 shows isothermal adsorption data for a variety of environmental chemicals. Hydra were used to classify sorbent binding ability as follows: (1) minor protection (Qmax<0.1 or Freundlich model), (2) moderate protection (0.1<Qmax<0.3), and (3) major protection (0.3<Qmax). Major protection shown in isothermal data can predict efficacy in vivo, as shown by animal and human studies.

DETAILED DESCRIPTION OF DISCLOSED EXEMPLARY EMBODIMENTS

Figure 3:
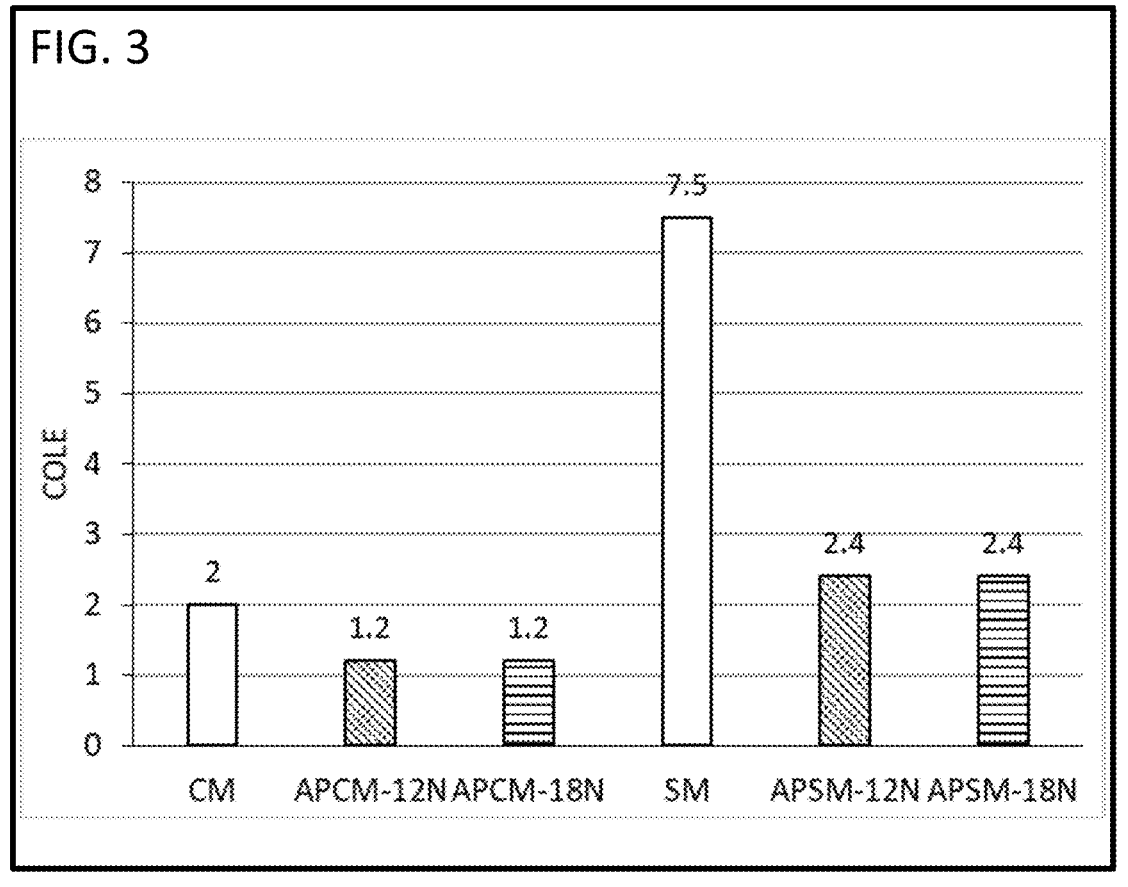
FIG. 3 shows the coefficient of linear expansibility (COLE) for sorbents in water; this value relates to the swelling of materials in water, where a higher number indicates a higher linear expansibility and swelling.

Definitions:

It will be readily apparent to one skilled in the art that various substitutions and modifications may be made in the invention disclosed herein without departing from the scope and spirit of the invention. Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

It should be understood at the outset that although an illustrative implementation of one or more exemplary embodiments are provided below, the disclosed compositions, methods, and/or products may be implemented using any number of techniques, whether currently known or in existence. The disclosure should in no way be limited to the illustrative implementations, drawings, and techniques illustrated herein below, including the exemplary designs and implementations illustrated and described herein, but may be modified within the scope of the appended claims along with their full scope of equivalents.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to:"

The term "a" or "an" as used herein in the specification may mean one or more. As used herein in the claim(s), when used in conjunction with the word "comprising", the words "a" or "an" may mean one or more than one. As used herein "another" may mean at least a second or more.

The term 'enterosorbent' as used herein refers to a material that binds a variety of environmental toxins, including chemicals, microbes and mycotoxins in the gastrointestinal tract of animals and humans; or in an environment where the animals and humans may be exposed; or in food or water that may be ingested by animals and humans. This binding action results in decreased bioavailability and toxin exposures from food and water, as detailed herein.

The term 'living being' refers to invertebrates, vertebrates, animals, and/or humans.

The term "strong acid" is an acid that dissociates. Examples of strong acids are hydrochloric acid (HCl), perchloric acid ($HClO_4$), nitric acid ($HNO_3$) and sulfuric acid ($H_2SO_4$). In contrast, the term "weak acid" is an acid that only partially dissociated, with both the undissociated acid and its dissociation products being present, in solution, in equilibrium with each other. Any acid with a pKa value that is less than about $-2$ is classed as a strong acid.

The term "Lecithin" as used herein, is a generic term to designate any group of yellow brownish fatty substances occurring in animal and plant tissues that are amphiphilic. Lecithins attract both water and fatty substances (and so are both hydrophilic and lipophilic), and are used for smoothing food textures, emulsifying, homogenizing liquid mixtures, and repelling sticking materials. Lecithins can be mixtures of glycerophospholipids including phosphatidylcholine, phosphatidylethanolamine, phosphatidylinositol, phosphatidylserine, and phosphatidic acid.

The term "clay" as used herein, are minerals having hydrous aluminium phyllosilicates, sometimes with variable amounts of iron, magnesium, alkali metals, alkaline earths, and other cations found on or near some planetary surfaces. Clay minerals form in the presence of water and have been important to life, and many theories of abiogenesis involve them. Clays are important constituents of soils, and have been useful to humans since ancient times in agriculture and manufacturing.

The term "montmorillonite" as used herein is a very soft phyllosilicate group of minerals that form when they precipitate from water solution as microscopic crystals, known as clay. It is named after Montmorillon in France. Montmorillonite, a member of the smectite group, is a 2:1 clay, meaning that it has two tetrahedral sheets of silica sandwiching a central octahedral sheet of alumina. The particles are plate-shaped with an average diameter around 1 μm and a thickness of 0.96 nm; magnification of about 25,000 times, using an electron microscope, is required to "see" individual clay particles. Members of this group include saponite.

The term Polychlorinated biphenyls (PCBs) as used herein are a group of manmade chemicals. They are oily liquids or solids, clear to yellow in color, with no smell or taste. PCBs are very stable mixtures that are resistant to extreme temperature and pressure. PCBs were used widely in electrical equipment like capacitors and transformers.

The term Dichlorodiphenyltrichloroethane, commonly known as DDT, as used herein is a colorless, tasteless, and almost odorless crystalline chemical compound, an organochlorine, originally developed as an insecticide, and ultimately becoming infamous for its environmental impacts. It was first synthesized in 1874 by the Austrian chemist Othmar Zeidler. DDT's insecticidal action was discovered by the Swiss chemist Paul Hermann Müller in 1939. DDT was used in the second half of World War II to control malaria and typhus among civilians and troops. Müller was awarded the Nobel Prize in Physiology or Medicine "for his discovery of the high efficiency of DDT as a contact poison against several arthropods" in 1948.

The term 1,2,3-Trichloropropane as used herein is a chemical that has been used as a paint or varnish remover, a cleaning and degreasing agent, and was an impurity in certain pesticides. It is also used as a chemical intermediate in the process of making chemicals, such as hexafluoropropylene and polysulfides, and as an industrial solvent.

The term 2,4-Dinitrophenylhydrazine (2,4-DNP), Brady's reagent, Borche's reagent) as used herein is the chemical compound $C_6H_3(NO_2)_2NHNH_2$. Dinitrophenylhydrazine is a red to orange solid. It is a substituted hydrazine, and is often used to qualitatively test for carbonyl groups associated with aldehydes and ketones.

The term AMPA ($\alpha$-amino-3-hydroxy-5-methyl-4-isoxazolepropionic acid) as used herein is a compound that is a specific agonist for the AMPA receptor, where it mimics the effects of the neurotransmitter glutamate. There are several types of glutamatergic ion channels in the central nervous system including AMPA, kainic acid and N-methyl-D-aspartic acid (NMDA) channels. In the synapse, these receptors serve very different purposes. AMPA can be used experimentally to distinguish the activity of one receptor from the other in order to understand their differing functions. AMPA generates fast excitatory postsynaptic potentials (EPSP).

The term Bisphenol A (BPA) as used herein is an organic synthetic compound with the chemical formula $(CH_3)_2C$ $(C_6H_4OH)_2$ belonging to the group of diphenylmethane derivatives and bisphenols, with two hydroxyphenyl groups. It is a colorless solid that is soluble in organic solvents, but poorly soluble in water. BPA is a starting material for the synthesis of plastics, primarily certain polycarbonates and epoxy resins, as well as some polysulfones and certain niche materials. BPA-based plastic is clear and tough, and is made into a variety of common consumer goods, such as plastic bottles including water bottles, sports equipment, CDs, and DVDs.

The term Bisphenol S (BPS) as used herein is an organic compound with the formula $(HOC_6H_4)_2SO_2$. It has two phenol functional groups on either side of a sulfonyl group. It is commonly used in curing fast-drying epoxy resin adhesives. It is a bisphenol, and a close analog of bisphenol A (BPA) in which the dimethylmethylene group $(C(CH_3)_2)$ is replaced with a sulfone group $(SO_2)$.

The term Dibutyl phthalate (DBP) as used herein is an organic compound commonly used plasticizer. With the chemical formula $C_6H_4(CO_2C_4H_9)_2$, it is a colorless oil, although commercial samples are often yellow. Because of its low toxicity and wide liquid range, it is used as a plasticizer.

The term Bis(2-ethylhexyl) phthalate (di-2-ethylhexyl phthalate, diethylhexyl phthalate, DEHP; dioctyl phthalate, DOP) as used herein is an organic compound with the formula $C_6H_4(CO_2C_8H_{17})_2$. DEHP is the most common member of the class of phthalates, which are used as plasticizers. It is the diester of phthalic acid and the branched-chain 2-ethylhexanol. This colorless viscous liquid is soluble in oil, but not in water.

The terms Cation Exchange Capacity (CEC) as used herein is the total capacity of a composition to hold exchangeable cations. CEC is an inherent soil characteristic and is difficult to alter significantly. CEC influences the soil's ability to hold onto essential nutrients and provides a buffer against soil acidification. Soils with a higher clay fraction tend to have a higher CEC. Organic matter has a very high CEC. Sandy soils rely heavily on the high CEC of organic matter for the retention of nutrients in the topsoil.

The term sulfuric acid (alternative spelling sulphuric acid), as used herein is also known as vitriol, is a mineral acid composed of the elements sulfur, oxygen and hydrogen, with molecular formula $H_2SO_4$. It is a colorless, odorless, and syrupy liquid that is soluble in water and is synthesized in reactions that are highly exothermic. The mass fraction of $H_2SO_4$ used in this invention can range from less than 29% to 100%, wherein the mass fraction percentage can be equated by a person with ordinary skill in the art as having many common names (i.e. diluted sulfuric acid, battery acid, fertilizer acid, tower acid, and concentrated sulfuric acid. As an acid, sulfuric acid reacts with most bases to give the corresponding sulfate, which can be modified and used in the instant inventions. At least one embodiment of invention comprises near-saturated-, saturated-, or super-saturated-calcium sulfate anions or variations thereof, and/or complex ions containing calcium, sulfates, and/or variations thereof.

The term acids, or acidic mixtures, as used herein include acidic solution of sparingly-soluble Group IIA complexes ("AGIIS"); adduct having AGIIS, preferably it is the organic acid adduct wherein the organic acid can be propionic acid, lactic acid, or both; sulfuric acid having calcium sulfate dissolved therein, the sulfuric acid can be concentrated sulfuric acid; highly acidic metalated organic acid ("HAMO"); highly acidic metalated mixture of inorganic acid ("HAMMIA"), and a mixture thereof. The acidic, or low pH, solution of AGIIS complexes may have a suspension of very fine particles. The AGIIS has a certain acid normality but does not have the same dehydrating behavior as a saturated calcium sulfate in sulfuric acid having the same normality. In other words, the AGIIS has a certain acid normality but does not char sucrose as readily as does a saturated solution of calcium sulfate in sulfuric acid having the same normality. Further, the AGIIS has low volatility at room temperature and pressure. It is less corrosive to a human skin than sulfuric acid saturated with calcium sulfate having the same acid normality. Not intending to be bound by the theory, it is believed that one embodiment of AGIIS comprises near-saturated, saturated, or super-saturated calcium, sulfate anions or variations thereof, and/or complex ions containing calcium, sulfates, and/or variations thereof.

The term "glyphosate" as used herein is a broad-spectrum systemic herbicide and crop desiccant. It is an organophosphorus compound, specifically a phosphonate, which acts by inhibiting the plant enzyme 5-enolpyruvylshikimate-3-phosphate synthase. It is used to kill weeds, especially annual broadleaf weeds and grasses that compete with crops.

Example 1

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

People, animals and environments can be exposed to mixtures of toxins including: natural and man-made chemicals, microbes, and/or mycotoxins by accident or following natural and/or man-made disasters (i.e. such as extended droughts, flooding, hurricanes, drilling in the wrong place, accidents and other possible catastrophes). Following such disasters, food, feed, water supplies and the environment itself can become contaminated with the toxins. A major challenge associated with these emergencies is the protection of; 1) vulnerable populations and communities located near the site of impact, 2) first responders, and 3) those involved in management and cleanup of the site. Food and water can become contaminated during these events, increasing the risk of exposures to hazardous substances. Thus, the ability to minimize human and animal acute exposures to mixtures of toxins during disaster events is an attractive option.

The instant invention description details how to make and use effective enterosorbents to decrease exposures from mixtures of toxins in animals and humans.

Generally, calcium and sodium montmorillonite clays can be processed using sulfuric acid at 12 and 18 normality, and may also be amended with lecithin. The safety and efficacy of clay based enterosorbent strategies has been confirmed in earlier animal and human clinical trials where montmorillonite clay was included in the diets.

In embodiments, an effective sorbent to sequester and detoxify both mycotoxins is provided by reacting calcium montmorillonite clay with sulfuric acid (0 to 18 normality in increments of 6N). The resulting "acid-processed" clays demonstrate high porosity and high surface area, which results in the effective sorption of both aflatoxin (AfB1) and zearalenone (ZEN). Primary isothermal analyses (not included in the Examples) shows that ZEN adsorption may be the best for clay processed with the highest levels of acid (12N and 18N). An in vivo hydra bioassay further confirmed the ability of the processed clay to protect a living organism from the toxicity of AfB1 and ZEN. This is the first time a clay has been developed with saturable, high binding capacity for ZEN and the ability to effectively bind both AfB1 and ZEN and prevent their toxicity in vivo. Dehydration, de hydroxylation and heat-collapse of the acidic test clays suggested indirectly that AfB1 was primarily adsorbed in the clay interlayer. This confirms earlier work from thermodynamic calculations and a computational model for AfB1 binding onto the interlayer surfaces of calcium montmorillonite. It is postulated that major binding sites for ZEN were on the organophilic porous surfaces of the activated, porous clay structure. These differences in binding sites enhance the non-competitive binding of aflatoxin and ZEN by acid processed clay. The significant protection of hydra from a mixture of 1 ppm AfB1 and 6 ppm ZEN, extrapolated from the ratio (1/6) of the average AfB1 and ZEN concentration in animal feedstuffs, indicated that acidic clays were able to tightly bind aflatoxin and ZEN without major interference. Additionally, preliminary isotherm work suggested that these acid clays may also be capable of binding certain environmental chemicals, suggesting that they can be included in the diet as broad-acting enterosorbents to reduce exposures and toxicity in humans and animals. As per this disclosure, other materials may also be utilized as enterosorbents of important toxins.

The herein disclosed acid clays are able to tightly bind mixtures of potent mycotoxins (e.g., AfB1 and ZEN). During outbreaks and emergencies, the inclusion of these clays in contaminated food and feed may result in decreased bioavailability of the toxins from the gastrointestinal (GI) tract and reduced exposures to humans and animals. The herein disclosed mycotoxin enterosorption technology provides safety and efficacy. In embodiments of this disclosure, acid processed clays can be delivered in water, milled into flour for cooking, added to various snacks, condiments, vitamins, etc. to protect humans and animals from related diseases during acute toxin outbreaks and emergencies.

In embodiments, carbon-like, porous montmorillonite clays are utilized as broad-acting enterosorbents for individual environmental contaminants, microbes, and mycotoxins and/or mixtures of AfB1 and ZEN, for example, during disasters and disease outbreaks. Such montmorillonite clays are safe for human and animal consumption based on numerous interventions and clinical trials.

In embodiments, the parent sorbents are calcium rich montmorillonite clays that have been reported to be safe for consumption by humans and animals, and a sodium rich montmorillonite that is similar to the calcium montmorillonites. To activate the clay, reagent grade sulfuric acid (36 normality) can be utilized to create gradient solutions from 0 to 18N. In embodiments, clay can be stirred in the acidic solutions overnight at 60° C. The slurry can be cooled, centrifuged at 2000 g for 20 min and washed thoroughly with distilled water. This centrifugation-washing process may be repeated (e.g., three times) and the pHs for each group confirmed. Samples may be dried in the oven at 110° C. overnight before grinding and sieving (e.g., through 125 μm) before use.

In embodiments, the herein-disclosed acid processed clays result in saturable, high capacity and tight binding of toxins, such as, without limitation, aflatoxin, ZEN, PCP, BaP, lindane, diazinon, aldicarb, linuron and/or E. coli. It is to be understood that, although described with reference to the binding of particular toxins, binding of other environmental toxins is within the scope of this disclosure.

Without wishing to be limited by theory, it is postulated that certain acid processed clays according to this disclosure will be able to bind various toxins. Still without wishing to be limited by theory, the mechanism of this binding may involve differences in hydrophobicity (logP), capacity, affinity, enthalpy of sorption, charge, size, volume and/or surface area of toxins and clays. LogP refers to the logarithm of the octanol-water partition coefficient. In embodiments, organophilic and amended materials (natural and synthetic) can be utilized to develop a broad-acting sorbent for environmental chemicals, microbes, and mycotoxins. The correlation between critical binding parameters involved in the molecular mechanisms of action can be utilized to tune and adjust acid clay inclusions, as per this disclosure, for a certain toxin or a combination thereof.

Herein Disclosed Enterosorbent. In embodiments, herein disclosed are enterosorbents comprising: a treated sorbent, wherein the treated sorbent comprises a parent sorbent that has been acid or lecithin treated, and wherein the treated sorbent is operable for adsorption of one or more toxins from a gastrointestinal tract of a living being when introduced thereto, such that a bioavailability of and exposure of the living being to the one or more toxins is decreased.
Parent Clays.

In embodiments, the parent sorbent is a phyllosilicate-type mineral comprising: a synthetic phyllosilicate type mineral; a natural phyllosilicate-type mineral; a montmorillonite clay; a sodium montmorillonite clay; a calcium montmorillonite clay; or combination thereof.

One aspect of the present invention pertains to various acidified clays and minerals as a preservative and additive for food and feed. These acidified clays and minerals can function as a food or feed additive that kills, or inhibits the growth of, harmful microorganisms and simultaneously inactivates mycotoxins, such as aflatoxins, present as contaminants in human foods and animal feeds. The clay is an adsorbant having structure-selective affinities to various mycotoxins, such as aflatoxins, thus inactivating the mycotoxins present in human foods and animal feeds. Although not wanting to be bound by theory, the adsorbed or absorbed acid is believed to be available from the acidified clay to kill harmful microorganisms present as contaminants in human foods and animal feeds.

The mineral suitable for this invention include montmorillonite clay, phyllosilicate, Florisil®, bayerite, pseudoboehmite, alumina, silica gel, aluminum oxides, gibbisite, boehmite, and bauxite. The preferred clay used includes hydrated sodium calcium aluminosilicate ("HSCAS") clay.

Another aspect of the present invention relates to a clay of HSCAS with relatively uniform distribution of particle size of less than about 150 microns. Such clay with relatively uniform small particle sizes is particularly suitable for uniform or homogeneous mixing. This clay with uniform distribution of particle size can be obtained, for example, by sifting hydrated sodium calcium aluminosilicate with a 325 mesh screen to separate and eliminate particles having sizes larger than about 45 microns.

The appearance of HSCAS is off white to tan colored and it is a free flowing powder. The free moisture content is about 9%. The loose bulk density is 0.64 g/cc; the packed bulk density is about 0.80 g/cc; and the particle size distribution is about 5% of +100 mesh, 18% of +200 mesh, and 60% of -325 mesh. Chemical analysis showed that % CaO is between 3.2-4.8; % MgO is between 4.0-5.4; % $Fe_2O_3$ is between 5.4-6.5; % $K_2O$ is between 0.50-0.90; % $Na_2O$ is between 0.10-0.30; % MnO is between 0.01-0.03; % $Al_2O_3$ is between 14.8-18.2; and % $SiO_2$ is between 62.4-73.5. Content of traces of heavy metals is as follows: Pb, 6.0-6.5 ppm; As, 0.5-0.7 ppm; Cd, 0.2-0.4 ppm; Cr, 5.5-6.0 ppm, and Hg, less than 0.1 ppm. The clay is substantially free from dioxins (dioxin as used here refers to the toxic contaminant 2,3,7,8-tetrachlorodibenzodioxin ("TCDD") which is used as an index of the presence of dioxins in food ingredient) in HSCAS above the detection limit of 0.33 parts per trillion ("ppt").

In embodiments of this invention, the parent sorbent comprises a montmorillonite clay and wherein the treated sorbent comprises a treated montmorillonite clay. In embodiments, the parent clay comprises a sodium or calcium montmorillonite clay. Although described with reference to clays, in particular montmorillonite clays, it is to be understood that other sorbents (natural or man-made) can be utilized as parent sorbents according to embodiments of this disclosure.

According to embodiments of this disclosure, herein disclosed are acid processed, carbon-like, porous montmorillonite clays which can be utilized as broad-acting enterosorbents for individual toxins and/or mixtures of mycotoxins, environmental chemicals and microbes (e.g., during emergencies and outbreaks). The parent montmorillonite clays are safe for human and animal consumption based on numerous interventions and clinical trials.

In embodiments, the herein disclosed enterosorbent comprises an APM from the parent material of CM or SM. In alternative embodiments, the herein disclosed enterosorbent comprises a parent montmorillonite clay that has been amended with lecithin (lecithin-amended montmorillonite, LAM). Lecithin is a common phospholipid that is amphiphilic. The main commercial sources of lecithin are soybeans, eggs, milk etc. Lecithin possesses a net positive charge at acidic conditions that allows the cation to exchange with clay inorganic cations in the interlayers (Merino, Ollier, Lanfranconi and Alvarez, 2016). Although not wanting to be bound by theory, modification of the parent clay with lecithin at a low pH may attract more hydrophobic environmental chemicals due to the lecithins having lipophilic fatty acid tails.

As per embodiments of this disclosure, broad-acting sorbents for the binding of chemical mixtures can be produced by activating montmorillonites with sulfuric acid to create a highly porous sorbent with high surface area and less trace metals, or creating amphiphilic surfaces with lecithin to facilitate organophilic chemical adsorptions.

The binding parameters of the amended clays determined by equilibrium isotherms, the ability of the herein disclosed amended clays to prevent adverse effects of mycotoxins and environmental toxins as predicted by adult hydra bioassays, and the antibacterial activity with *E. coli* are provided in the Examples hereinbelow. In embodiments, the inclusion of functionalized broad-acting enterosorbents in diets can be utilized as a protective measure to minimize unintended exposures and bioavailability of mycotoxins, chemical contaminants and microbes during disasters.
Toxins.

Figure 1:
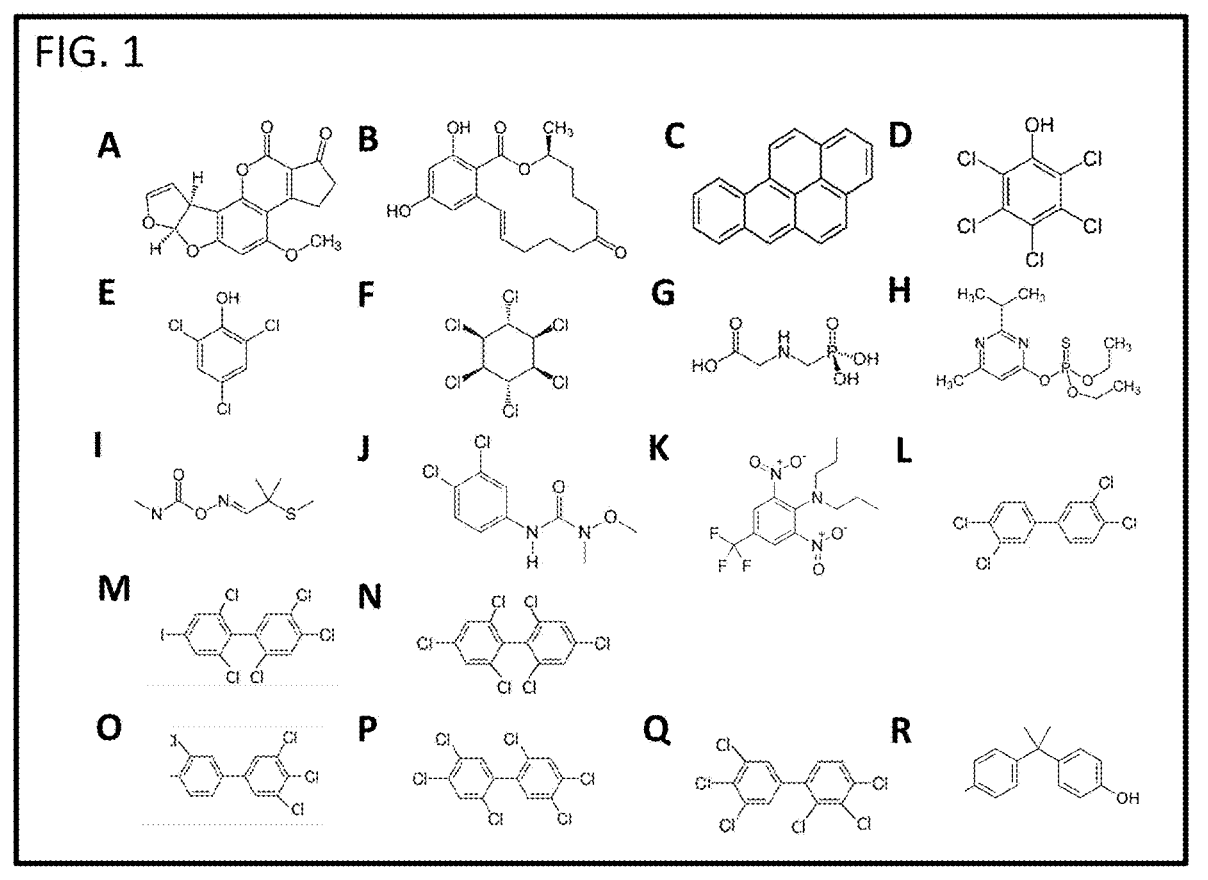

In embodiments, the herein disclosed enterosorbent is effective for the adsorption of one or more toxins selected from mycotoxins, environmental chemicals, and microbes. For example, in embodiments, the one or more toxins are selected from industrial solvents, polycyclic aromatic hydrocarbons (PAHs), pesticides, polychlorinated biphenyls (PCBs), plasticizers or combinations thereof. in embodiments, the one or more toxins are selected from benzo[a] pyrene (BaP), pentachlorophenol (PCP), 2,4,6-trichlorophenol (2,4,6-TCP), lindane, glyphosate, diazinon, aldicarb, linuron, trifluralin, aflatoxin (AfB1), zearalenone (ZEN), PCBs, bisphenol A (BPA), *Escherichia coli* (*E. coli*), or combinations thereof. FIG. 1 shows chemical structures of a few of the toxins the herein disclosed enterosorbents can be effective, including (A) AfB1, (B) ZEN, (C) BaP, (D) PCP, (E) 2, 4, 6-TCP, (F) lindane, (G) glyphosate, (H) diazion, (I) anticarb; (J) Linuron; (K) trifluralin; (L) PCB 77; (M) PCB 126; (N) PCB 153; (0) PCB 157; (P) PCB 154; (Q) PCB 155; and (R) Bisphenol A.
Properties of Herein Disclosed Enterosorbent.

In embodiments, a treated clay enterosorbent of this disclosure tightly binds the one or more toxins, as evidenced by a maximum binding capacity (Qmax) and/or distribution coefficient (Kd) that is greater than or equal to that of conventional carbon material. The herein disclosed enterosorbent adsorbs the one or more toxins via chemical adsorption.

In embodiments, the herein disclosed enterosorbent comprises multiple types of binding sites and/or mechanisms of binding such that the treated sorbent is operable to noncompetitively adsorb AfB1 and ZEN. The multiple types of binding sites can include binding sites in a clay interlayer, which primarily adsorb AfB1, and binding sites of organophilic basal surfaces and edges sites of the treated sorbent, which primarily adsorb ZEN. The enterosorbent can be further operable for the adsorption of bacteria, such as, without limitation, *Escherichia coli* (*E. coli*), as evidenced by a decreased number of microbe colony forming units (CFUs). In embodiments, the enterosorbent is operable to provide a decreased number of microbe colony forming units (CFUs) relative to the parent montmorillonite clays. In embodiments, the enterosorbent is operable to provide a reduction of at least 25, 30, 35, 40, 45, 50, or 55% or more in microbe colony forming units (CFUs) relative to the parent montmorillonite clays.

In embodiments, the herein disclosed enterosorbent exhibits a maximum binding capacity (Qmax) for ZEN that is greater than the Qmax for ZEN of the parent montmorillonite clay. In embodiments, the Qmax of the herein disclosed enterosorbent is at least about 0.2 moles per kilogram (mol/kg). In embodiments, the herein disclosed enterosorbent exhibits an absolute adsorption enthalpy (|ΔHads|) for ZEN (as determined by the Van't Hoff Equation provided hereinbelow) that is greater than the |ΔHads| for ZEN of the parent montmorillonite clay. In embodiments, the |ΔHads| for ZEN of the treated montmorillonite clay is greater than or equal to about 20, 30, 40, 50, 60, 70, 80 or 90 kilojoules per mole (kJ/mol).

In embodiments, the herein disclosed enterosorbent comprises a lecithin treated montmorillonite clay, and is effective for the adsorption of one or more toxins selected from pentachlorophenol (PCP), benzo[a]pyrene (BaP), lindane, aldicarb, diazinon, linuron or combinations thereof. In embodiments, a lecithin treated montmorillonite enterosorbent of this disclosure exhibits increased binding (e.g., as evidenced by an increased maximum binding capacity (Qmax) and/or increased binding affinity (Kd)) relative to the parent montmorillonite clay.

In embodiments, a treated montmorillonite clay enterosorbent of this disclosure has a decreased coefficient of linear expansibility (COLE) in water relative to the parent montmorillonite clay. In embodiments, a treated montmorillonite clay enterosorbent of this disclosure has an increased total surface area and/or porosity relative to the parent montmorillonite clay. In embodiments, a treated montmorillonite clay enterosorbent of this disclosure has a total surface area that is increased by at least 30, 35, or 40% or more relative to the parent montmorillonite clay.

In embodiments, a treated montmorillonite clay enterosorbent of this disclosure comprises a reduced amount of trace metals relative to the parent montmorillonite clay. Such trace metals include, without limitation, aluminum, calcium, sodium. In embodiments, a treated montmorillonite clay enterosorbent of this disclosure exhibits tight binding of lead, such that lead is not dissociated upon introduction of the enterosorbent into the gastrointestinal tract of the living being. In embodiments, a treated montmorillonite clay enterosorbent of this disclosure has a structure that simulates that of activated carbon.

Method of Making Herein Disclosed Enterosorbent.

An enterosorbent of this disclosure may be produced by any suitable methods known in the art. Alternatively, in embodiments, methods of producing sorbents comprising: processing and amending a parent clay to produce activated developed clay. In embodiments, the activating comprises acid treating to produce an acid treated clay via exposure to reagent grade sulfuric acid solution having a concentration (e.g., an equivalent concentration or normality (N)) of greater than or equal to about 6N, 12N, or 18N, or in a range of from about 6N to about 18N or from about 6N to about 12N; and/or lecithin treating to produce a lecithin treated clay via modification with lecithin at 100% cation exchange capacity.

In embodiments, acid treating comprises stirring in the sulfuric acidic solution and lecithin treating comprises stirring in a lecithin solution comprising cations and acid.

Stirring can comprise stirring for at least 5, 6, 7, 8, 9, 10, 11 or 12 h at a stirring temperature. In embodiments, acid treating comprises a stirring temperature that is above room temperature (e.g., about 60° C.), and lecithin treating comprises a stirring temperature about equal to room temperature.

Acid treating can further comprise cooling (e.g., to room temperature), removing from the acidic solution (e.g., via centrifuging), and washing with water (e.g., with distilled water). In embodiments, lecithin treating can further comprise removing from the lecithin solution (e.g., via centrifuging), and washing with water (e.g., with distilled water). The removing and washing (e.g., the centrifuging and washing) can be effective once, or a plurality of times, and/or until a desired pH of the wash water is obtained.

In embodiments, the method of producing an enterosorbent can further comprise drying and sizing the activated clay. Sizing can comprise grinding and sieving to provide an activated clay having a uniform and/or desired size. The desired and/or uniform size can be less than or equal to about 100, 125, or 150 μm, in embodiments. Drying can comprise drying in an oven at a drying temperature and for a drying time. In embodiments, the drying temperature is greater than or equal to about 100, 110, 115, or 120° C., and the drying time is at least 8, 9, 10, 11, or 12 h (e.g., overnight), or a combination thereof.

Without wishing to be limited by theory, during acid treating, interlayer cations may be exchanged with hydrogen protons from the acid, following dissolution of some of the octahedral and tetrahedral sheets in the clay structure, such that the acid treated (or 'processed') clay is an amorphous silica structure with high reactivity and catalytic activity.

In embodiments, lecithin treating is performed subsequent to or simultaneously with acid treating Lecithin treating is performed at low pH (e.g., a pH of less than or equal to about 1, 2 or 3), in embodiments. Again without wishing to be limited by theory, lecithin treating may produce amphiphilic surfaces on the lecithin treated clay.

The herein disclosed method may be tunable to provide a broad acting enterosorbent effective for the adsorption of a variety of toxins, based on chemical properties thereof. For example, the method of producing an enterosorbent may include tuning the treatment of the parent clay, the selection of the parent clay from available parents clays, or a combination thereof based on one or more of the differences in hydrophobicity (logP), capacity, affinity, enthalpy of adsorption (ΔHads), charge, size, volume, and surface area of the one or more toxins and/or available parent clays.

Example 2

The embodiments having been generally described, the following examples are given as particular embodiments of the disclosure and to+ demonstrate the practice and advantages thereof. It is understood that the examples are given by way of illustration and are not intended to limit the specification or the claims in any manner.

Overview.

To develop broad-acting sorbents, both calcium and sodium montmorillonite clays were treated with 12 and 18 normality sulfuric acid to produce high surface area and porosities, similar to activated carbon materials. Based on the herein disclosed results and earlier literature and without wishing to be limited by theory, it is postulated that during the treatment of clays with acid, interlayer cations are initially exchanged with hydrogen protons from the acid, following the dissolution of some octahedral and tetrahedral sheets in the clay structure. The final reaction product of the acid treated clay may be an amorphous silica structure with high reactivity and catalytic activity (Tyagi, B., Chudasama, C. D., & Jasra, R. V., 2006). Certain acid processed montmorillonites have been developed and used extensively for bleaching oils (De, B. K., Patel, J. D., Patel, J. B., Patel, V. K., & Patel, V. R., 2009), removing plant pigments from oils (Yip, A. C., Lam, F. L., & Hu, X., 2005), and sequestering various organic and inorganic contaminants from water during decontamination and purification procedures (Ake, C. L., Mayura, K., Huebner, H., Bratton, G. R., & Phillips, T. D., 2001; Resmi, G., Thampi, S. G., Chandrakaran, S., 2012; Ugochukwu, U. C. & Fialips, C. I., 2017). However, there is no report of acid treated clays for adsorbing mycotoxins and microbes or including them as enterosorbents in animal and human diets for short-term treatment to decrease toxin and microbe exposures.

Cation exchange capacity (CEC) is a measure of a compositions' ability to hold positively charged ions. It is a very important property influencing soil structure stability, nutrient availability, soil pH and the soil's reaction to fertilisers and other ameliorants. The clay mineral and organic matter components of soil have negatively charged sites on their surfaces that adsorb and hold positively charged ions (cations) by electrostatic force. This electrical charge is critical to the supply of nutrients to plants because many nutrients exist as cations (e.g. magnesium, potassium and calcium). In general terms, soils with large quantities of negative charge are more fertile because they retain more cations, however, productive crops and pastures can be grown on low CEC soils.

The main ions associated with CEC in soils are the exchangeable cations calcium ($Ca^{2+}$), magnesium ($Mg^{2+}$), sodium ($Na^+$) and potassium ($K^+$), and are generally referred to as the base cations. In most cases, summing the analysed base cations gives an adequate measure of CEC ('CEC by bases'). However, as soils become more acidic these cations are replaced by $H^+$, $Al^{3+}$ and $Mn^{2+}$, and common methods will produce CEC values much higher than what occurs in the field. This 'exchange acidity' needs to be included when summing the base cations and this measurement is referred to as effective CEC (ECEC). Parent sorbents if the instant invention were modified with lecithin at 100% cation exchange capacity (CEC).

As noted above, to develop effective enterosorbents to decrease exposures from mixtures of toxins (e.g. environmental chemicals, microbes and mycotoxins) in animals and humans, calcium and sodium montmorillonite clays were processed using sulfuric acid at 12 and 18 normality, and (also) these clays were amended with lecithin. In the instant invention, isothermal analyses showed that acid processed montmorillonites (APM) will serve as effective sorbents for numerous toxins. In this report, we include important mycotoxins such as aflatoxin and zearalenone (ZEN), and hazardous environmental chemicals including pentachlorophenol (PCP), benzo[a]pyrene (BaP), lindane, diazinon and aldicarb. An internally developed hydra bioassay further confirmed the safety of clay inclusion in diets and the protective effects against individual toxins or toxin mixtures. Besides the high surface areas, less trace metals and high binding capacities and affinities of APM clays, enthalpy derivations suggest that the sorption process is best defined as a chemisorption involving tight binding of toxin to clay surface. This is the first report of a sorbent (other than carbon) with high binding efficacy for these toxins. Results from dehydroxylated and heat-collapsed clays suggested that AfB1 was primarily adsorbed in the clay interlayer, as predicted from thermodynamic calculations and computational modeling, whereas the major binding sites for ZEN were predicted to be the organophilic basal surfaces and edge sites. This difference in binding sites provides a good opportunity for non-competitive interactions for aflatoxin and ZEN. The protection of hydra against the toxin mixture of 1 ppm AfB1 and 6 ppm ZEN (based on the average AfB1 and ZEN concentration in animal feedstuffs) indicated that APM were able to adsorb aflatoxin and ZEN at the same time with limited interference. Besides chemical adsorption, APMs have been shown to decrease microbe colony forming units, such as E. coli. The APM clays can be delivered (in water, capsules, food, snacks, vitamins, etc.) as broad-acting enterosorbents that will decrease internal exposures to mixtures of hazardous mycotoxins, environmental chemicals and microbes.

Lecithin amended montmorillonite clays (LAM) also showed significantly increased binding for environmental chemicals including PCP, BaP, lindane and aldicarb versus the parent montmorillonite clays from which they were derived. LAM showed high binding capacities and affinities from equilibrium isotherms, suggesting the lecithin clay is broad-acting and can be tunable for a variety of diverse toxins based on differences in their chemical properties.

Isotherm analyses and the hydra bioassay were conducted to evaluate the herein disclosed acid clays. The Langmuir model was derived and plotted by Table-Curve 2D and a computer program using Microsoft Excel was utilized to derive values for the interactions of the toxins with the surfaces of the clays. The results showed a tight binding of both aflatoxin and ZEN without competition and interference.

Calcium montmorillonite was provided by Texas Enterosorbants Inc. Inc. and sulfuric acid was purchased from SIGMA ALDRICH, Chemical Co. Sodium montmorillonite was obtained from the Source Clay Minerals Repository at University of Missouri-Columbia.

Reagents.

High Pressure Liquid Chromatography (HPLC) grade methanol, acetonitrile, reagents and pH buffers (4.0, 7.0 and 10.0) were purchased from VWR (Atlanta, GA). AfB1, ZEN, BaP, glyphosate, trifluralin, aldicarb, linuron, BPA, ammonium acetate, phosphorous pentoxide and other toxins found in FIG. 22 are available form Sigma Aldrich (Saint Louis, MO) and other vendors. Lecithin granules were purchased from Now Foods (Bloomingdale, IL). Activated carbon, PCP, 2,4,6-TCP and sulfuric acid ($H_2SO_4$, 95-98%) were purchased from Aldrich Chemical Co. (Milwaukee, WI). Ethylene glycol and calcium chloride were purchased from Thermo Fisher (Waltham, MA). PCBs (purity>99%) were gifts from Dr. Stephen Safe at Texas A&M University (College Station, TX). Parent clay HSCAS (CM) was obtained from TxESI Corp (Bastrop, TX) and was air classified to have a uniform particle size, wherein the high and low particle size rage cutoffs contain over 90% of the specific sized material. SM was obtained from the Source Clay Minerals Repository at University of Missouri-Columbia. Ultrapure deionized water (18.2 MQ) was generated in the lab using an Elga™ automated filtration system (Woodridge, IL) and used in all experiments.

Synthesis of Sorbents.

Five (5) grams of parent CM and SM (6%, w/v), representing calcium and sodium montmorillonite clays, were taken in glass beakers, and the calculated volume of sulfuric acid was added in each group to derive 12 and 18 normality. A complementary volume of distilled water was added to make a total volume of 83 mL. The solutions were vigorously stirred and kept in an oven at 60° C. overnight. The slurry was cooled, centrifuged at 2000 g for 20 min and washed thoroughly with distilled water. This centrifugation-washing process was repeated multiple times until the pH for each group was constant. All samples were dried in the oven at 110° C. overnight before grinding and sieving through 125 μm before use. These grinding, sieving or air classifying steps were necessary to obtain clay particles of uniform size.

Parent CM sorbents were modified with lecithin at 100% cation exchange capacity (CEC=97 mmol kg$^{-1}$). Calculated amounts of cations and 2 g of parent materials were added in 40 mL of 1 mM HNO$_3$. The suspensions were mixed and stirred for 24 h at ambient temperature, then centrifuged at 2000 g for 20 min and washed with 100 mL distilled water. This centrifugation-washing process was repeated three times. All samples were dried in the oven at 110° C. overnight before grinding and passing through a 125 μm sieve.

To investigate the binding sites for toxins and the importance of intact interlayers, experiments with heat-collapsed sorbents were conducted. Collapsed sorbents were prepared by heating parent and amended sorbents at 200° C. for 30 min and 800° C. for 1 h to collapse the interlayer completely (Grant, P. G., & Phillips, T. D., 1998).

Coefficient of Linear Expansibility in Water.

Sorbent samples were added to the 2 mL mark in graduated cylinders, and then stirred with 15 mL of water. After 24 h following thorough equilibrium hydration and swelling, the final sorbent volume was determined. The ratio calculated from the beginning (2 mL) and final volume is indicative of hydration and expansion of the sample. A higher ratio indicates greater hydration and expansion of the sample (Wang, M. et al., 2017).

Surface Area Determination.

The total surface areas of parent clays and acid treated clays were determined by ethylene glycol (EG). Ethylene glycol is retained on the solid surface at monolayer coverage under an applied vacuum of approximately 0.1 mm Hg (Carter, D. L., Mortland, M. M., & Kemper, W. D., 1986). The surface area was calculated based on the following equation:

$$A = W_a / (W_s \times EG \text{ conversion factor}),$$

wherein A is the total surface area (m$^2$/g), Ws is the oven-dry weight of the clay (g), and Wa is the weight of EG retained by the clay (g). The conversion factor for EG is $3.1 \times 10^{-4}$ g m$^{-2}$.

In vitro isothermal adsorption. The toxin stock solutions were prepared by dissolving pure crystals into acetonitrile. The stock solution was injected into distilled water at pH 7 to yield 8 ppm (8 μg/mL) AfB1, 4 ppm ZEN, 4 ppm PCP, 6 ppm 2,4,6-TCP, 10 ppm glyphosate, 10 ppm diazinon or 5 ppm aldicarb solutions. Other toxin solutions were dissolved into individual mobile phase based on detection methods and lipophilicities to yield 10 ppm BaP (acetonitrile:water, 90:10), 12.5 ppm lindane (acetonitrile:water, 50:50), 20 ppm linuron (acetonitrile:water, 65:35), 20 ppm trifluralin (acetonitrile:water, 70:30), 15 ppm individual PCB congeners (acetonitrile), and 15 ppm BPA (acetonitrile). The maximum concentrations were set based on the octanol-water partitioning coefficients (Kow) so that precipitation was not a factor. Then 0.002% of sorbents were exposed to an increasing concentration gradient of toxin solution. Besides testing samples, there were 3 controls consisting of mobile phase, toxin solution without sorbent and sorbent in mobile phase without toxin. The control and test groups were capped and agitated at 1000 rpm for 2 h at either 24 or 37° C. using an electric shaker. All samples were then centrifuged at 2000 g for 20 min to separate the clay/toxin complex from solution. The UV-visible spectrophotometer was used to scan and read the adsorption peak at 362 nm for AfB1, 236 nm for ZEN, 210 nm for PCP, 294 nm for 2,4,6-TCP, 260.9 nm for PCB 77, 264.5 nm for PCB 126, 207.2 nm for PCb 153 and 154, 280 nm for PCB 154, and 254.9 nm for PCB 157. HPLC with a Phenomenex® lung. 5u C$_{18}$ column (250×4.6 mm) was used to measure the absorption of BaP, lindane and linuron in the supernatant (Challa & Naidu, 2016; Rotenberg, et al., 2011; Sanchez-Martin, et al., 1996). For BaP, a mobile phase of 90% acetonitrile and 10% water at 1.0 mL/min flow rate and an injection volume of 100 μL were set to achieve chemical separation. The fluorescent detector was set with excitation at 264 nm and emission at 412 nm. The detection limit for BaP was 32 ppt. Lindane was separated by 50% acetonitrile and 50% water as the mobile phase at 2.0 mL/min flow rate and 10 μL injection volume, and detected by UV detector at 254 nm wavelength. Breeze software was used to control the HPLC system and collect the data. Separation of linuron was achieved by a mobile phase of 65% methanol and 35% water, a flow rate at 1.0 mL/min, 20 μL injection volume and UV adsorption at 210 nm wavelength. HPLC with a SUPELCOSIL LC-18 column (15×4.6 mm, 3 μm) was used for trifluralin detection in the supernatant. Trifluralin was analyzed using 70% acetonitrile and 30% water as mobile phase at a flow rate of 1.5 mL/min. The column was maintained at 30° C. and the injection volume was 10 μL. Trifluralin detection was programmed at 254 nm wavelength with a UV detector. Breeze® software was used to control the HPLC system and collect data.

Glyphosate, diazinon, aldicarb and BPA concentrations were analyzed using a Waters LC/MS/MS equipped with an Acquity® BEH C18 column (2.1×50 mm). For glyphosate, an Acquity® BEH C18 column (2.1×50 mm, 5 μm) was used for separation and kept at 20° C. A gradient elution using water with 0.1% formic acid (eluent A) and acetonitrile with 0.1% formic acid (eluent B) was carried out at a flow rate of 0.3 mL/min. The gradient program for elution was 5% eluent B (initial) and 5%-100% eluent B (from 0-10 min). Formic acid in the mobile phase was used to promote protonation of the amino group. Injection volume was 10 μL for each analysis. The mass spectrometer was used with an electrospray ionization (ESI) interface and operated in a negative ion mode. The spray voltage was maintained at 4.5 kV. The source temperature was kept at 225° C. The monitored precursor and product ions were m/z 168 to 63 and 81. For diazinon and aldicarb, the column temperature was kept at 35° C. A gradient elution using 10 mM NH$_4$OAc in water (elute A) and 10 mM NH$_4$OAc in methanol (elute B) was carried out (elute B, 10%-90% linear gradient for 8 min) at a flow rate at 0.6 mL/min. Sample volumes of 5 μL were used for each analysis. The mass spectrometer was performed with an electrospray ionization (ESI) interface and operated in a positive ion mode. The spray voltage was maintained at 5 kV. Nitrogen gas was used as the collision gas and curtain gas, and argon gas was used as the nebulizer gas and heater gas. The source temperature was kept at 500° C. The mass spectrometer was operated under multiple reaction monitoring (MRM) mode and the monitored precursor and product ions were m/z 305.1 to 169.2 for diazinon and 208.2 to 116.1 for aldicarb. For BPA detection, a 1.5 min linear gradient was used from 10-100% acetonitrile in water followed by a hold at 100% acetonitrile for 0.4 min at a flow rate of 0.4 mL/min. The total run time, including equilibration, was 3.5 min. The column oven temperature was 45° C., and the injection volume was 5 µL. Negative ion electrospray mass spectrometry with selected reaction monitoring (SRM) and a dwell time of 50 ms per transition was used for the measurement of each analyte. The SRM transitions were m/z 227 to 212 (quantifier) and m/z 227 to 133 (qualifier). The unit mass resolution was used for ion mass analyzers. The EPI scan rate was 1000 amu/s, and the scan range was 106 to 396 amu. Empower analyst software was used to control the LC/MS/MS system and acquire the data. The limits of detection (LOD) for each toxin were 500 ppb for PCP and 2,4,6-TCP, 5 ppb for lindane and linuron, 12.5 ppb for diazinon and aldicarb, 0.1 ppb for trifluralin, 0.5 ppb for glyphosate and 10 ppb for BPA, with excellent reproducibility and sensitivity of the detection methods Standard toxin solutions were spiked before and after 2 hr of agitating and the relative standard deviations (RSD) were <5%, showing high recovery percentage and limited nonspecific binding. The detection methods were validated using standard calibration curves Standard solutions of each toxin were individually prepared in mobile phase at concentration gradients between 25 ppm and 0.1 ppm to plot the standard curves. The standard curves of all toxins were linear (r2>0.99) between signal intensity and toxin concentration. Data Calculations and Curve Fitting.

Samples were prepared in triplicate and quantified using standard calibration curves. Therefore, the toxin concentration in solution (x-axis) detected by HPLC and LC/MS/MS was calculated from peak area at the toxin retention time. Whereas the absorption data achieved by UV-visible spectrophotometer were used to calculate the concentration of toxin left in solution (c) by Beer's law. The amount adsorbed for each data point (y-axis) was calculated from the concentration difference between test and control groups. More specifically, the y-axis is the amount of toxin bound by sorbents (in mol/kg). It is calculated by the difference in moles of free toxin in the test solution versus control groups and is then divided by the mass of the clays included.

$$\text{Absorbance} = (E) \times (L) \times (c) \qquad \text{Beer's law}$$

wherein e is the molar extinction coefficient ($\varepsilon$ for AfB1=21,865 cm-1mol-1, e for ZEN=24,833 cm-1mol-1, e for PCP=73,400 cm$^{-l}$mol$^{-1}$), L is the path length of the cell holder=1 cm, dependent on the cuvette.

These data were then plotted using Table-Curve 2D and a computer program that was developed with Microsoft Excel to derive values for the variable parameters. The best fit for the data was a Langmuir model, which was used to plot equilibrium isotherms from triplicate analysis. The isotherm equation was entered as user-defined functions:

$$q=Q\text{max}(KdCw1+KdCw)q=Q\text{max}(KdCw1+Kd\text{Cw}) \quad \text{Langmuir model (LM)}$$

wherein q=toxin adsorbed (mol/kg), Qmax=maximum capacity (mol/kg), Kd=distribution constant, Cw=equilibrium concentration of toxin.

The plot will normally display a break in the curve. The value on the x-axis where the curve breaks is an estimate of Kd-1. The value on the y-axis where the curve breaks is an estimate of Qmax. The Qmax is taken from the fit of LM to the adsorption data. [0023] The definition of Kd is derived from the Langmuir equation giving:

$$Kd=q(Q\text{max}-q)Cw$$

The enthalpy ($\Delta$Hads) was calculated by comparing the difference of Kd values at 24 and 37° C. by the following equation:

$$\Delta Hads=-R \ \ln(Kd2Kd1)1T2-(1T1)\Delta Hads=-R$$
$$\ln(Kd2Kd1)1T2-(1T1) \qquad \text{Van't Hoff equation}$$

$R$ (ideal gas constant)=8.314 J/mol/K, $T$=absolute temperature (K).

Hydra Assay.

Hydra vulgaris were obtained from Environment Canada (Montreal, Qc) and maintained at 18° C. The hydra classification method (Wilby, O. K., Tesh, J. M., & Shore, P. R., 1990) was used with modification to rate morphology of the adult hydra as an indicator of solution toxicity. The illustration of this classification is indicated in FIG. 2. In this assay, the scoring of hydra morphology is objective and repeatable with representation in detail in previous literature. The assay included monitoring times at shorter intervals during the first two days (0, 4, 20, and 28 h) and 24 h intervals for the last three days (44, 68, and 92 h). Solutions were not changed during testing. The hydra morphological response was scored and recorded after exposure of toxin with and without sorbent treatment. Mature and non-budding hydra in similar sizes were chosen for testing in order to minimize differences between samples. Controls for this experiment included hydra media. Sorbent inclusion percentage was chosen based on previous studies (Brown, K. A. et al., 2014; Marroquin-Cardona, A. et al., 2011; Phillips, T. D. et al., 2008). Toxin treatment groups included 3 ppm BaP with a metabolism activation package (MAP) in 1% DMSO, 20 ppm AfB1, 4 ppm ZEN, 2 ppm PCP, 30 ppm glyphosate, 1 ppm aldicarb, 5 ppm trifluralin, or a pesticide mixture (2 ppm PCP, 2,4,6-TCP, lindane, diazinon, glyphosate, trifluralin, aldicarb and linuron), 20 ppm PCB 77, 126 and 153, 20 ppm Aroclor 1254 and 1260 in hydra media based on the minimum effective dose (Khalaf, S. et al., 2013) that caused 100% mortality in 92 h. MAP was standardized and consisted of 2.4 µg/mL mice hepatic microsomal cytochrome P450, 225 µM NADPH and 25 µM MgCl2 (Newman, Johnson, Giacobbe, & Fu, 1990; Ottinger et al., 1999). Toxin mixture treatment groups included 1 ppm AfB1 and 6 ppm ZEN based on the ratio of average concentrations of AfB1 and ZEN in animal feedstuffs (Murugesan, G. R. et al., 2015). All test solutions were capped and prepared by shaking at 1000 rpm for 2 h and centrifugation at 2000 g for 20 min prior to exposure of hydra in the Pyrex dishes (Brown, K. A. et al., 2014). For each sample, three hydra were included into 4 mL of test media and kept at 18° C. The score or average toxicity rating was determined by calculating the average score for morphological changes for a certain group at a specific time point.

Statistical Analysis.

A one way t-test was used to calculate statistical significance. Each experiment was independently triplicated to derive an average and standard deviation. In the t-test, the average COLE ratio from COLE experiments, Qmax from equilibrium isothermal analyses and toxicity scores from the hydra assay were included to calculate D=control-test groups and D2. Then the t-value was calculated using the following equation (N=3):

$$t = \frac{(\Sigma D)/N}{\sqrt{\dfrac{\Sigma D^2 - \left(\dfrac{(\Sigma D)^2}{N}\right)}{(N-1)(N)}}}$$

The t-value and DF (degrees of freedom) were compared in a p-value table to determine the statistical significance. Results were considered significant at P<0.05.

FIG. 2 is a depiction of the hydra morphology scale by Wilby (1988): The scale is graded from 0-10, where 10 represents a normal living hydra and 0 represents a disintegrated hydra. The physiologic conditions of hydra were assessed with a dissecting microscope.
Coefficient of Linear Expansibility in Water.

The COLE ratio indicates the expansibility of sorbents in water. COLE=expansion volume of clay/original volume of clay. The higher the ratio, the more expansion and hydration of the sample. The accuracy of this experiment was confirmed by the COLE values of CM and SM clays, which predicted calcium-rich and sodium-rich montmorillonite, respectively (FIG. 3).

SM is a sodium montmorillonite with high expansibility as indicated by its COLE ratio. CM, on the other hand, is a calcium montmorillonite with limited expansibility in water. The process of acid treatment results in the leaching of substituted interlayer cations, which have high hydration energy to attract water molecules into the interlayer, by replacing with $H^+$ ions from acid (Tyagi, B., Chudasama, C. D., & Jasra, R. V., 2006). This possibly explains the decrease in COLE values of acid processed clays, compared to the parent clays. This restriction of expansibility in water and stabilization of clays indicates the exchange and leaching out of cations and the creation of porous and high surface area of the APM structure.

FIG. 3 shows the coefficient of linear expansibility (COLE) for sorbents in water. The COLE value for parent SM indicated significant hydration and expansibility, whereas COLE values for acid processed sodium montmorillonite displayed limited or decreased hydration energy and expansibility compared to parent SM. The parent CM and acid processed calcium montmorillonite derived limited expansibility in water.
Surface Area.

Figure 4:
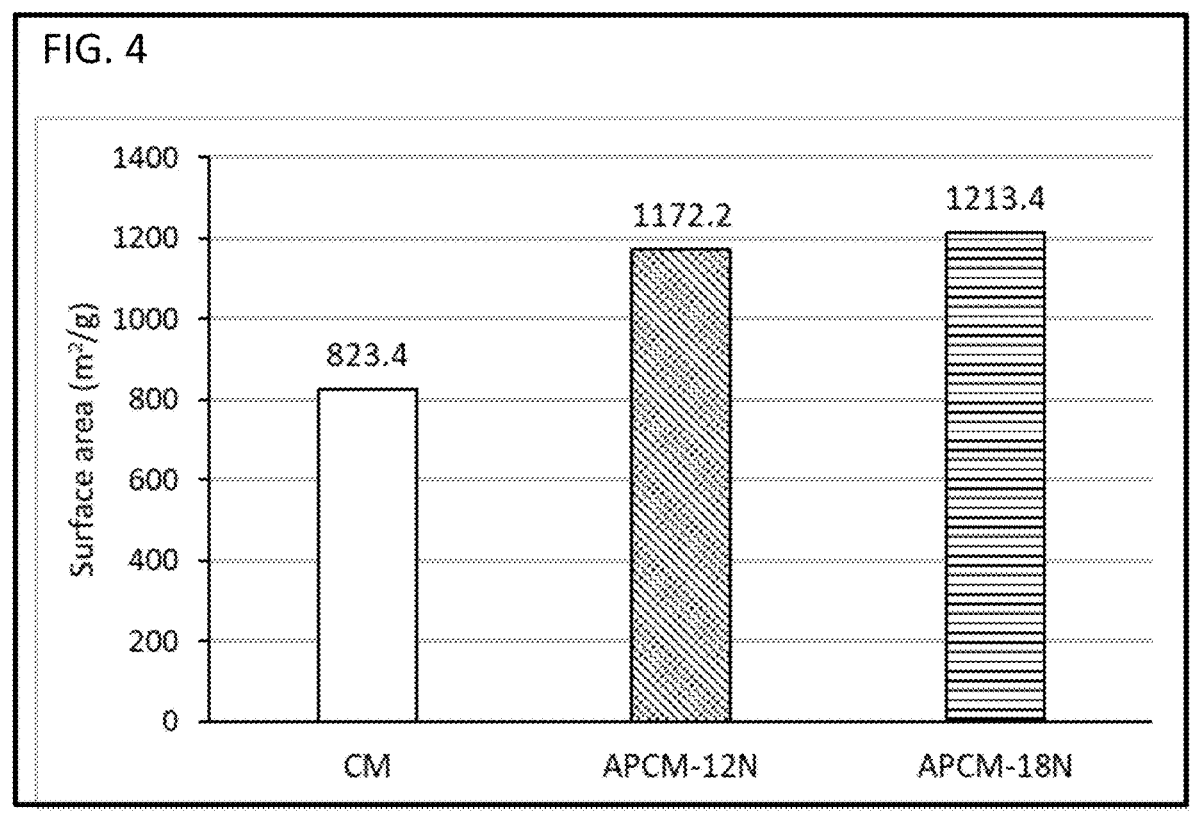
FIG. 4 shows the surface area in square meters per gram of parent calcium montmorillonite (CM) and acid processed montmorillonites (APM) determined by ethylene glycol (EG) absorbance onto the enterosorbent surfaces.

Acid processed montmorillonites were found to have higher total surface areas of 1172.2 $m^{-2}$ g (APCM-12N) and 1213.4 $m^{-2}$ g (APCM-18N), indicating a 42.4% and 47.4% increase compared to the parent CM clay, as shown in FIG. 4. This high surface area and porosity is probably achieved by leaching out cations in the interlayer and di-octahedral sheets and replacing them with protons, resulting in a higher chance of broad-acting enterosorbent development. The consistency of this method is confirmed by similar results with parent CM determined previously. FIG. 4 shows the surface area of parent montmorillonite and APM determined by ethylene glycol (EG) absorbance onto the clay surfaces.
Trace Metals.

Figure 5:
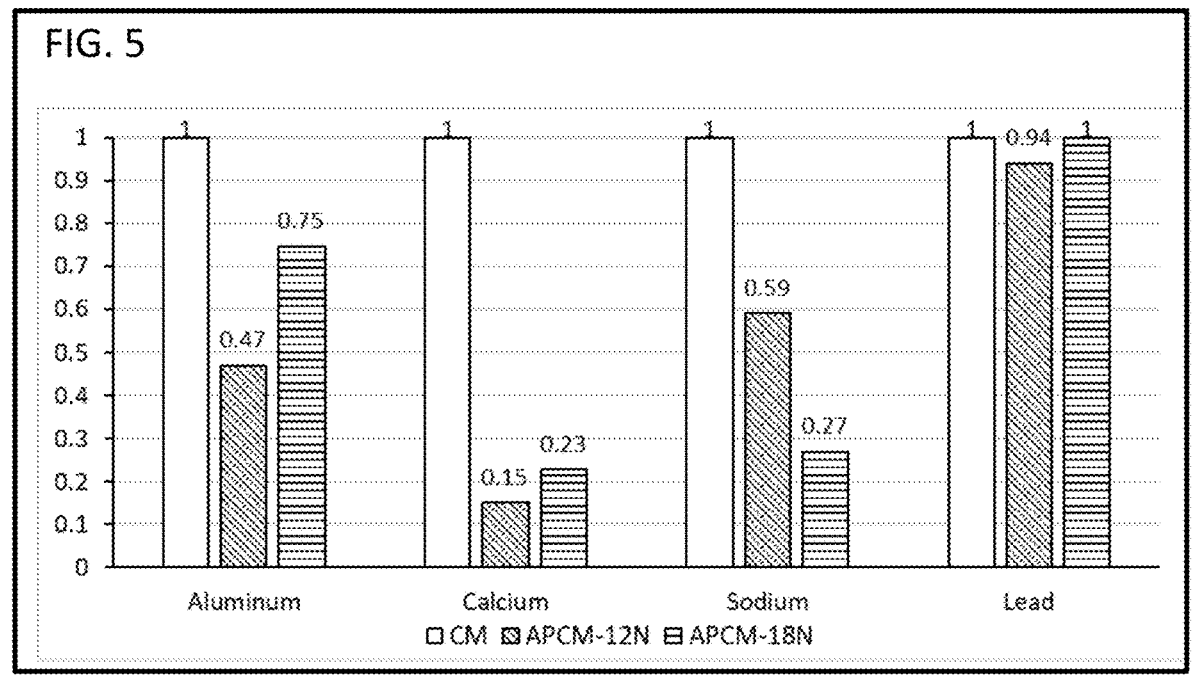
FIG. 5 shows the relative values of trace metals in acid processed montmorillonites (APM) compared to the parent enterosorbent.

Trace metals in parent and acid treated CM were analyzed by ALS Environmental (Kelso, WA). Calcium is the primary interlayer cation, while aluminum and sodium are present primarily in the interlayer as well as in di-octahedral and tetrahedral sheets. The results in FIG. 5 show that both acid treatments decreased relative values of aluminum, calcium and sodium compared to the parent clay. Treatment with 12N decreased aluminum and calcium more significantly and 18N decreased sodium more significantly. This result indicates that lower acid concentration (12N), firstly leaches out cations in the interlayer and octahedral sheets, whereas higher acid concentration (18N) replaces cations in the tetrahedral sheets that are less reactive. This is also in alignment with an FTIR report on acid clays (Tyagi, B. et al., 2006).

The lead level in one parent clay was detected as 11.7 ppm (relative value was adjusted to 1), which is slightly higher than the action level set by the Food and Drug Administration (FDA) as 10 ppm. The results showed that lead concentration was not changed by sulfuric acid treatment for 24 h at high temperature, nor other treatments including sonication and washing with citric acid (data not shown). The stable and consistent concentration of lead indicates that lead is tightly bound in the clay structure, and is not easily dissociated even in extreme conditions such as heat, strong acid and sonication for long durations. Thus, lead should not be available in the animal or human stomach upon ingestion of clay. Earlier intervention studies in animals and clinical trials in humans carried out by the inventors support this conclusion. FIG. 5 shows the relative values of trace metals in APM compared to the parent clay.
Isothermal Adsorption and Hydra Assay on Mycotoxins.

Equilibrium isotherms were generated by Table-Curve 2D and a computer program developed in the laboratory using Microsoft Excel to derive affinities (Kd), capacities (Qmax) and the enthalpy (ΔH) of sorption for toxin-surface interactions. Each point represents the values calculated for toxin bound to clay (mol/kg) and toxin left in solution (mol/L) for the corresponding 11 dilutions.
Dioxin.

The amount of dioxin present in the parent CASAD clay containing a variety of particle sizes and the amount of dioxin present in CASAD clay after being sized to contain only particles less than 80 microns was measured as previously described. Prior to sizing, the CASAD clay contained the amounts of dioxin shown in Table 1 below.

TABLE 1

| Analyte | Concentration Found (pg/L) | Detection Limit (pg/L) |
|---|---|---|
| 2,3,7,8-TCDD | — | 0.024 |
| 1,2,3,7,8-PeCDD | — | 0.025 |
| 1,2,3,4,7,8-HxCDD | — | 0.039 |
| 1,2,3,6,7,8-HxCDD | — | 0.044 |
| 1,2,3,7,8,9-HxCDD | — | 0.042 |
| 1,2,3,4,6,7,8-HpCDD | 0.121 | 0.043 |
| OCDD | 1.243 | 0.108 |
| Total Tetra-Dioxins | 1.284 | 0.024 |
| Total Penta-Dioxins | 1.820 | 0.025 |
| Total Hexa-Dioxins | 1.994 | 0.039 |
| Total Hepta-Dioxins | — | 0.043 |

As shown in Table 1, CASAD clay prior to sizing contained 0.121 pg/L of heptachlorodibenzo-p-dioxin (1,2,3,4,6,7,8-HpCDD) and 1.243 pg/L of octachlorodibenzo-p-dioxin (OCDD). In addition, the total tetrachlorodibezodioxins were measured at 1.284 pg/L, the total pentachlorodibenzodioxins were measured at 1.820, and the total hexachlorodibenzodioxins were measured at 1.994. The other dioxins tested were either absent or at a level below the detection limit of the testing apparatus. The CASAD clay was then sized so that it contained only particles less than 80 microns in size. The same analysis of dioxin content was performed. The results are shown in Table 2 below.

TABLE 2

| Analyte | Concentration Found (pg/L) | Detection Limit (pg/L) |
|---|---|---|
| 2,3,7,8-TCDD | — | 0.024 |
| 1,2,3,7,8-PeCDD | — | 0.025 |
| 1,2,3,4,7,8-HxCDD | — | 0.039 |
| 1,2,3,6,7,8-HxCDD | — | 0.044 |
| 1,2,3,7,8,9-HxCDD | — | 0.042 |
| 1,2,3,4,6,7,8-HpCDD | — | 0.043 |
| OCDD | 0.362 | 0.108 |
| Total Tetra-Dioxins | — | 0.024 |
| Total Penta-Dioxins | — | 0.025 |

TABLE 2-continued

| Analyte | Concentration Found (pg/L) | Detection Limit (pg/L) |
|---|---|---|
| Total Hexa-Dioxins | — | 0.039 |
| Total Hepta-Dioxins | — | 0.043 |

The results show that dioxin content is greatly reduced in CASAD clay having a particle size less than 80 microns. The only remaining detected dioxin was octachlorodibenzodioxin (OCDD), at a reduced amount of 0.362 pg/L.

FIG. 6A and FIG. 6B show the AfB1 isothermal plot on acid processed calcium montmorillonite (APCM) (FIG. 6A) and acid processed sodium montmorillonite (APSM) (FIG. 6B). The $r^2$ values (>0.8) for the Langmuir model and curved shapes indicate that AfB1 binds tightly onto clay surfaces and does not dissociate easily. The derived Qmax indicating that acid processed CM and SM were able to maintain aflatoxin adsorption with similar binding curves and capacity compare to the parent clays. Based on previous studies, sorbents with high expansibility in water (high COLE value) have slightly lower Kd values for APSM-12N and APSM-18N. The decreased Kd values were associated with the restriction of expansibility for the acid treated sodium montmorillonites.

FIG. 6A and FIG. 6B show Langmuir plots of AfB1 on APCM (FIG. 6A) and APSM (FIG. 6B) versus parent montmorillonites showing the observed and predicted Qmax values at pH 6.5. The Qmax values indicated tight binding. (FIG. 6A) CM: Qmax=0.37; Kd=1E6; APCM-12N: Qmax=0.34; Kd=1E6; APCM-18N: Qmax=0.37; Kd=8E5. (FIG. 6B) SM: Qmax=0.3; Kd=2E7; APSM-12N: Qmax=0.29; Kd=6E6; APSM-18N: Qmax=0.27; Kd=2E6.

Figure 7A:
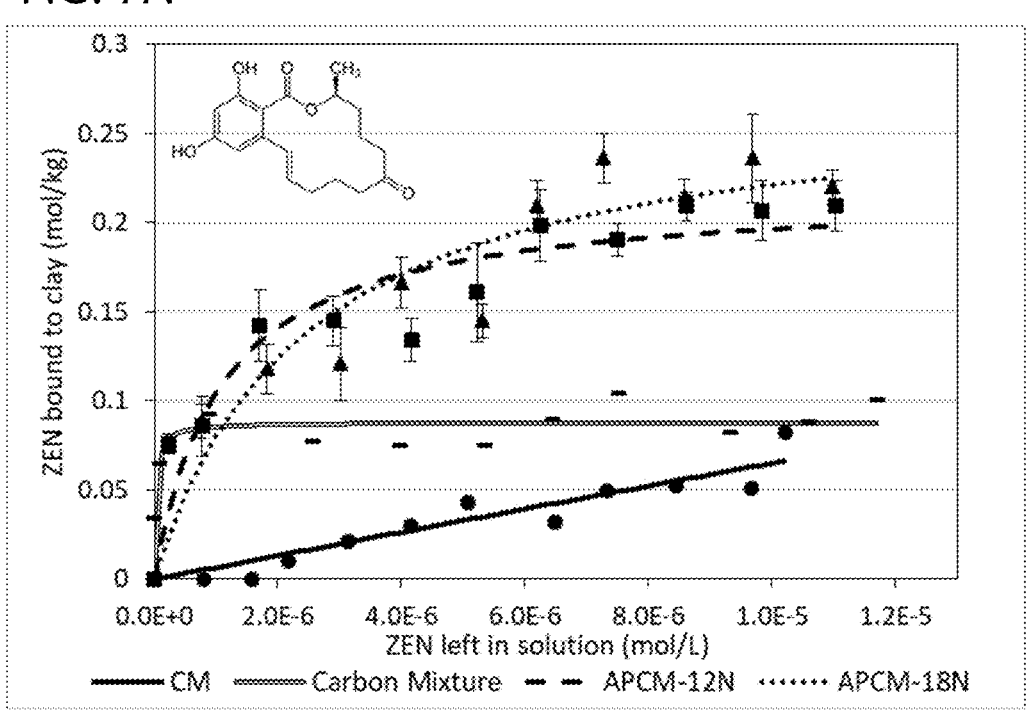
FIG. 7A and FIG. 7B show Langmuir plots of ZEN on acid processed calcium montmorillonites (APCM) (FIG. 7A) and acid processed sodium montmorillonites (APSM) (FIG. 7B) versus the parent montmorillonites and a carbon mixture showing the observed and predicted Qmax values at pH 6.5; Carbon mixture: Qmax=0.09; Kd=4E7; APCM-12N: Qmax=0.22; Kd=1E6; APCM-18N: Qmax=0.28; Kd=4E5. APSM-12N: Qmax=0.21; Kd=6E6; APSM-18N: Qmax=0.24; Kd=2E6.
Figure 7B:
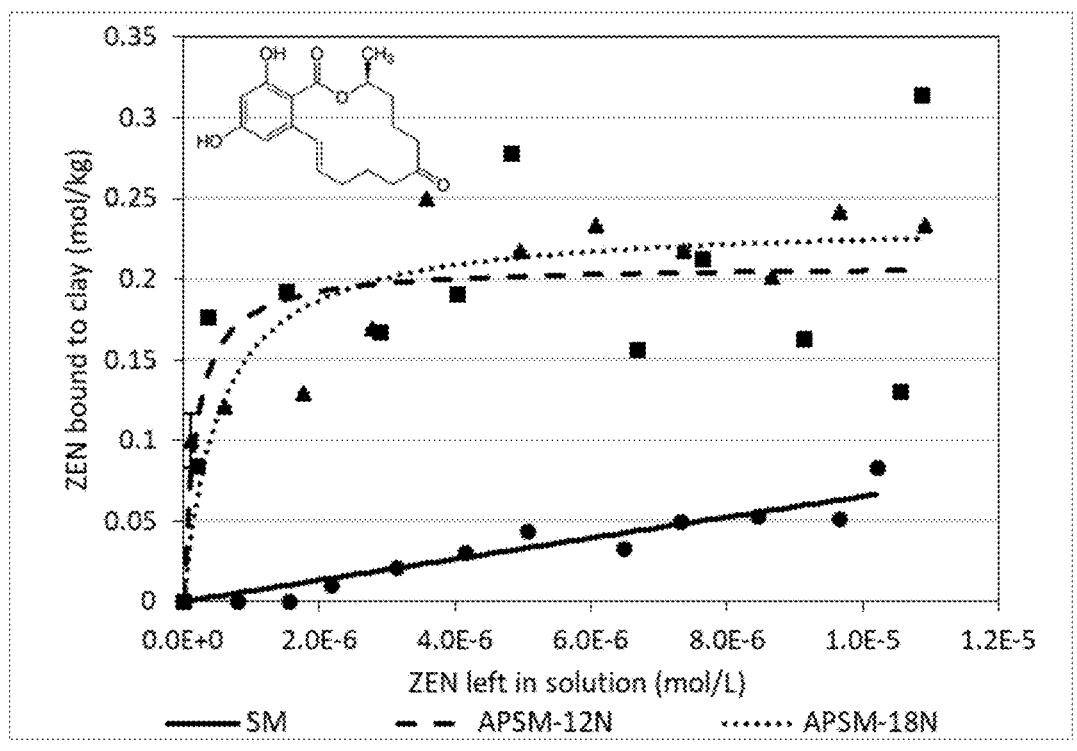

For ZEN adsorption in FIG. 7A and FIG. 7B, the parent CM as well as multiple organoclays showed a Freundlich trend, indicating toxins are partitioning on the sorbent surface rather than tightly binding. A carbon included mixture displayed a curved adsorption shape that fitted the Langmuir model with a binding capacity of 0.09 mol/kg. All the APM improved ZEN binding with a curve shape that fits the Langmuir model, indicating saturable binding sites and tight binding onto the APM surfaces. The APM binding capacities (Qmax>0.2) were significantly higher than that of a carbon mixture. This is the first time a sorbent material other than a carbon related material has been developed to adsorb ZEN effectively and tightly.

FIG. 7A and FIG. 7B show Langmuir plots of ZEN on APCM (FIG. 7A) and APSM (FIG. 7B) versus parent montmorillonites and a carbon mixture showing the observed and predicted Qmax values at pH 6.5. The Qmax values indicated tight binding. (FIG. 7A) Carbon mixture: Qmax=0.09; Kd=4E7; APCM-12N: Qmax=0.22; Kd=1E6; APCM-18N: Qmax=0.28; Kd=4E5. (FIG. 7B) APSM-12N: Qmax=0.21; Kd=6E6; APSM-18N: Qmax=0.24; Kd=2E6.

Figure 8A:
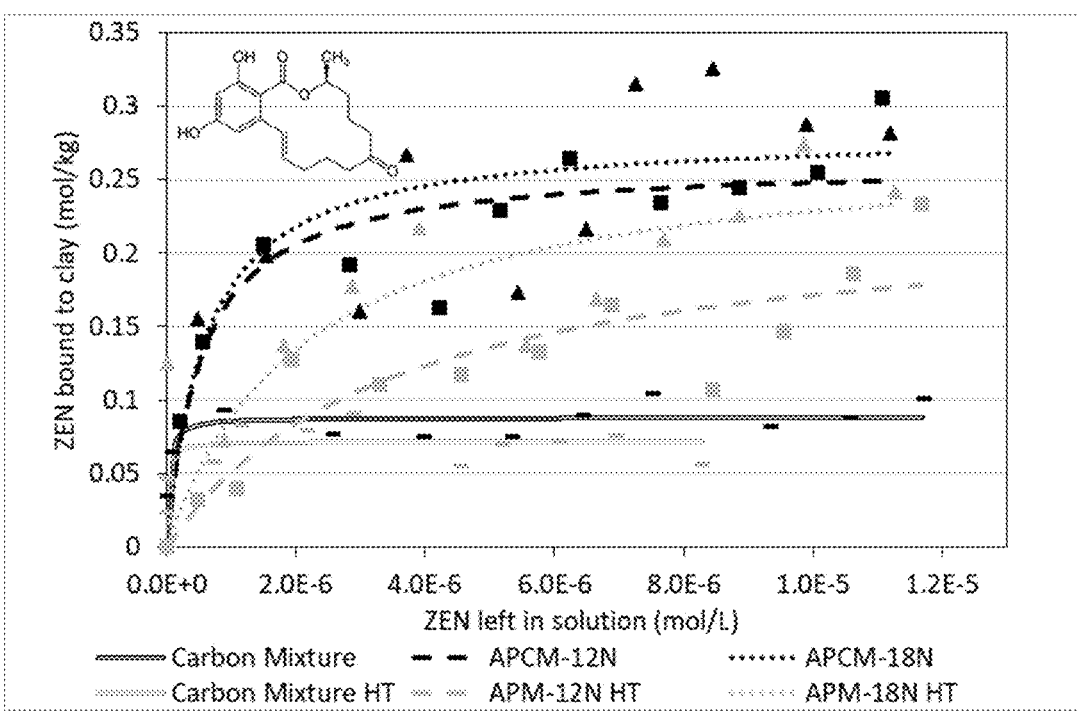
FIG. 8A and FIG. 8B show Langmuir plots of ZEN on APCM (FIG. 8A) and APSM (FIG. 8B) and a carbon mixture at 24 and 37° C. (HT); Carbon mixture: Qmax=0.09; Kd=4E7; Carbon mixture HT: Qmax=0.07; Kd=5E7; APCM-12N: Qmax=0.22; Kd=1E6; APCM-12N HT: Qmax=0.23; Kd=4E5; APCM-18N: Qmax=0.28; Kd=4E5; APCM-18N HT: Qmax=0.28; Kd=5E5. APSM-12N: Qmax=0.21; Kd=6E6; APSM-12N HT: Qmax=0.15; Kd=2E6; APSM-18N: Qmax=0.24; Kd=2E6; APSM-18N HT: Qmax=0.14; Kd=3E6.
Figure 8B:
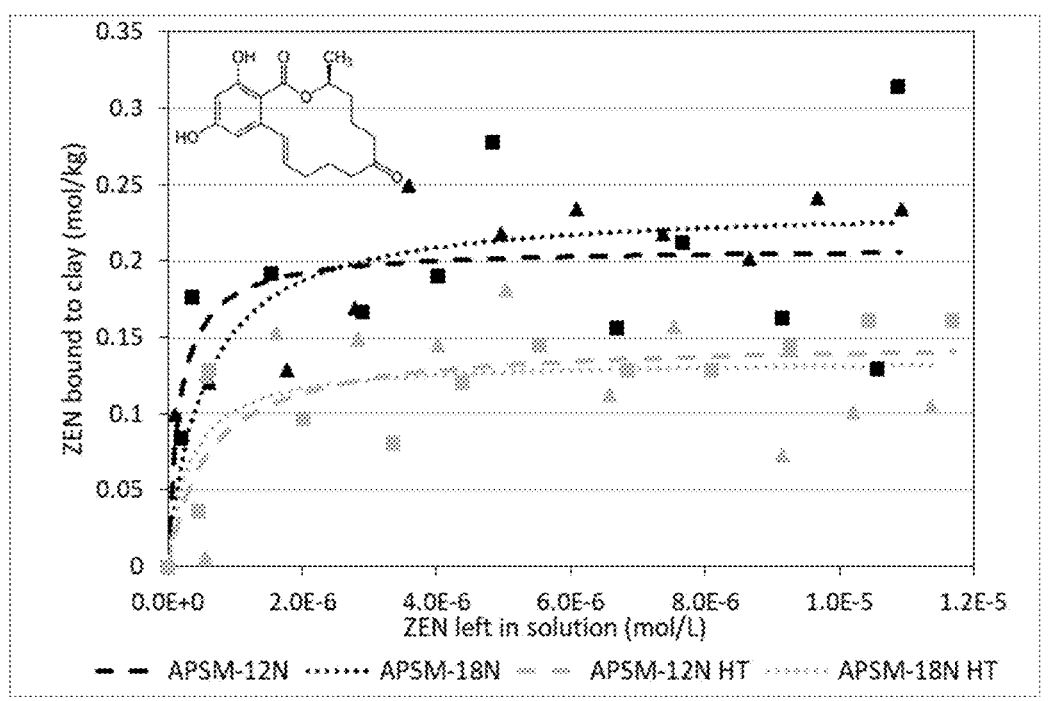

To calculate the enthalpy of APM, isotherms on ZEN were conducted at 24 and 37° C., as shown in FIG. 8A and FIG. 8B. After applying individual Kd values at different temperatures into the enthalpy equation, the calculated enthalpies were ΔHAPCM-12N=−90 kJ/mol; ΔHAPCM-18N=−75 kJ/mol; ΔHAPSM-12N=−74 kJ/mol; ΔHAPSM-18N=−78 kJ/mol; ΔHCarbon Mixture=−20 kJ/mol.

Since all the absolute enthalpy values for APM were above 20 kJ/mol, this indicates that the binding reaction involves a chemisorption mechanism (instead of a physisorption mechanism) that favors tight and relatively irreversible bindings.

FIG. 8A and FIG. 8B show Langmuir plots of ZEN on APCM (FIG. 8A) and APSM (FIG. 8B) versus parent montmorillonites and a carbon mixture at 24 and 37° C. (HT). (FIG. 8A) Carbon mixture: Qmax=0.09; Kd=4E7; Carbon mixture HT: Qmax=0.07; Kd=5E7; APCM-12N: Qmax=0.22; Kd=1E6; APCM-12N HT: Qmax=0.23; Kd=4E5; APCM-18N: Qmax=0.28; Kd=4E5; APCM-18N HT: Qmax=0.28; Kd=5E5. (FIG. 8B) APSM-12N: Qmax=0.21; Kd=6E6; APSM-12N HT: Qmax=0.15; Kd=2E6; APSM-18N: Qmax=0.24; Kd=2E6; APSM-18N HT: Qmax=0.14; Kd=3E6.

Figure 9A:
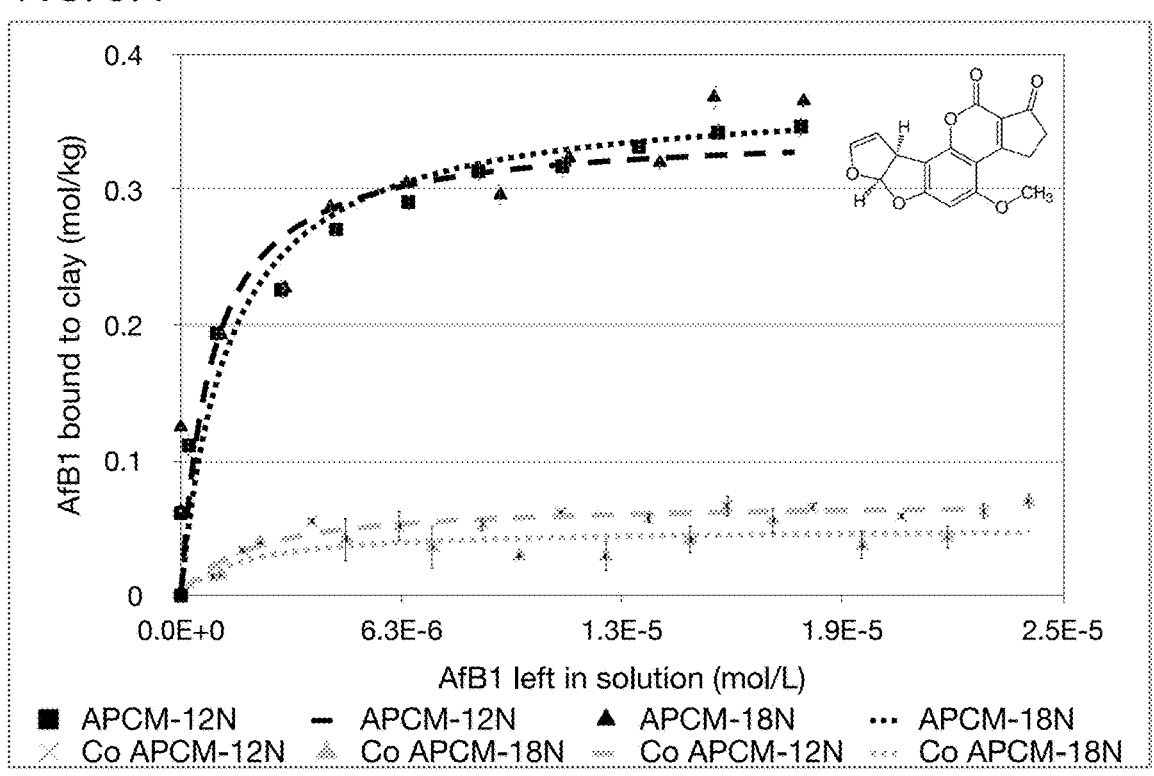
FIG. 9A and FIG. 9B show Langmuir plots of AfB1 (FIG. 9A) and ZEN (FIG. 9B) on collapsed (Co) APCM-12N and APCM-18N at pH 6.5.
Figure 9B:
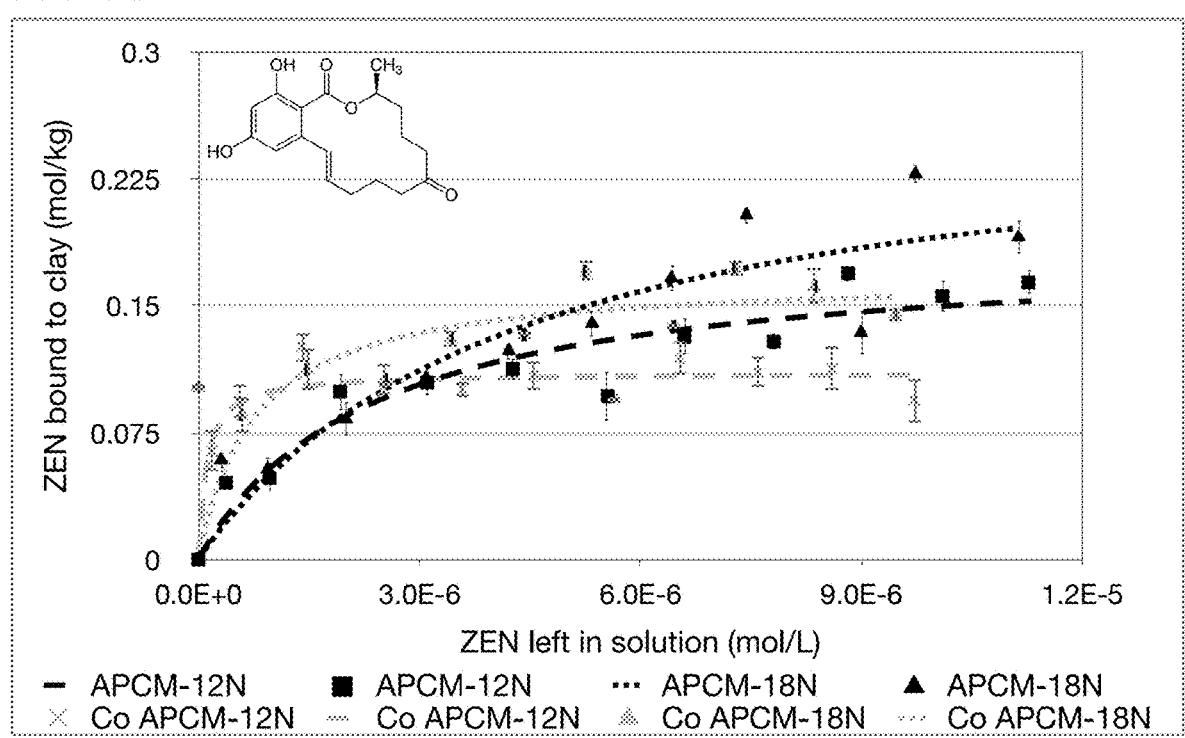

After heating at 800° C., the interlayers of APM were dehydroxylated and collapsed. FIG. 9A and FIG. 9B shows that binding capacities on AfB1 of collapsed APM are significantly reduced, with 20% and 14% of aflatoxin bound remaining on collapsed (co) APCM-12N and APCM-18N, respectively. This dramatic decrease of AfB1 suggests (indirectly) that most of the AfB1 binds within the interlayer of these clays and only minor amounts bind on the edges and basal surfaces. On the other hand, the percentages of the remaining ZEN bound were calculated as 50% and 63% for collapsed APCM-12N and APCM-18N, respectively. Thus, the primary binding sites for ZEN were shown to be the more organophilic basal surfaces and edge sites, which were not affected during the heat. This difference in binding sites and mechanisms provided a good possibility that APM can serve as a broad-acting enterosorbent for toxin mixtures of aflatoxin and ZEN.

FIG. 9A and FIG. 9B show Langmuir plots of AfB1 (FIG. 9A) and ZEN (FIG. 9B) on collapsed APCM-12N and APCM-18N at pH 6.5. (FIG. 9A) APCM-12N: Qmax=0.34; Kd=1E6; APCM-18N: Qmax=0.37; Kd=8E5; Co APCM-12N: Qmax=0.07; Kd=5E5; Co APCM-18N: Qmax=0.05; Kd=6E5. (FIG. 9B) APCM-12N: Qmax=0.21; Kd=6E6; APCM-18N: Qmax=0.24; Kd=2E6; Co APCM-12N: Qmax=0.11; Kd=9E6; Co APCM-18N: Qmax=0.17; Kd=1E7.

The protective roles of parent and amended clays were identified using the adult hydra assay. The minimal effective concentrations (MECs) for AfB1 and ZEN were established at 20 ppm and 4 ppm, which result in 100% hydra mortality in 92 h. With the inclusion of parent CM and APCM clays at 0.0005% inclusion level, adult hydra were protected completely from aflatoxin toxicity. Similarly, APCM rendered a significant protection for hydra against ZEN at the 0.01% level, resulting in morphologic ratings no different from the hydra media control group, whereas no protection of parent CM at the same level was shown against ZEN in FIG. 10A, FIG. 10B, and FIG. 10C.

Furthermore, adult hydra were exposed to a common toxin mixture of 1 ppm AfB1 and 6 ppm ZEN based on the average AfB1 and ZEN concentrations in animal feedstuffs. The inclusion of APCM-12N and APCM-18N at 0.1% inclusion level clearly prevented the mortality of hydra, whereas parent clays at similar level protected hydra slightly. This slight protection is in alignment with the in vitro isotherm results that parent clays can bind AfB1 but not ZEN. The significant protection of APM indicated that they were able to adsorb naturally occurring toxin mixtures of aflatoxin and ZEN at the same time with limited interference. We postulate that the protective activity against toxin mixtures is possibly due to the differences in binding sites and mechanisms of aflatoxin and ZEN.

This is the first discovery of a broad-acting enterosorbent for both aflatoxin and ZEN. The finding in vivo is also consistent with the in vitro isothermal results.

Figure 10C:
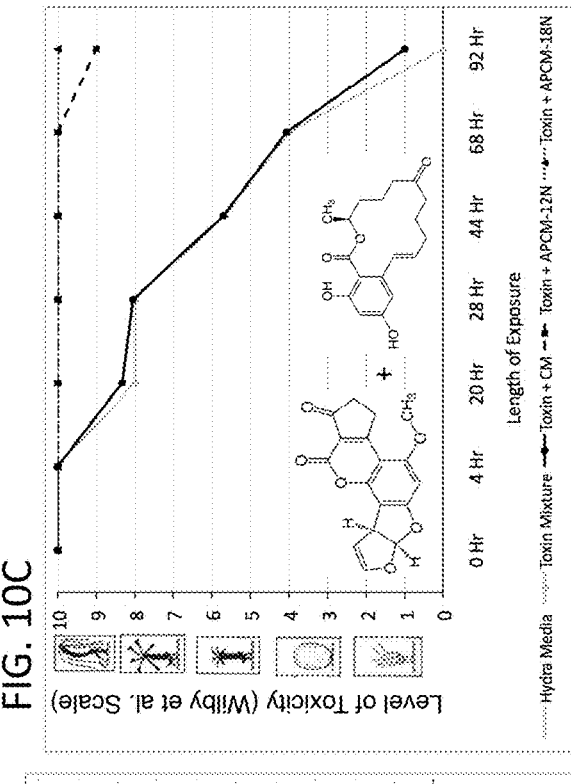
FIG. 10A, FIG. 10B, and FIG. 10C show hydra toxicity and protection by parent CM and APM at 0.005% inclusion level against 20 ppm AfB1 (FIG. 10A), parent CM and APM at 0.01% level against 4 ppm ZEN (FIG. 10B) and parent CM and APM at 0.1% level against toxin mixtures of 1 ppm AfB1 and 6 ppm ZEN (FIG. 10C); hydra media and toxin controls are included in each figure for comparison.
Figure 10A:
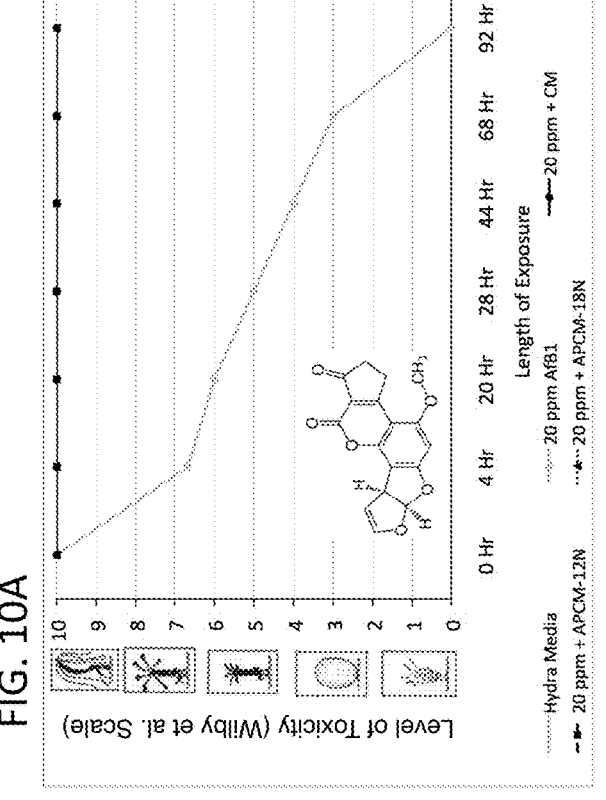
Figure 10B:
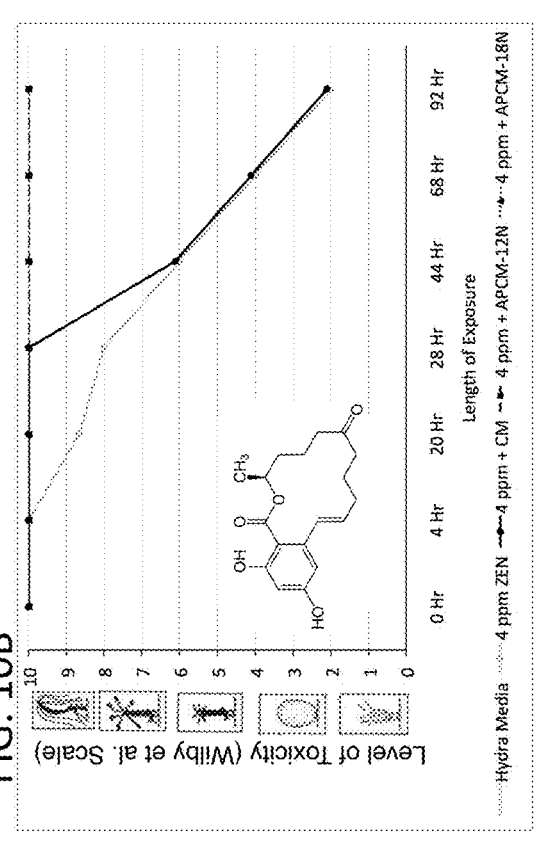

FIG. 10A, FIG. 10B, and FIG. 10C show hydra toxicity and protection by parent CM and APM against 20 ppm AfB1 at 0.005% inclusion level (FIG. 10A), 4 ppm ZEN at 0.01% level (FIG. 10B) and toxin mixtures of 1 ppm AfB1 and 6 ppm ZEN at 0.1% inclusion level (FIG. 10C). Hydra media and toxin controls are included in each figure for comparison.

Isothermal Adsorption and Hydra Assay with Environmental Chemicals.

Figure 12E:
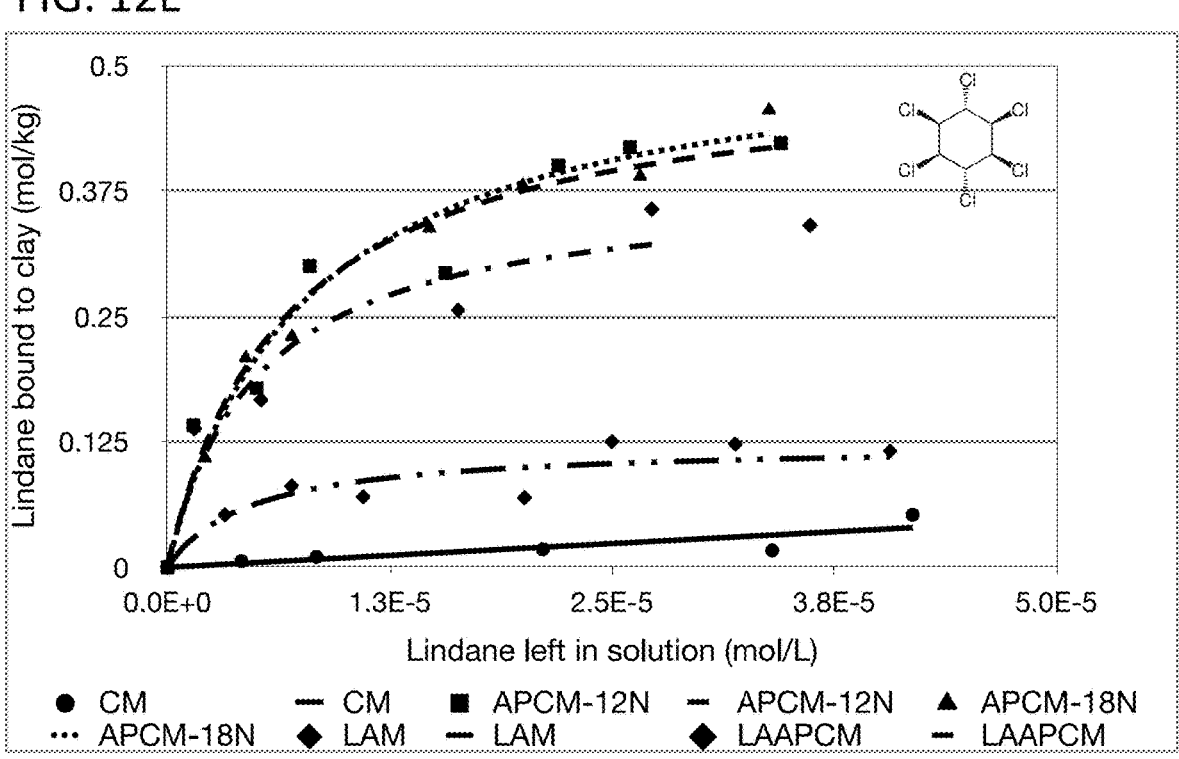

To mitigate hazardous environmental chemicals and protect humans and communities working and living near contaminated sites, we investigated the binding efficacy of APM and lecithin amended montmorillonite (LAM) with representative environmental chemicals. FIG. 12A and FIG. 12B show Langmuir plots of PCP on APCM, APSM and LAM with comparison of parent calcium (FIG. 12A) and sodium (FIG. 12B) montmorillonites. (FIG. 12A) APCM-12N: Qmax=0.23; Kd=2E6; APCM-18N: Qmax=0.21; Kd=1E7; LAM: Qmax=0.11; Kd=2E6. (FIG. 12B) APCM-12N: Qmax=0.1; Kd=3E6; APCM-18N: Qmax=0.14; Kd=5E7. FIGS. 12C and 12D show Langmuir plots of 2,4,6-TCP on APCM (FIG. 12C) and APSM (FIG. 12D) versus parent montmorillonites at 24° C., wherein APCM-12N: Qmax=0.23; Kd=2E5; APCM-18N: Qmax=0.25; Kd=8E5; APSM-12N: Qmax=0.17; Kd=7E5; APSM-18N: Qmax=0.22; Kd=1E6. FIG. 12E shows Langmuir plots of lindane on APCM and LAM versus parent CM, wherein APCM-12N: Qmax=0.5; Kd=2E5; APCM-18N: Qmax=0.53; Kd=1E5; LAM: Qmax=0.12; Kd=2E5.

FIG. 12A and FIG. 12B show that the isothermal plot of PCP on parent montmorillonites had a Freundlich trend, indicating a partitioning activity of PCP toxin onto clay surfaces. The $r^2$ values (>0.8) for LAM, APCM and APSM fit the Langmuir model and the curved shapes indicate that PCP binding was tight onto these clay surfaces and not easily dissociated. APCM resulted in the highest Qmax, and the Qmax values of APSM were similar to that of LAM.

Figure 11:
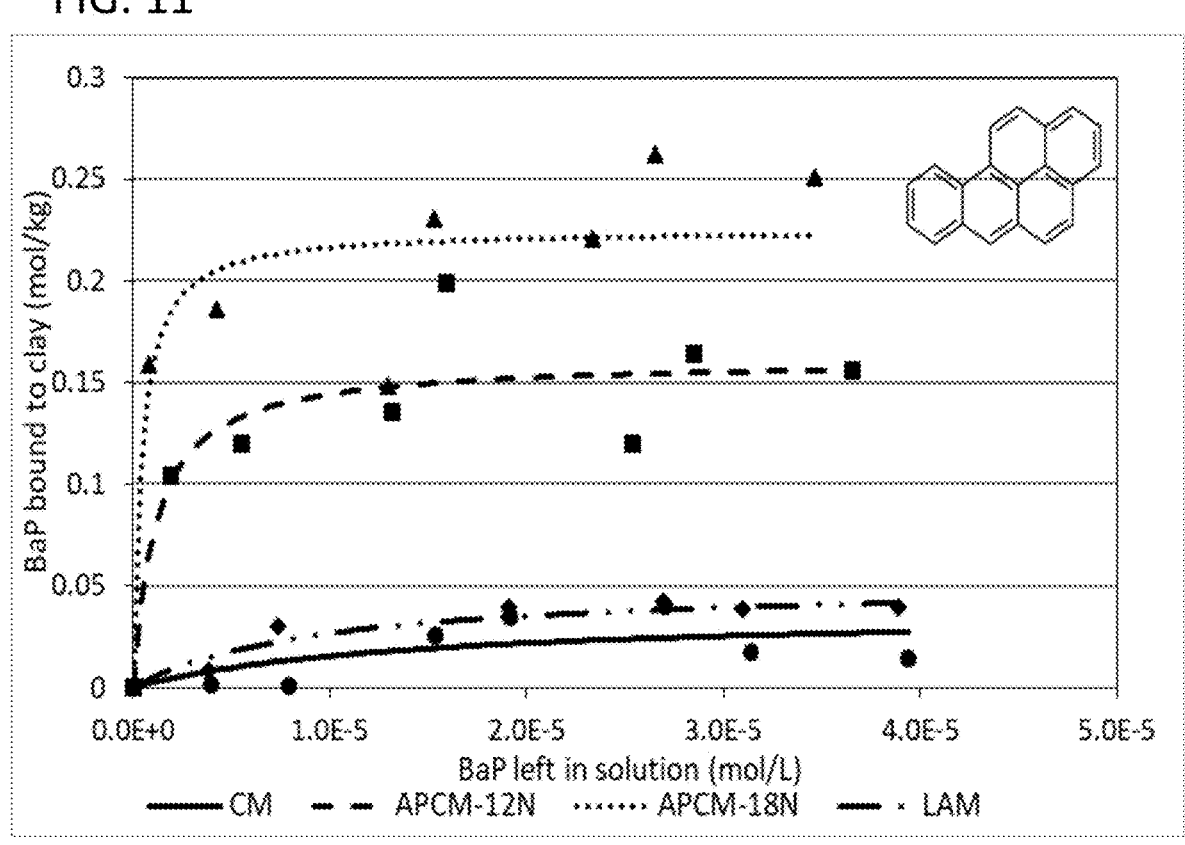
FIG. 11 shows Langmuir plots of BaP on APCM and LAM versus parent CM; CM: Qmax=0.04; Kd=7E4; APCM-12N: Qmax=0.16; Kd=9E5; APCM-18N: Qmax=0.22; Kd=2E6; LAM: Qmax=0.05; Kd=1E5.

Similarly, BaP isothermal adsorption in FIG. 11 shows that all developed enterosorbents including acid treatment and lecithin amendment were able to increase the binding capacity of BaP. Especially APM showed a significant higher Qmax and Kd than parent CM, showing that APM can serve as an efficient sorbent for BaP adsorption. FIG. 11 shows Langmuir plots of diazinon on APM and LAM versus parent CM. CM: Qmax=0.04; Kd=7E4; APCM-12N: Qmax=0.16; Kd=9E5; APCM-18N: Qmax=0.22; Kd=2E6; LAM: Qmax=0.05; Kd=1E5.

Lindane, diazinon, aldicarb and linuron are representative chemicals from major pesticide classes, such as organochlorine, organophosphate, carbamate and phenylurea pesticides. FIG. 13A, FIG. 13B, FIG. 13C, and FIG. 13D show Langmuir plots of lindane (FIG. 13A), diazinon (FIG. 13B) aldicarb (FIG. 13C) and linuron (FIG. 13D) on APM and LAM versus parent CM. (FIG. 13A) APCM-12N: Qmax=0.5; Kd=2E5; APCM-18N: Qmax=0.53; Kd=1E5; LAM: Qmax=0.12; Kd=2E5. (FIG. 13B) CM: Qmax=0.19; Kd=4E6; APCM-12N: Qmax=0.47; Kd=2E6; APCM-18N: Qmax=0.5; Kd=4E5; LAM: Qmax=0.22; Kd=1E6. (FIG. 13C) APCM-12N: Qmax=0.4; Kd=4E6; APCM-18N: Qmax=0.48; Kd=3E6; LAM: Qmax=0.47; Kd=2E7. (FIG. 13D) CM: Qmax=0.09; Kd=5E4; APCM-12N: Qmax=0.15; Kd=5E4; APCM-18N: Qmax=0.22; Kd=4E4. Isothermal results in FIG. 13A, FIG. 13B, FIG. 13C, and FIG. 13D suggest significantly increased binding (Qmax and Kd) for AMP. Lecithin amended montmorillonite was shown to bind lindane and aldicarb tightly with increased Qmax and Kd versus parent montmorillonite.

Figures 13A, 13B, 13C, 13D:
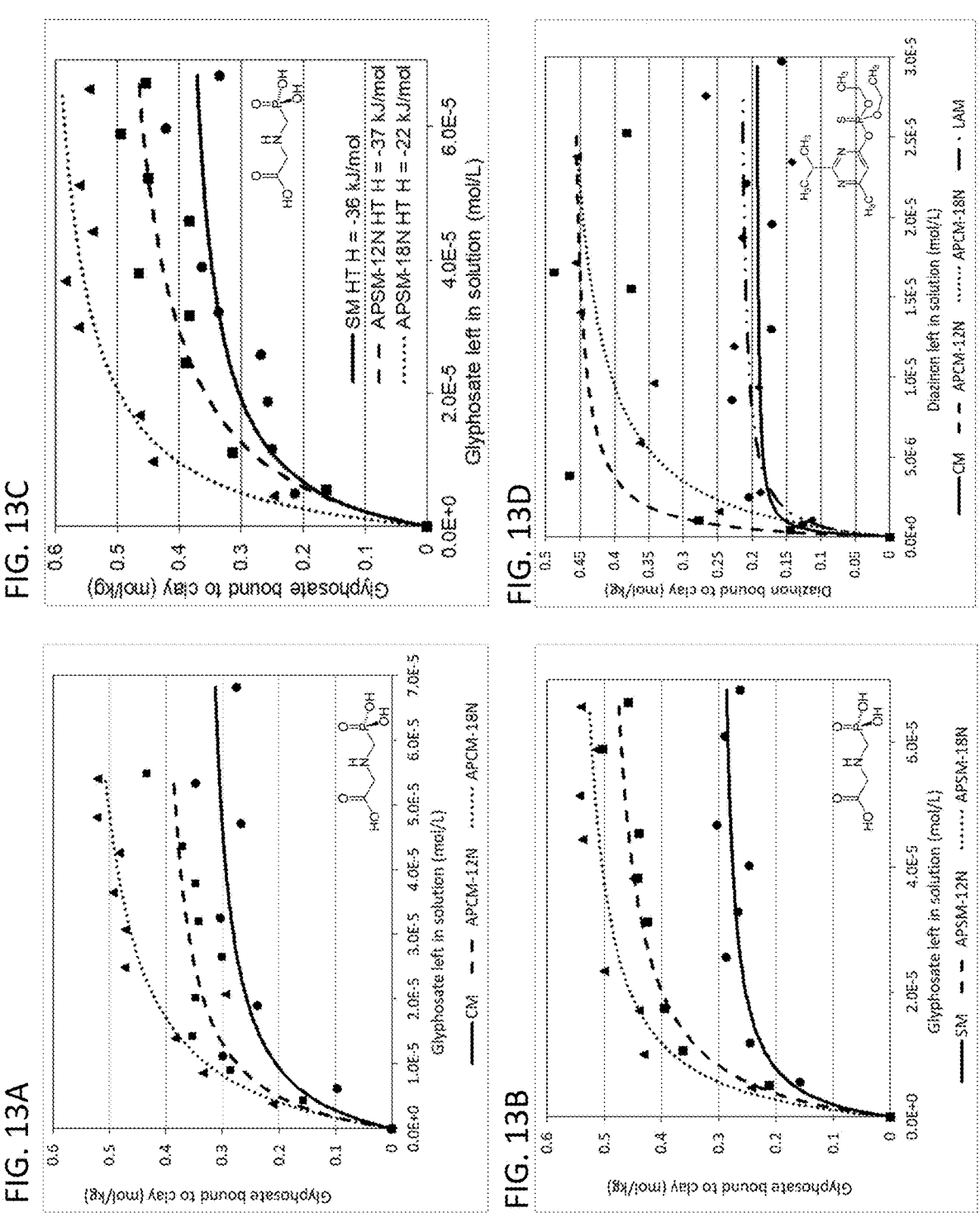
FIG. 13A, FIG. 13B, FIG. 13C, and FIG. 13D show Langmuir plots of lindane (FIG. 13A), diazinon (FIG. 13B) aldicarb (FIG. 13C) and linuron (FIG. 13D) on APCM and LAM versus parent CM.
Figure 13G:
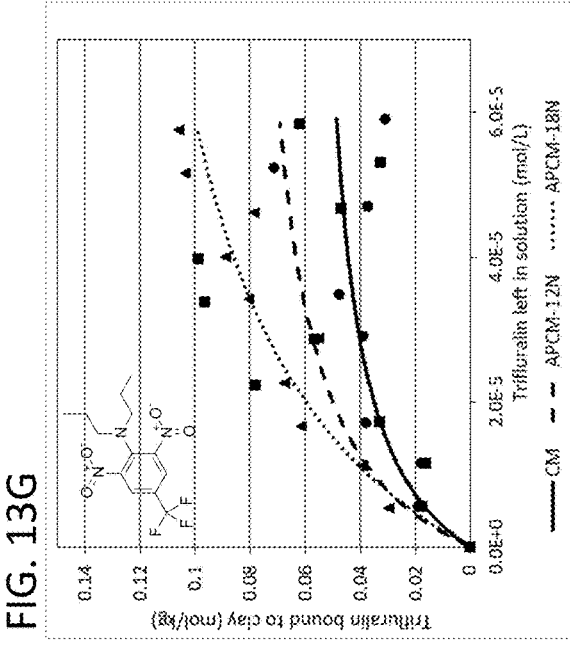
FIG. 13G shows Langmuir plots of glyphosate on APSM versus parent SM at 37° C. (HT) and pH 6.5. SM HT: Qmax=0.41; Kd=1E5; APSM-12N HT: Qmax=0.53; Kd=1E5; APSM-18N HT: Qmax=0.6; Kd=2E5.
Figure 13:
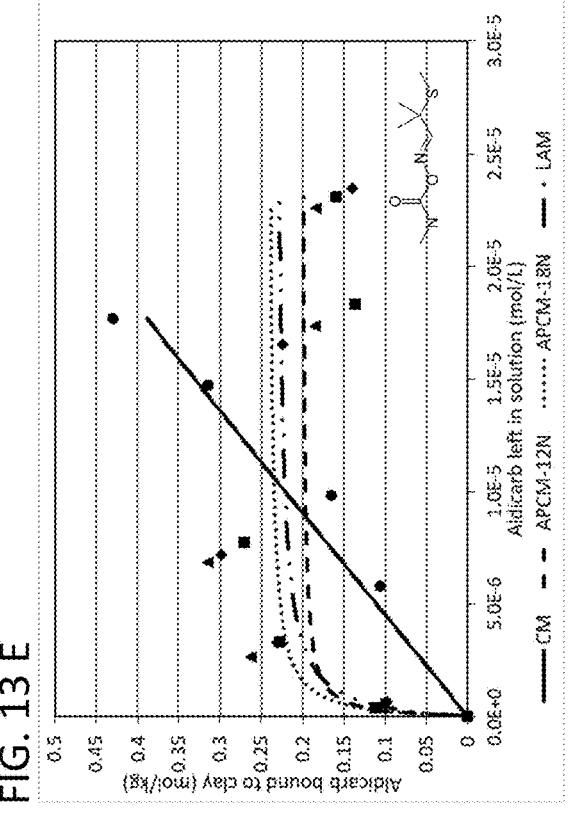
FIG. 13E-F show Langmuir plots of glyphosate on APCM (FIG. 13E) and APSM (FIG. 13F) versus parent montmorillonites at 24° C. and pH 6.5. CM: Qmax=0.32; Kd=2E5; APCM-12N: Qmax=0.42; Kd=2E5; APCM-18N: Qmax=0.58; Kd=1E5; SM: Qmax=0.3; Kd=3E5; APSM-12N: Qmax=0.52; Kd=2E5; APSM-18N: Qmax=0.57; Kd=2E5.
FIG. 13H shows Langmuir plots of trifluralin on APCM versus parent CM at 24° C. CM: Qmax=0.06; Kd=7E4; APCM-12N: Qmax=0.09; Kd=7E4; APCM-18N: Qmax=0.15; Kd=3E4.
Figure 13F:
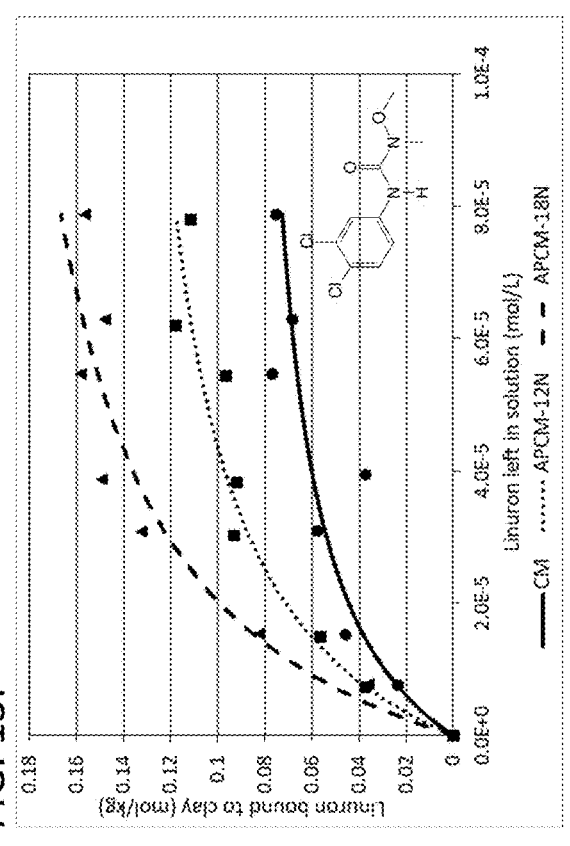

FIG. 13E-F show Langmuir plots of glyphosate on APCM (FIG. 13E) and APSM (FIG. 13F) versus parent montmorillonites at 24° C. and pH 6.5. CM: Qmax=0.32; Kd=2E5; APCM-12N: Qmax=0.42; Kd=2E5; APCM-18N: Qmax=0.58; Kd=1E5; SM: Qmax=0.3; Kd=3E5; APSM-12N: Qmax=0.52; Kd=2E5; APSM-18N: Qmax=0.57; Kd=2E5.

FIG. 13G shows Langmuir plots of glyphosate on APSM versus parent SM at 37° C. (HT) and pH 6.5. SM HT: Qmax=0.41; Kd=1E5; APSM-12N HT: Qmax=0.53; Kd=1E5; APSM-18N HT: Qmax=0.6; Kd=2E5.

FIG. 13H shows Langmuir plots of Trifluralin on APCM versus parent CM at 24° C. CM: Qmax=0.06; Kd=7E4; APCM-12N: Qmax=0.09; Kd=7E4; APCM-18N: Qmax=0.15; Kd=3E4.

Figures 14A, 14B, 14C, 14D:
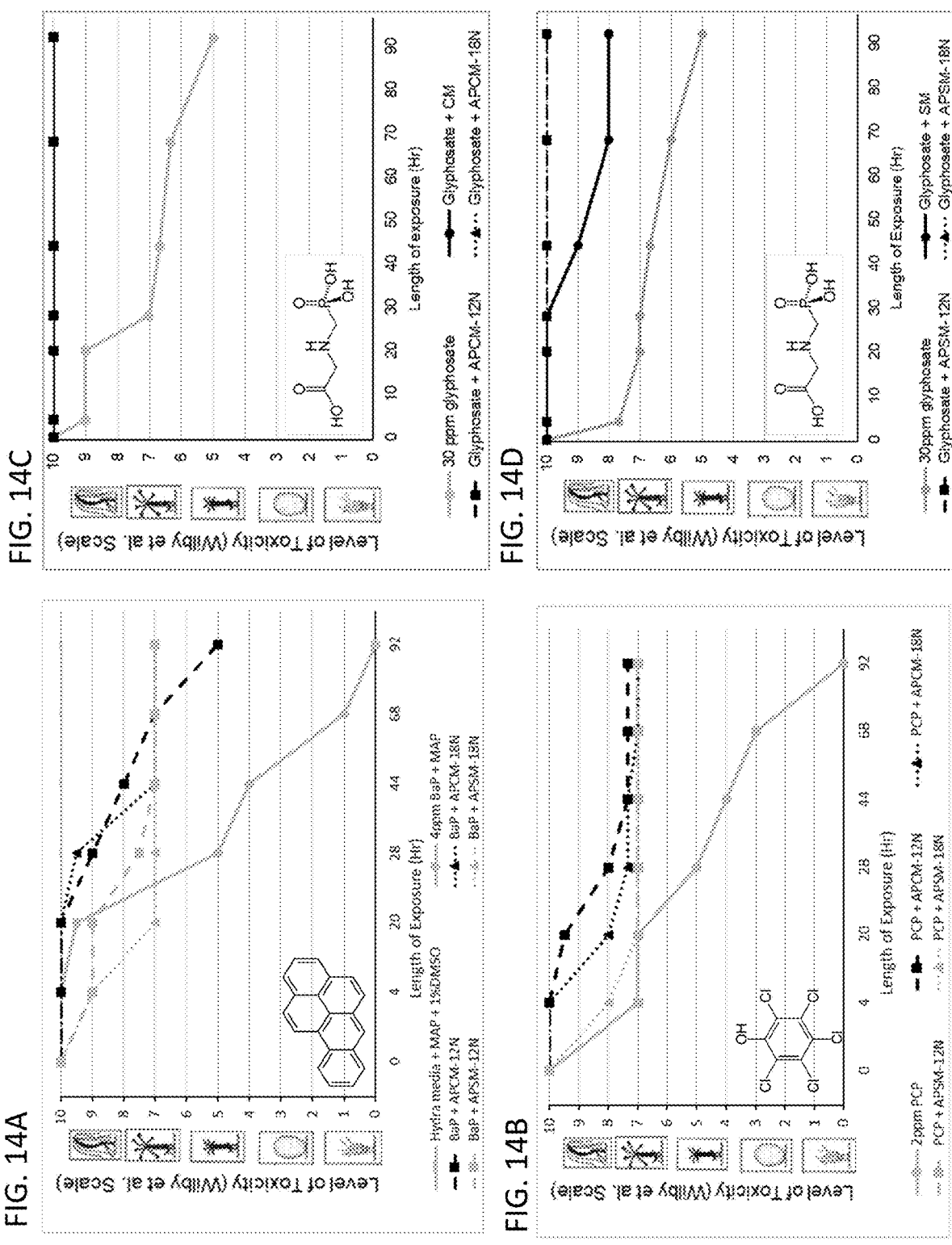

FIG. 14A, FIG. 14B, and FIG. 14C show hydra toxicity and protection by parent montmorillonites and APM against PCP (FIG. 14A), BaP with MAP (FIG. 14B) and aldicarb (FIG. 14C) at the 0.1% inclusion level. Hydra media and toxin controls are included in each figure for comparison. The in vivo hydra assay, in FIG. 14A, FIG. 14B (with MAP for BaP), and FIG. 14C confirmed the protection of APM at a low inclusion level of 0.1%, and inclusion was safe with no adverse effects shown in hydra. Hydra toxicity and protection by parent montmorillonites and APCM (FIG. 14D) and APSM (FIG. 14E) at the 0.1% inclusion level against glyphosate. FIG. 14F shows hydra toxicity and protection by parent montmorillonites and APM at the 0.2% inclusion level against trifluralin. Hydra media and toxin controls are included for comparison.

Antibacterial Activity.

Figure 15:
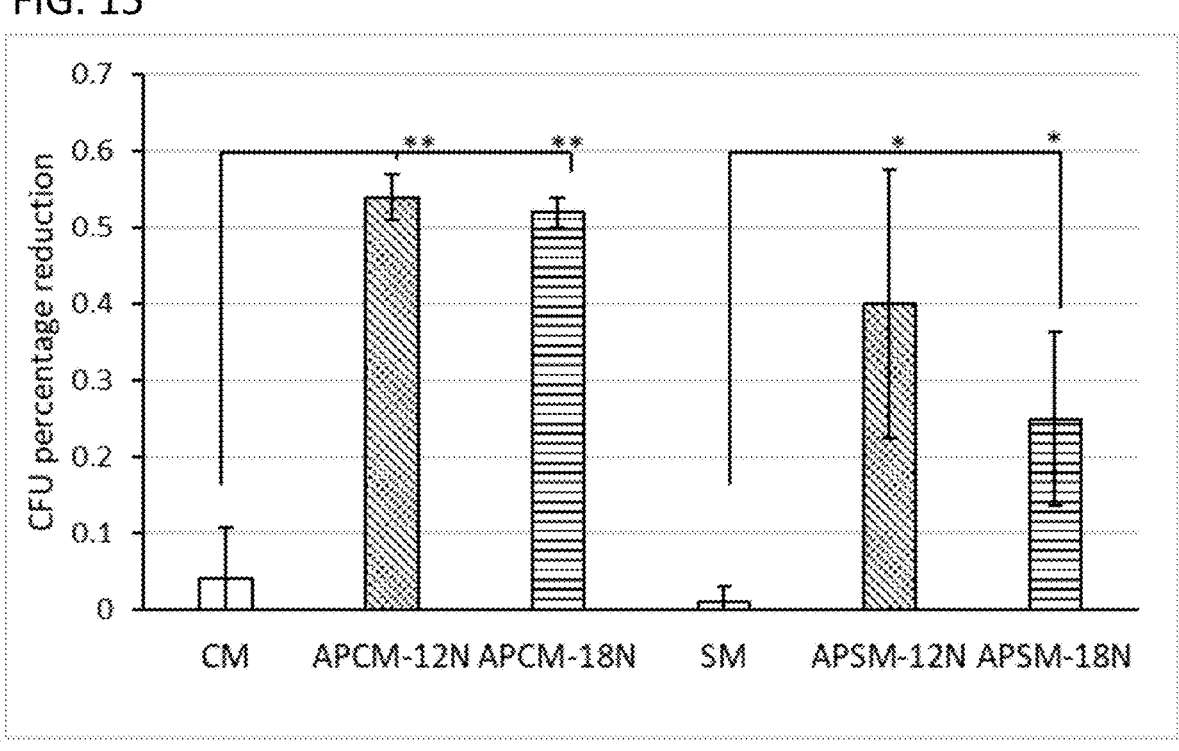
FIG. 15 shows the percentage reduction of *E. coli* bacteria on the surface of sorbents, measured as colony forming units (CFU); the sorbents were included at 0.01% (*p<0.05, **p<0.01); p is a probability value, wherein levels less than *0.05 and *0.01 are considered to be statistically different.
Figure 16C:
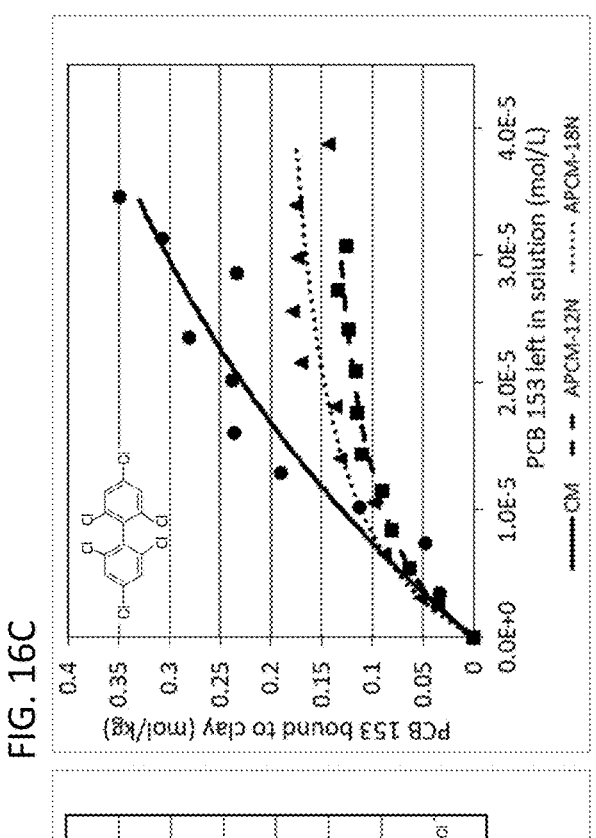
FIG. 16A, FIG. 16B and FIG. 16C show Langmuir plots of PCB 77 (FIG. 16A), 126 (FIG. 16B) and 153 (FIG. 16C) on APCM at 24° C.
Figure 16A:
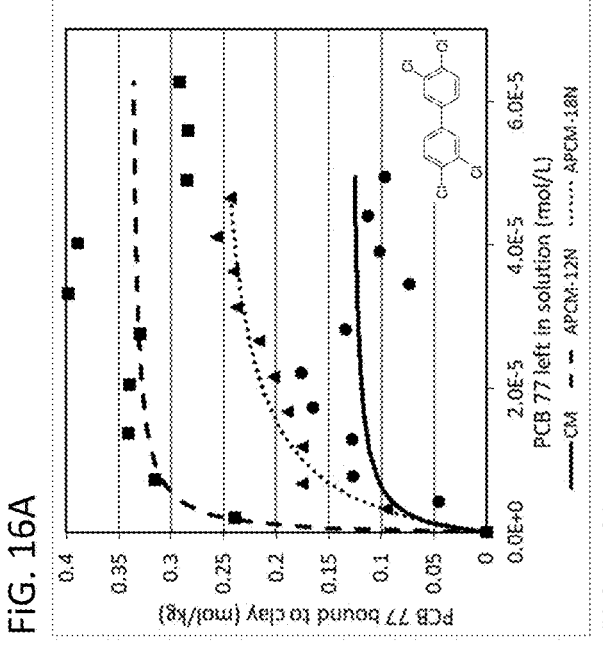
Figure 16B:
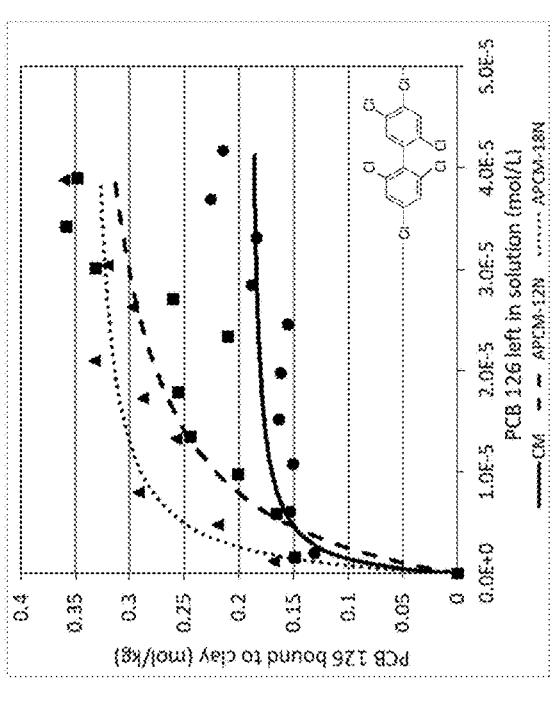
Figures 17A, 17B, 17C:
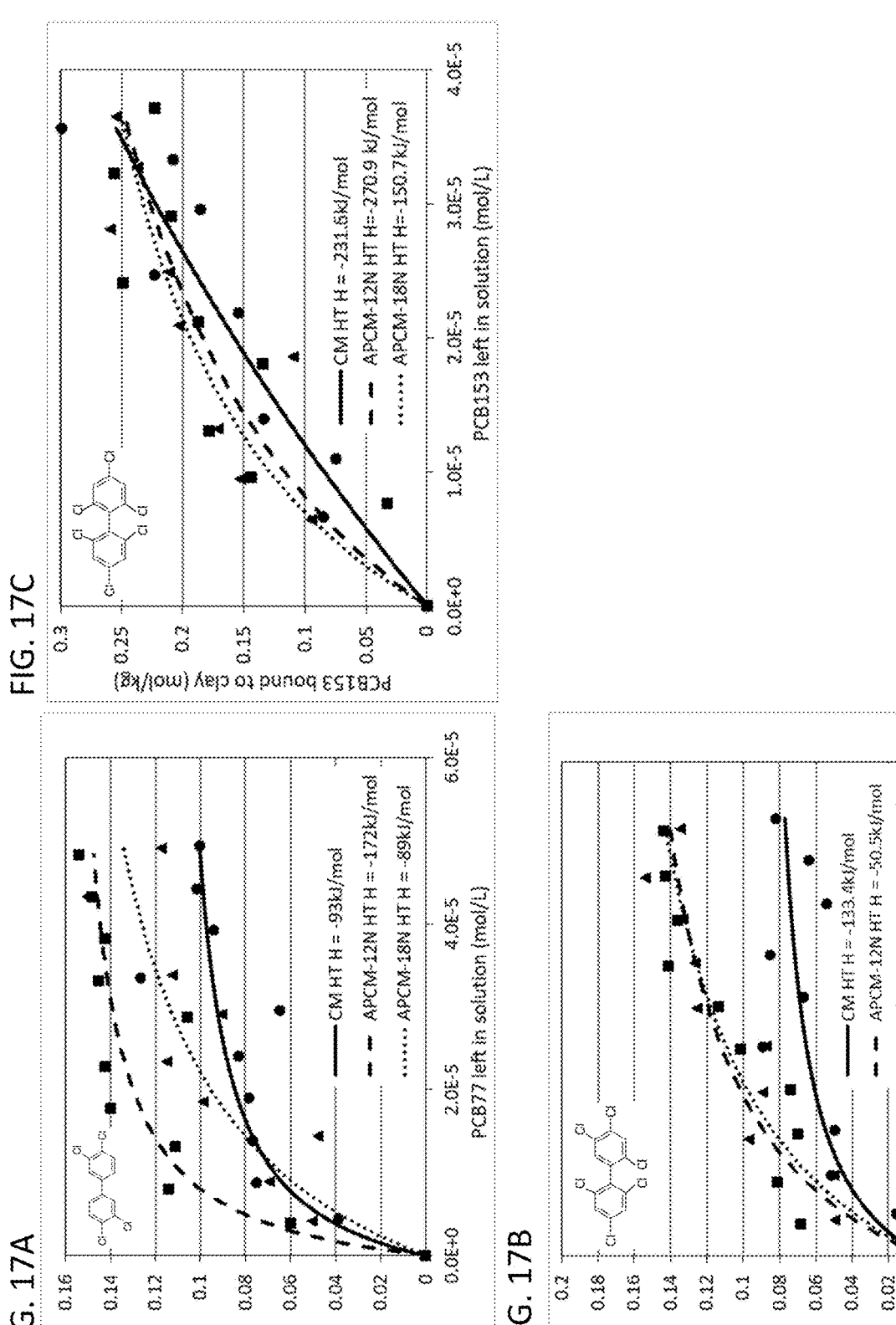
FIG. 17A, FIG. 17B, FIG. 17C show Langmuir plots of PCB 77 (FIG. 17A), 126 (FIG. 17B) and 153 (FIG. 17C) on APCM at 37° C. (HT).
Figure 18A:
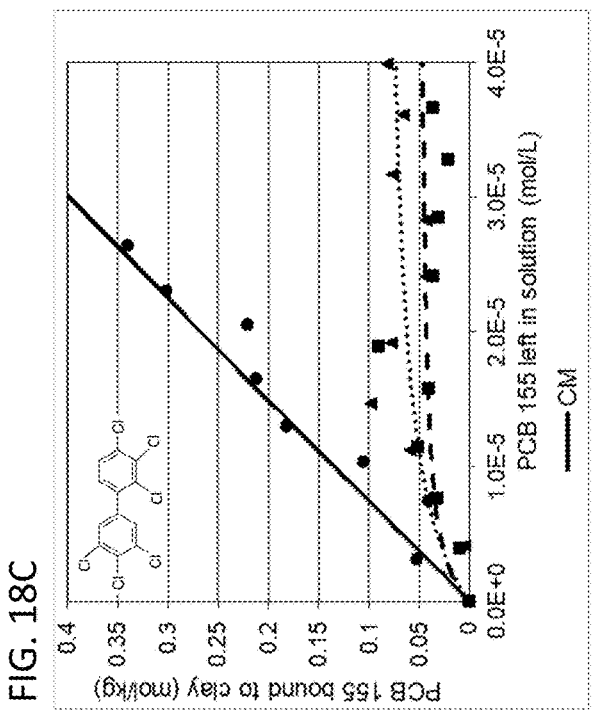
FIG. 18A, FIG. 18B, FIG. 18C show Langmuir plots of PCB 157 (FIG. 18A), 154 (FIG. 18B) and 155 (FIG. 18C) on APCM at 24° C.
Figure 18C:
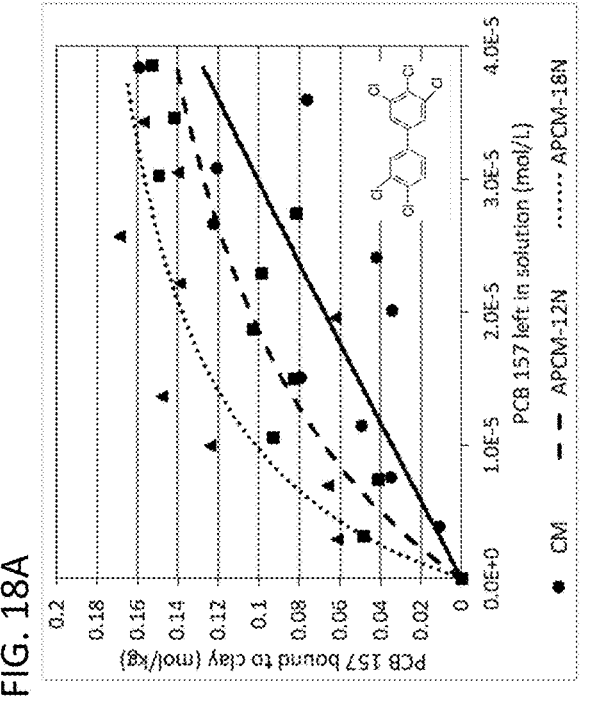
Figure 18B:
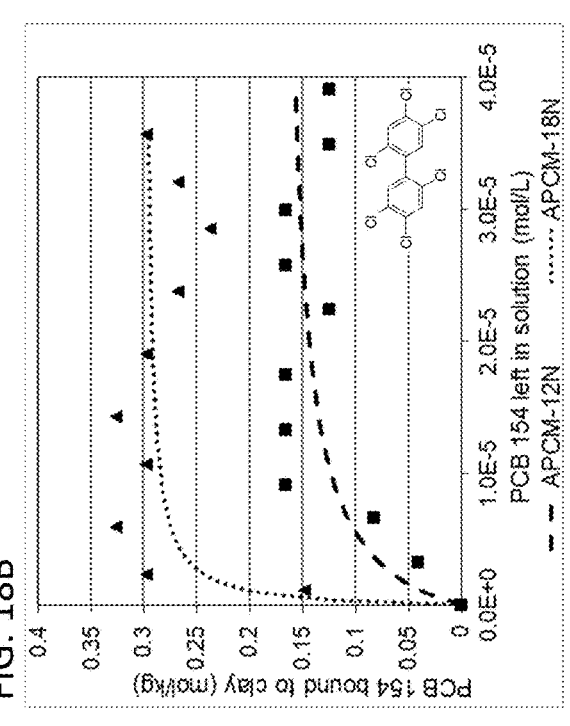
Figure 20A:
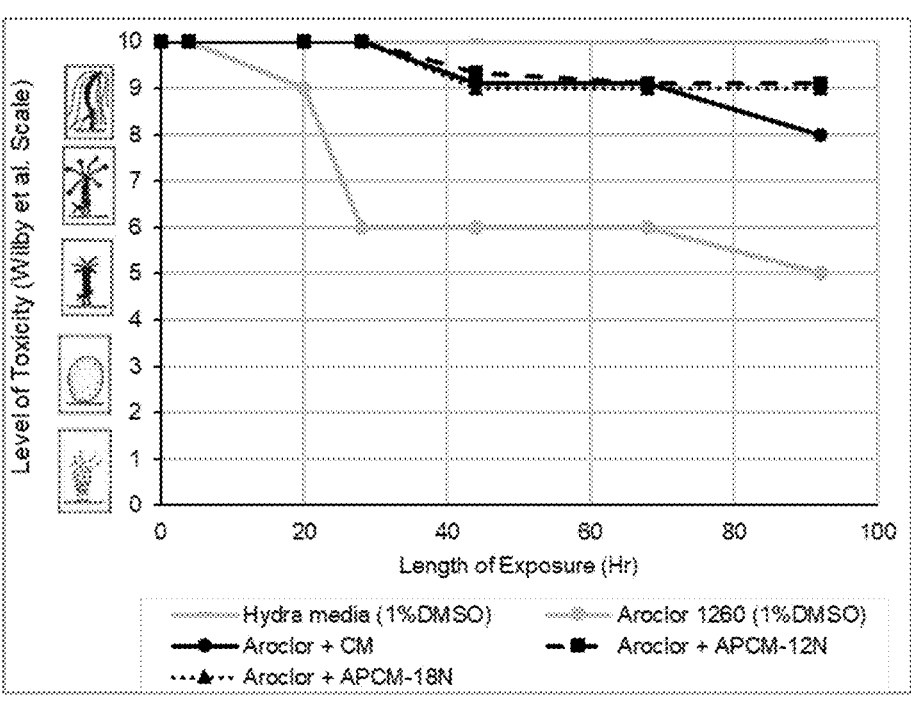
FIG. 20A, FIG. 20B show Hydra toxicity and protection by parent montmorillonites and APM at the 0.2% inclusion level against Aroclor 1254 (FIG. 20A) and 1260 (FIG. 20B). Hydra media and toxin controls are included for comparison.
Figure 20B:
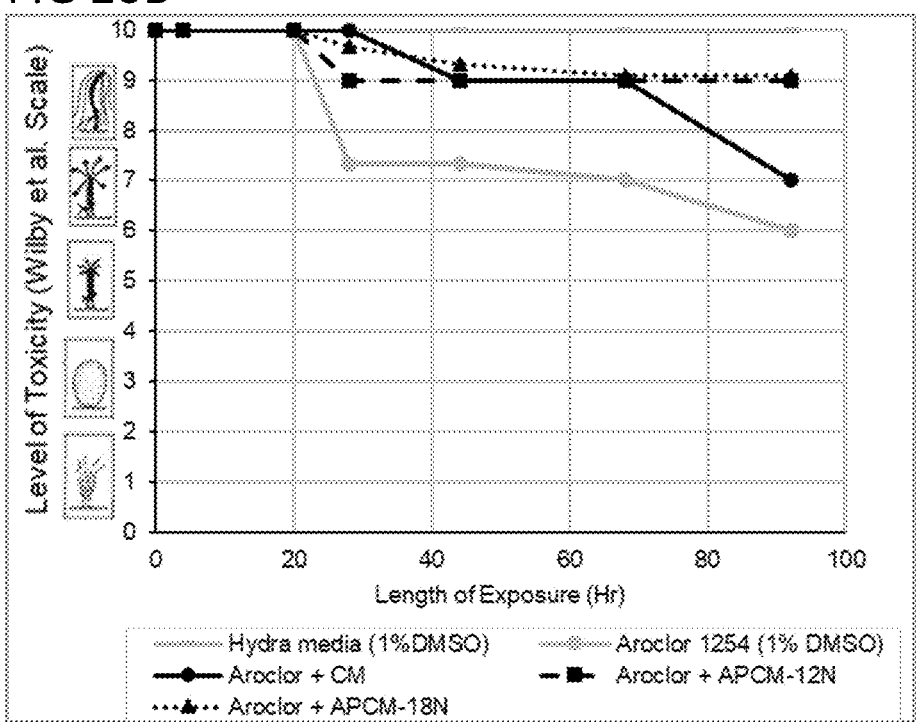
Figure 21A:
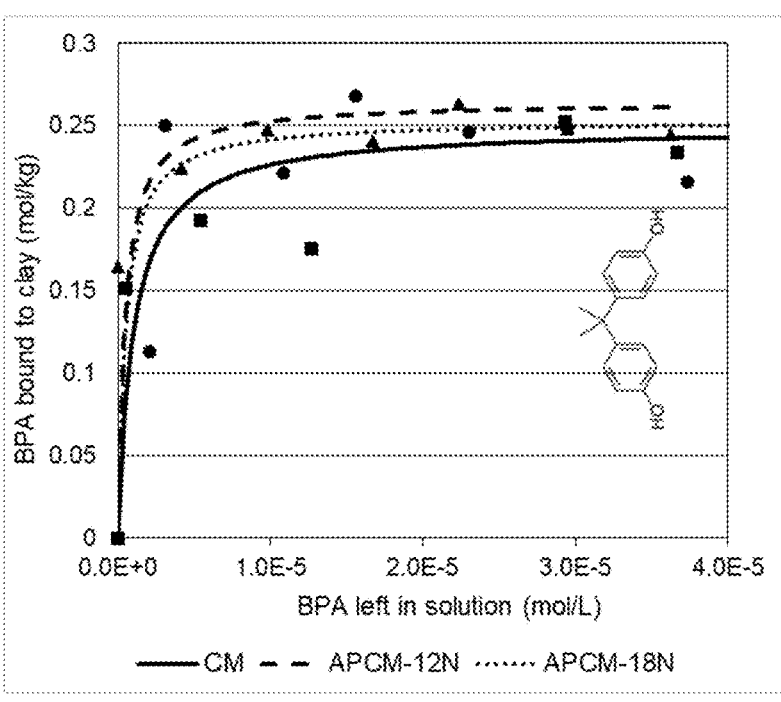
FIG. 21A, FIG. 21B show Langmuir plots of BPA on APCM versus parent CM at 24° C.
Figure 21B:
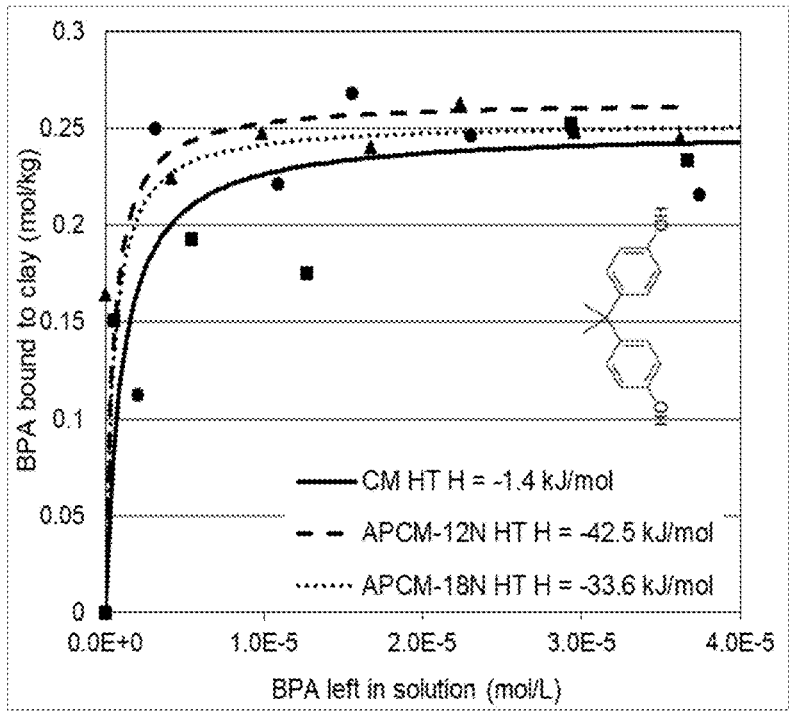

Bacteria are major problems in flooded communities and contaminated sites, leading to gastrointestinal disease. Other than sorbents for superfund chemicals, we are also developing materials that tightly bind and inactivate bacteria, such as E. coli. FIG. 15, which shows the CFU percentage reduction on parent and APM at 0.01% inclusion (*p<0.05, **p<0.01), shows the results of studies comparing the antibacterial activities between the parent calcium and sodium montmorillonite clays (CM and SM) and APM in reducing bacterial plate counts. Results show that parent montmorillonite clays failed to produce obvious reduction in bacterial colony forming units from solution (CFU/mL), whereas APM significantly increased antibacterial activities that reduced CFU by 55% (APCM), 40% and 27% (APSM).

There are no reports (other than activated carbon) of effective sorbents for ZEN and hazardous environmental chemicals. With APM we have simulated the structure of activated carbon with high surface area and porosity. Importantly, parent montmorillonite clays represented in this study are the only ones that have been shown to be safe for human and animal consumption. This clinical translation of enterosorbent therapy will be field-practical and cost-effective sorbents for environmental chemicals.

Based on the results, acid treatment was shown to refine the enterosorbent, decrease its expansibility in water and increase its surface area and decrease trace metal content due to the leaching out of cations. The differences of trace metals in 12N and 18N indicate that lower acid concentrations (12N) leach out cations in the interlayer and octahedral sheets, whereas higher acid concentrations (18N) start to replace cations in the tetrahedral sheets, which are less reactive. The results are in alignment with an FTIR report on acid clays (Tyagi, B. et al., 2006). The regulation level for lead as a heavy metal set by the Food and Drug Administration (FDA) is 10 ppm. The lead level in parent clay was detected as 11.7 ppm (the relative value was adjusted to 1).

The results showed that lead concentration was not changed by sulfuric acid treatment for 24 h at high temperature nor any other treatments including sonication and washing with citric acid that chelates metals (data not shown). The results indicate that lead is very tightly bound within the clay structure, and is not dissociated, even in extreme conditions such as heat, strong acid and sonication for long duration. Based on these findings, lead should not be bioavailable when the clay is included in the diet, since stomach acid is approximately 2, which is mild compared to the herein described treatment.

As indicated in the results, acid treated CM (calcium-rich montmorillonite) and SM (sodium-rich montmorillonite) clays were able to maintain the adsorption of aflatoxin with similar binding curves and capacities and more importantly, improve ZEN binding (from a Freundlich trend to a Langmuir model) indicating saturable binding sites and tight binding of ZEN. The high binding capacity (Qmax>0.2) suggests the ability of APM to serve as effective ZEN enterosorbents, which is probably due to higher surface areas than the parent clays. The tight binding also was reflected by the high enthalpies ($\Delta H < -70$ kJ/mol), which indicate that the interaction energy was almost 4 times more than a weak attraction. This is the first discovery of a sorbent that serves as a very effective binder of ZEN with high binding capacity and enthalpy. It also should be clean and safe for human and animal consumption. Aflatoxin binds mainly in the clay interlayers, which supports previous studies by the inventors. Whereas, the major binding sites for the more hydrophobic ZEN were shown to be the more organophilic basal surfaces and edge sites. This difference in binding sites and mechanisms contributes to the ability of these clays to adsorb the toxin mixture of aflatoxin and ZEN at the same time with limited interference. The in vivo hydra assay further confirmed the safety and efficiency of these APM clays against individual mycotoxins, and toxin mixtures of aflatoxin and ZEN as well.

To mitigate hazardous environmental chemicals and protect humans and communities working and living near contaminated sites, we investigated the binding efficacy of these APM using representative environmental chemicals. Isothermal analyses, along with the in vivo hydra assay, showed that APM was able to serve as a safe and very effective enterosorbent for prioritized chemicals from various solvents, PAHs, and pesticides. The representative chemicals in each class include PCP, BaP, lindane, diazinon, aldicarb and linuron. This is the first report of a sorbent material (other than activated carbon) with high binding efficacy for these environmental chemicals. Since microbes often cause gastrointestinal disease at contaminated sites and are of great public health concern, we investigated the adsorption ability of APM for microbes, such as *E. coli*. At a very low sorbent inclusion level of 0.01%, parent CM and SM did not show obvious effects on bacterial colony forming units in the solution. Whereas, all of the APM decreased bacterial counts significantly at the same inclusion level, indicating the anti-bacterial activity is remarkably increased by acid treatment. Thus, these clays can be delivered and included in water and the diet to reduce animal and human exposures to mycotoxins, environmental chemicals and microbes as well.

Lecithin is a natural fatty substance occurring in animal and plant tissues and is commonly found in soybeans, eggs, marine sources, etc. Isotherm results indicated that lecithin amended montmorillonites (LAM) were able to significantly increase binding of PCP, BaP, lindane and aldicarb. This result indicated that LAM is novel, broad-acting and potentially tunable within chemical classes based on different chemical properties. The mechanism of binding is possibly because lecithin is amphiphilic, and the permanent positive charge from the ammonium group allows lecithin to insert onto the negative charged clay surfaces, and the hydrophobic fatty acid tails facilitate attraction of organophilic compounds. Lecithin was reported to increase chemical sensitization on discharge of cnidocyte and delivery of synaptic signals in hydra, and thus can induce exocytosis (Thurm U., et al., 2004), therefore lecithin amended clay was not included in hydra assay.

Based on these studies, APMs can serve as broad-acting enterosorbents for the mitigation of exposures to mycotoxins, environmental chemicals and microbes. LAM is broad-acting and tunable for environmental chemicals based on diverse chemical properties. These developed sorbents can be delivered to animals and humans as capsules, snacks, vitamins, food, condiments and stirred in flavored-drinking water during disasters to decrease exposures. This is the first report of the development of novel sorbent therapy that is safe for human and animal consumption and will effectively decrease exposures to broad-spectrum chemicals.

While various exemplary embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, RL and an upper limit, RU is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Use of the term "optionally" with respect to any element of a claim is intended to mean that the subject element is required, or alternatively, is not required. Both alternatives are intended to be within the scope of the claim Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

Additional Description.

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately α-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments Disclosed Herein Include:

An enterosorbent comprising: a treated sorbent, wherein the treated sorbent comprises a parent sorbent that has been acid and/or lecithin treated, and wherein the treated sorbent is operable for adsorption of one or more toxins from a gastrointestinal tract of a living being when introduced thereto, such that a bioavailability of and exposure of the living being to the one or more toxins is decreased.

A method of producing an enterosorbent, the method comprising: processing a parent clay to produce a processed clay, wherein the processing comprises: acid treating to produce an acid treated clay via exposure to reagent grade sulfuric acid solution having a concentration (e.g., an equivalent concentration or normality (N)) of greater than or equal to about 6N, 12N, or 18N, or in a range of from about 6N to about 18N or from about 6N to about 12N; and/or lecithin treating to produce a lecithin treated clay via modification with lecithin at 100% cation exchange capacity.

A method of reducing exposure of a living being to one or more toxins, the method comprising: introducing into the living being an enterosorbent as disclosed herein.

Each of embodiments listed above may have one or more of the following additional elements: Element 1: wherein the one or more toxins are selected from mycotoxins, environmental chemicals, herbicides, and microbes. Element 2: wherein the one or more toxins are selected from industrial solvents, polycyclic aromatic hydrocarbons (PAHs), pesticides, herbicides or combinations thereof. Element 3: wherein the one or more toxins are selected from pentachlorophenol (PCP), benzo[a]pyrene (BaP), lindane, diazinon, aldicarb, linuron, aflatoxin (AfB1), zearalenone (ZEN), *Escherichia coli* (*E. coli*), or combinations thereof. Element 4: wherein the parent sorbent is a natural or synthetic organophilic sorbent. Element 5: wherein the parent sorbent comprises a montmorillonite clay and wherein the treated sorbent comprises a treated montmorillonite clay. Element 6: wherein the parent clay comprises a sodium or calcium montmorillonite clay. Element 7: wherein the parent clay has been acid treated via exposure to reagent grade sulfuric acid. Element 8: wherein the parent clay has been acid treated via exposure to reagent grade sulfuric acid having a concentration (e.g., an equivalent concentration or normality) of greater than or equal to about 6N, 12N, or 18N, or in a range of from about 6N to about 18N or from about 6N to about 12N. Element 9: wherein the parent clay has been further treated via modification of the parent clay with lecithin at 100% cation exchange capacity. Element 10: wherein the treated clay tightly binds the one or more toxins, as evidenced by a maximum binding capacity (Qmax) and/or distribution coefficient (Kd) that is greater than or equal to that of carbon material. Element 11: wherein the adsorption comprises chemical adsorption of the one or more toxins. Element 12: wherein the one or more toxins comprise aflatoxin (AfB1) and zearalenone (ZEN), and wherein the treated sorbent comprises multiple types of binding sites and/or mechanisms of binding such that the treated sorbent is operable to non-competitively adsorb AfB1 and ZEN. Element 13: wherein the multiple types of binding sites include binding sites in a clay interlayer, which primarily adsorb AfB1, and binding sites of organophilic basal surfaces and edges sites of the treated sorbent, which primarily adsorb ZEN. Element 14: wherein the enterosorbent is further operable for the adsorption of *Escherichia coli* (*E. coli*), as evidenced by a decreased number of microbe colony forming units (CFUs). Element 15: wherein the enterosorbent is operable to provide a decreased number of microbe colony forming units (CFUs) relative to the parent montmorillonite clay. Element 16: wherein the treated montmorillonite clay exhibits a maximum binding capacity (Qmax) for ZEN that is greater than the Qmax for ZEN of the parent montmorillonite clay. Element 17: wherein the Qmax of the treated montmorillonite clay is at least about 0.2 moles per kilogram (mol/kg). Element 18: wherein the treated montmorillonite clay exhibits an absolute adsorption enthalpy (|ΔHads|) for ZEN (as determined by the Van't Hoff Equation) that is greater than the |ΔHads| for ZEN of the parent montmorillonite clay. Element 19: wherein the |ΔHads| for ZEN of the treated montmorillonite clay is greater than or equal to about 20, 30, 40, 50, 60, or 70 kiloJoules per mole (kJ/mol). Element 20: wherein the treated sorbent is a lecithin treated montmorillonite clay, and wherein the one or more toxins comprise pentachlorophenol (PCP), benzo[a]pyrene (BaP), lindane, aldicarb, or combinations thereof. Element 21: wherein the lecithin treated montmorillonite clay exhibits increased binding (e.g., as evidenced by an increased maximum binding capacity (Qmax)) relative to the parent montmorillonite clay. Element 22: wherein the treated montmorillonite clay has a decreased coefficient of linear expansibility (COLE) in water relative to the parent montmorillonite clay. Element 23: wherein the treated montmorillonite clay has an increased total surface area and/or porosity relative to the parent montmorillonite clay. Element 24: wherein the treated montmorillonite clay has a total surface area that is increased by at least 40% relative to the parent montmorillonite clay. Element 25: wherein the treated montmorillonite clay comprises a reduced amount of trace metals relative to the parent montmorillonite clay. Element 26: wherein the trace metals include aluminum, calcium, sodium. Element 27: wherein the treated montmorillonite clay exhibits tight binding of lead, such that lead is not dissociated upon introduction of the enterosorbent into the gastrointestinal tract of the living being. Element 28: wherein the treated montmorillonite clay has a structure that simulates that of activated carbon. Element 29: wherein acid treating comprises stirring in the sulfuric acidic solution and lecithin treating comprises stirring in a lecithin solution comprising cations and acid. Element 30: wherein stirring comprises stirring for at least 8 h at a stirring temperature. Element 31: wherein acid treating comprises a stirring temperature that is above room temperature (e.g., about 60° C.), and wherein lecithin treating comprises a stirring temperature about equal to room temperature. Element 32: wherein acid treating further comprises cooling (e.g., to room temperature), removing from the acidic solution (e.g., via centrifuging), and washing with water (e.g., with distilled water); wherein lecithin treating further comprises removing from the lecithin solution (e.g., via centrifuging), and washing with water (e.g., with distilled water); or both. Element 33: further comprising drying and sizing the activated clay. Element 34: wherein sizing comprises grinding and sieving to provide an activated clay having a uniform and/or desired size. Element 35: wherein the desired size is less than or equal to about 125 μm. Element 36: wherein drying comprises drying in an oven at a drying temperature and for a drying time. Element 37: wherein the drying temperature is greater than or equal to about 110° C., wherein the drying time is at least eight h (e.g., overnight), or a combination thereof. Element 38: wherein during acid treating, interlayer cations are exchanged with hydrogen protons from the acid, following dissolution of some of the octahedral and tetrahedral sheets in the clay structure, such that the acid treated activated clay is an amorphous silica structure with high reactivity and catalytic activity. Element 39: wherein lecithin treating is performed subsequent or simultaneously with acid treating. Element 40: wherein lecithin treating is performed at low pH (e.g., a pH of less than or equal to about 1, 2 or 3). Element 41: wherein lecithin treating produces amphiphilic surfaces on the lecithin treated clay. Element 42: wherein the method is tunable to provide a broad acting enterosorbent effective for the adsorption of a variety of toxins, based on chemical properties thereof. Element 43: further comprising tuning the treatment of the parent clay, the selection of the parent clay from available parents clays, or a combination thereof based on one or more of the differences in hydrophobicity (logP, which refers to the logarithm of the octanol-water partition coefficient), capacity, affinity, enthalpy of adsorption (ΔHads), charge, size, volume, and surface area of the one or more toxins and/or available parent clays. Element 44: wherein the enterosorbent is an any enterosorbent described herein. Element 45: wherein introducing comprises introducing into a gastrointestinal tract of the living being. Element 46: wherein introducing into the gastrointestinal tract of the living being comprises introducing in water, milling into flour for cooking, adding to feeds, foodstuffs and/or pills, or a combination thereof. Element 47: wherein the introducing comprises introducing at a sorbent inclusion level in a range of from about 0.0005% to about 0.01%, or less than or equal to about 0.0005%, 0.005%, 0.01%, 0.05%, or 0.1%. Element 48: further comprising producing the enterosorbent via the method disclosed herein.

Additional Embodiments:

One embodiment of the current invention details an edible enterosorbent composition for adsorption of one or more toxins from an environment or a gastrointestinal tract of a living organism. The edible enterosorbent composition comprises a phyllosilicate-type mineral having an average particle size less than 150 um and a lecithin composition, forming the edible enterosorbent composition. The edible enterosorbent composition is capable of increasing adsorption of one or more toxins selected from mycotoxins, environmental chemicals, microbes, pesticides; herbicides or combinations thereof (FIGS. 11-13). It is possible to visualize the increased adsorption by determining a maximum binding capacity (Qmax) and/or distribution coefficient (Kd) of the edible enterosorbent composition that is greater than the phyllosilicate-type mineral alone. In the case of visualizing the decreasing toxicity of bacteria, the edible enterosorbent can be used to decreased number of microbe colony forming units (CFUs) relative to the phyllosilicate-type mineral alone.

A second embodiment of the invention's enterosorbent utilizes the phyllosilicate-type mineral selected from a synthetic phyllosilicate type mineral, a natural phyllosilicate-type mineral, a montmorillonite clay, a sodium montmorillonite clay; a calcium montmorillonite clay, or combination thereof.

The enterosorbent properties of the instant invention have been shown to be further enhanced by utilizing a strong acid (FIGS. 4-22). More specifically, the phyllosilicate-type mineral was treated with the strong acid forming a strong-acid-treated phyllosilicate mineral having increased surface area, increased numbers and types of toxin binding sites of the enterosorbent composition (FIG. 4). The increased surface area and increased binding sites are capable of increasing adsorption of one or more toxins. Moreover, the increase is visualized as a maximum binding capacity (Qmax) and/or distribution coefficient (Kd) that is greater than or equal to that of a carbon material and/or a decreased number of microbe colony forming units (CFUs) relative to the phyllosilicate-type mineral alone.

Not wanting to be bound by theory, acids that are capable of increasing the surface area and/or binding sites in the phyllosilicate mineral will also increase the acid treated-enterosorbent's ability to bind toxins (FIG. 4-22). The enterosorbent of the instant invention used the strong-acid-treated phyllosilicate-type mineral that was exposed to the strong-acid selected from a group of strong acids comprising: dilute sulfuric acid; battery acid; chamber acid; tower acid; concentrated sulfuric acid; near-saturated calcium sulfuric acid; saturated calcium sulfuric acid; super-saturated calcium sulfuric acid; sulfate anions; complex ions containing calcium; sulfates; strong acidic solution with sparingly-soluble Group IIA complexes; or combinations thereof.

The enterosorbent composition of the instant invention was capable of binding toxins with a minimum of strong acid treatments. A natural phyllosilicate-type mineral, such as montmorillonite clay was capable of binding more ZEN when compared to the phyllosilicate-type mineral alone. Using a strong acid to increase the affinity of a toxin to a phyllosilicate-type mineral mixed with lecithin is not obvious to one having ordinary skill in the art. A preferred edible enterosorbent comprises a range of 30%-90% by weight montmorillonite; a range of 1%-75% by weight lecithin; and a range of 10%-50% by weight acid and the combinations thereof.

A third embodiment of the edible enterosorbent composition selects one or more toxins that are bound are selected from: organochlorine derivative compounds, benzopyrene derivative compounds, polycyclic aromatic hydrocarbon derivative compounds, organophosphate compounds, dinitroaniline derivative compounds, cholinesterase inhibitor derivative compounds, phenylurea derivative compounds, mycotoxins, bacteria, pentachlorophenol (PCP); benzo[a] pyrene (BaP); lindane, diazinon; aldicarb; linuron; aflatoxin (AfB1); zearalenone (ZEN); *Escherichia coli* (*E. coli*); industrial solvents; polycyclic aromatic hydrocarbons (PAHs); 1,2,3-Trichloropropane (TCP); Phenol; Benzene; Toluene; Pyrene; BFF; Naphthalene; 2,4 D; 2,4-Dinitrophenylhydrazine (2,4-DNP); atrazine; glyphosate; Dichlorodiphenyltrichloroethane (DDT); paraquat; α-amino-3-hydroxy-5-methyl-4-isoxazolepropionic acid (AMPA); Bisphenol A (BPA); Bisphenol S (BPS); Dibutyl phthalate (DBP); di-2-ethylhexyl phthalate (DEHP); Dieldrin; Polychlorinated biphenyls (PCBs); PCB 77; PCB 126; PCB 153; PCB 157; PCB 154; PCB 155; Trifluralin; or combinations thereof.

A fourth embodiment of the current invention includes a method for producing an edible enterosorbent composition. The method comprises the following steps: (a) combining a phyllosilicate-type mineral and a lecithin, (b) mixing for a period of time at a temperature; and (c) forming the edible enterosorbent composition. The edible enterosorbent composition produced in this way is capable of up to 100% cation exchange capacity. Additionally, the edible enterosorbent composition is capable of increasing adsorption of one or more toxins selected from mycotoxins, environmental chemicals, microbes pesticides; herbicides or combinations thereof. A person having ordinary skill in the art can visualize the increased adsorption as a maximum binding capacity (Qmax) and/or distribution coefficient (Kd) of the enterosorbent composition that is greater than the phyllosilicate-type mineral alone and/or a decreased number of microbe colony forming units (CFUs) relative to the phyllosilicate-type mineral alone.

The phyllosilicate-type minerals useful for this method can be selected from a group comprising: a synthetic phyllosilicate type mineral or a natural phyllosilicate-type mineral further selected from a montmorillonite clay; a sodium montmorillonite clay; a calcium montmorillonite clay or combination thereof. A preferred montmorillonite clay is a hydrated sodium calcium aluminosilicate clay having a particle size less than 80 microns and is free from detectable levels of total tetra-dioxin, total pentachlorodibenzodioxin, and total hexachlorodibenzodioxin; wherein the detectable levels of total tetrachlorodibenzodioxin are above 0.024 pg/L; the detectable levels of total pentachlorodibenzodioxin are above 0.025 pg/L; and the detectable levels of total hexachlorodibenzodioxin are above 0.039 pg/L.

A fifth embodiment of this invention includes pretreating the phyllosilicate-type mineral with a strong acid for an acid-treatment-period-of-time and forming a strong-acid-treated phyllosilicate mineral having increased numbers and types of toxin binding sites of the enterosorbent composition. A process known as "acid-drying" the strong-acid-treated phyllosilicate mineral at an acid-drying-temperature for an acid-drying-period-of-time can be used for increasing adsorption, wherein the acid-treatment-period-of-time, the acid-drying-temperature and the acid-drying-period-of-time are sufficient to allow the strong-acid-treated phyllosilicate mineral to have a powder consistency capable of grinding and sieving. The dried strong-acid-treated-phyllosilicate can be used to replace the phyllosilicate-type mineral of the method described above to increase adsorption one or more toxins even more, wherein the observed enterosorption is visualized as a maximum binding capacity (Qmax) and/or distribution coefficient (Kd) that is greater than or equal to that of a carbon material and/or a decreased number of microbe colony forming units (CFUs) relative to the phyllosilicate-type mineral alone.

In a preferred embodiment, the strong-acid can be selected from a group of strong acids comprising: dilute sulfuric acid; battery acid; chamber acid, tower acid, concentrated sulfuric acid, near-saturated, saturated calcium sulfuric acid, or super-saturated calcium sulfuric acid, sulfate anions, or combinations thereof, and/or complex ions containing calcium, sulfates, strong acidic solution with sparingly-soluble Group IIA complexes; or combinations thereof. Preferably, the acid-treatment-period-of-time will be in the range of 1 minute to 8 h; the acid-drying-temperature to be in the range of 15° C. to 120° C.; and the acid-drying-period-of-time to be in the range of 0 minutes to 8 h.

The edible enterosorbent composition is dried at an enterosorbent-drying-temperature for an enterosorbent-drying-period-of-time and then the dried edible enterosorbent composition is sized to have a uniform particle size of less than 150 μm. Generally, the enterosorbent-drying-temperature and an enterosorbent-drying-period-of-time are sufficient to allow the edible enterosorbent composition to have a powder consistency capable of grinding, sieving or air classifying. Preferably, the enterosorbent-drying-period-of-time is in the range of 1 second to 8 h; and the enterosorbent-drying-temperature to be in the range of 15° C. to 120° C.

A sixty embodiment is a method of reducing toxin exposure of a living-being at risk of toxin exposure. The method includes (Step A) introducing an edible enterosorbent composition into the living-being, or introducing an edible enterosorbent into an environment the living being will be exposed to the toxin, or a combination thereof; (Step B) waiting a period of time; and repeating step (a) until the toxin exposure has been reduced. The edible enterosorbent comprises a phyllosilicate-type mineral and a lecithin capable of up to 100% cation exchange capacity; wherein the edible enterosorbent composition is capable of increasing adsorption of one or more toxins selected from mycotoxins, environmental chemicals, microbes pesticides; herbicides or combinations thereof; wherein increased adsorption is determined as a maximum binding capacity (Qmax) and/or distribution coefficient (Kd) of the enterosorbent composition that is greater than the phyllosilicate-type mineral alone and/or a decreased number of microbe colony forming units (CFUs) relative to the phyllosilicate-type mineral alone.

A preferred phyllosilicate-type mineral is selected from a group comprising: (a) a synthetic phyllosilicate type mineral; (b) a natural phyllosilicate-type mineral further selected from a montmorillonite clay; a sodium montmorillonite clay; or a calcium montmorillonite clay; (c) a strong-acid-pre-treated phyllosilicate mineral having increased numbers and types of toxin binding sites; (d) a hydrated sodium calcium aluminosilicate clay having a particle size less than 80 microns and is free from detectable levels of total tetrachlorodibenzo-dioxin, total pentachlorodibenzodioxin, and total hexachlorodibenzodioxin; wherein the detectable levels of total tetrachlorodibenzodioxin are above 0.024 pg/L; the detectable levels of total pentachlorodibenzodioxin are above 0.025 pg/L; and the detectable levels of total hexachlorodibenzodioxin are above 0.039 pg/L; or combination thereof.

A seventh embodiment includes the edible enterosorbent composition reducing toxin exposure from a group of toxins comprising: pentachlorophenol (PCP); benzo[a]pyrene (BaP); lindane, diazinon; aldicarb; linuron; aflatoxin (AfB1); zearalenone (ZEN); *Escherichia coli* (*E. coli*); industrial solvents; polycyclic aromatic hydrocarbons (PAHs); 1,2,3-Trichloropropane (TCP); Phenol; Benzene; Toluene; Pyrene; BFF; Naphthalene; 2,4 D; 2,4-Dinitrophenylhydrazine (2,4-DNP); Linuron; Atrazine; Glyphosate; Dichlorodiphenyltrichloroethane (DDT); Paraquat; α-amino-3-hydroxy-5-methyl-4-isoxazolepropionic acid (AMPA); Bisphenol A (BPA); Bisphenol S (BPS); Dibutyl phthalate (DBP); di-2-ethylhexyl phthalate (DEHP); Dieldrin; Polychlorinated biphenyls (PCBs); PCB 77; PCB 126; PCB 153; PCB 157; PCB 154; PCB 155; Trifluralin; or combinations thereof.

An eight embodiment includes combining the edible enterosorbent composition with a means for introducing into the edible enterosorbent composition into the gastrointestinal tract of the living being, wherein the edible enterosorbent composition is combined with one or more of a group selected from: water, flour, feed, foodstuffs, pills, or a combination thereof. The preferred inclusion level of the edible enterosorbent composition in a range of from about 0.0005% to about 0.10% as a percentage of daily food intake per gram.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims Each and every claim is incorporated into the specification as an embodiment of the present invention. Thus, the claims are a further description and are an addition to the detailed description of the present invention. The disclosures of all patents, patent applications, and publications cited herein are hereby incorporated by reference. Unless expressly stated otherwise, the steps in a method claim may be performed in any order and with any suitable combination of materials and processing conditions.

What is claimed is:

1. A method for reducing exposure to acute ingestible toxins in a living being, comprising:
   (a) administering an edible enterosorbent composition to the gastrointestinal tract of the living being at risk of acute toxin exposure, wherein the composition comprises:
      (i) an acid-treated montmorillonite mineral selected from montmorillonite clay, sodium montmorillonite clay, or calcium montmorillonite clay, wherein the mineral is pre-treated with a strong acid to enhance toxin-binding sites, has a particle size less than 80 microns, and is free from detectable levels of total tetra-dioxin above 0.024 pg/L, total penta-dioxin above 0.025 pg/L, and total hexa-dioxin above 0.039 pg/L; and
      (ii) lecithin in an amount of >2% to 75% by weight, capable of up to 100% cation exchange capacity;
   (b) selecting one or more acute ingestible toxins to be reduced from the group consisting of pentachlorophenol, benzo[a]pyrene, lindane, diazinon, aldicarb, linuron, industrial solvents, polycyclic aromatic hydrocarbons, 1,2,3-trichloropropane, phenol, benzene, toluene, pyrene, naphthalene, 2,4-D, 2,4-dinitrophenylhydrazine, atrazine, glyphosate, dichlorodiphenyltrichloroethane, paraquat, α-amino-3-hydroxy-5-methyl-4-isoxazolepropionic acid, bisphenol A, bisphenol S, dibutyl phthalate, di-2-ethylhexyl phthalate, dieldrin, polychlorinated biphenyls (PCB 77, PCB 126, PCB 153, PCB 157, PCB 154, PCB 155), trifluralin, or combinations thereof;
   (c) waiting a period of time; and
   (d) repeating step (a) until exposure to the selected acute ingestible toxins is reduced; wherein the edible enterosorbent composition binds the selected acute ingestible toxins with a maximum binding capacity (Qmax) or distribution coefficient (Kd) greater than that of the montmorillonite mineral alone, as determined by reduced microbe colony forming units, improved hydra morphology scale (0 to 10, where 10 is normal and 0 is disintegrated), or both.

2. The method of claim 1, further comprising a step of: combining the edible enterosorbent composition with a means for introducing into the edible enterosorbent composition into the gastrointestinal tract of the living being, wherein the edible enterosorbent composition is combined with one or more of a group selected from: water, flour, feed, foodstuffs, pills, or a combination thereof.

3. The method of claim 1, further comprising a step of: introducing the edible enterosorbent composition at an inclusion level in a range of from about 0.0005% to about 0.10% as a percentage of daily food intake per gram.

4. A method for reducing acute ingestible toxin exposure risk from an environment contaminated with toxins, comprising:
   (a) introducing an edible enterosorbent composition into a toxin contaminated environment, wherein the composition comprises:
      (i) an acid-treated montmorillonite mineral selected from montmorillonite clay, sodium montmorillonite clay, or calcium montmorillonite clay, wherein the mineral is pre-treated with a strong acid to enhance toxin-binding sites, has a particle size less than 80 microns, and is free from detectable levels of total tetra-dioxin above 0.024 pg/L, total penta-dioxin above 0.025 pg/L, and total hexa-dioxin above 0.039 pg/L; and
      (ii) lecithin in an amount of >2% to 75% by weight, configured to enhance cation exchange capacity;
   (b) selecting one or more acute ingestible toxins to be reduced from the group consisting of: pentachlorophenol (PCP); benzo[a]pyrene (BaP); lindane; diazinon; aldicarb; linuron; industrial solvents; polycyclic aromatic hydrocarbons (PAHs); 1,2,3-Trichloropropane (TCP); Phenol; Benzene; Toluene; Pyrene; BFF; Naphthalene; 2,4 D; 2,4-Dinitrophenylhydrazine (2,4-DNP); Atrazine; Glyphosate; Dichlorodiphenyltrichloroethane (DDT); Paraquat; α-amino-3-hydroxy-5-methyl-4-isoxazolepropionic acid (AMPA); Bisphenol A (BPA); Bisphenol S (BPS); Dibutyl phthalate (DBP); di-2- ethylhexyl phthalate (DEHP); Dieldrin; Polychlorinated biphenyls (PCBs); PCB 77; PCB 126; PCB 153; PCB 157; PCB 154; PCB 155; Trifluralin; or combinations thereof; or combinations thereof;

(c) waiting a period of time; and (d) repeating step (a) until the acute ingestible toxin exposure risk in the environment is reduced; wherein the edible enterosorbent composition binds the selected acute ingestible toxins with a maximum binding capacity (Qmax) or distribution coefficient (Kd) greater than that of the montmorillonite mineral alone, as determined by reduced microbe colony forming units, a hydra morphology scale graded from 0 to 10 (where 10 is normal and 0 is disintegrated), or both.

\* \* \* \* \*